(12) United States Patent
Pratt et al.

(10) Patent No.: US 9,738,606 B2
(45) Date of Patent: Aug. 22, 2017

(54) SUBSTITUTED DIARYLAMINES AND USE OF SAME AS ANTIOXIDANTS

(75) Inventors: Derek A. Pratt, Ottawa (CA); Jason J. Hanthorn, Eastlake, OH (US); Luca Valgimigli, Bologna (IT)

(73) Assignees: Queen's University at Kingston, Kingston (CA); Alma Mater Studiorum—Universita Di Bologna, Bologna (IT)

( * ) Notice: Subject to any disclaimer, the term of this patent is extended or adjusted under 35 U.S.C. 154(b) by 182 days.

(21) Appl. No.: 14/123,452

(22) PCT Filed: Jun. 4, 2012

(86) PCT No.: PCT/CA2012/000546
§ 371 (c)(1),
(2), (4) Date: Mar. 6, 2014

(87) PCT Pub. No.: WO2012/162818
PCT Pub. Date: Dec. 6, 2012

(65) Prior Publication Data
US 2014/0206585 A1 Jul. 24, 2014

Related U.S. Application Data

(60) Provisional application No. 61/493,340, filed on Jun. 3, 2011.

(51) Int. Cl.
| | |
|---|---|
| C07D 213/74 | (2006.01) |
| C07D 239/48 | (2006.01) |
| C07D 401/12 | (2006.01) |
| C07C 7/20 | (2006.01) |
| C07C 67/62 | (2006.01) |
| C08K 5/3462 | (2006.01) |
| C08K 5/3432 | (2006.01) |
| C09K 15/30 | (2006.01) |
| C07D 239/42 | (2006.01) |
| C07D 239/47 | (2006.01) |
| C10M 169/04 | (2006.01) |

(52) U.S. Cl.
CPC .............. *C07D 213/74* (2013.01); *C07C 7/20* (2013.01); *C07C 67/62* (2013.01); *C07D 239/42* (2013.01); *C07D 239/47* (2013.01); *C07D 239/48* (2013.01); *C07D 401/12* (2013.01); *C08K 5/3432* (2013.01); *C08K 5/3462* (2013.01); *C09K 15/30* (2013.01); *C10M 169/04* (2013.01)

(58) Field of Classification Search
CPC .. C07D 213/74; C07D 239/48; C07D 401/12; C07C 169/04; C07C 7/20; C07C 67/62; C08K 5/3462; C08K 5/3432; C09K 15/30
USPC ................ 508/266; 544/322, 296, 330, 331; 546/304, 307, 264; 554/5; 585/2
See application file for complete search history.

(56) References Cited

U.S. PATENT DOCUMENTS

2011/0130562 A1* 6/2011 Berl ........................ C07C 1/321
540/604

FOREIGN PATENT DOCUMENTS

| EP | 0608548 | 8/1994 |
|---|---|---|
| EP | 1437395 | 7/2004 |
| EP | 1792893 | 3/2006 |
| EP | 2075309 | * 1/2009 |
| GB | 1153196 | 5/1969 |
| KR | 2011/0057078 | 5/2011 |
| KR | 2011/0068162 | 6/2011 |
| WO | WO02/069922 | 9/2002 |
| WO | WO2006/027348 | 3/2006 |
| WO | WO2010/099852 | 9/2010 |
| WO | 2011021726 | * 2/2011 |
| WO | WO2011/073149 | 6/2011 |
| WO | WO2013/075253 | 5/2013 |

OTHER PUBLICATIONS

Journal of American Chemical Society, 2008, 130 (42), 13848-13849.*
Kuhn et al., Validation and use of the M-PBSA Approach for drug discovery. Journal of Medicinal Chemistry, 2005, 48 (12), 4040-4048.*
Namjoshi et al., Development of a two-step route to 3-PBC and BCCt, two agents active against alcohol self-administration in rodent and primate models; Journal of Organic Chemistry (2011), 76(11), 4721-4727.*
Anderson et al., Monodentate phosphines provide highly active catalysts for Pd-catalyzed C—N bond-forming reactions of heteroaromatic halides/amines and (H)N-heterocycles; Angewandte Chemie, International Edition (2006), 45(39), 6523-6527.*
Peterson et al., Reinvestigation of the Synthesis of 5-arylamino-2-picolines; Journal of Heterocyclic Chemistry (1977), 14(3), 527-9.*

(Continued)

*Primary Examiner* — Alexander R Pagano
*Assistant Examiner* — Ebenezer O Sackey
(74) *Attorney, Agent, or Firm* — Lowenstein Sandler LLP; Angela P. Lyon

(57) ABSTRACT

A compound of Formula I, Formula IA, Formula IB, or Formula II, or an acid or base addition salt thereof, and use of these compounds as antioxidants.
In one embodiment, a compound of Formula II,

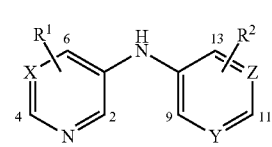

(II)

wherein each of X, Y, and Z are independently a carbon or nitrogen atom; $R^1$ and $R^2$ are each independently a hydrogen or an electron donating group, but are not both hydrogen, and wherein $R^1$, and $R^2$ are each bonded to a carbon atom in their own respective aryl ring.

16 Claims, 7 Drawing Sheets

(56) References Cited

OTHER PUBLICATIONS

International Search Report for International Application No. PCT/CA2012/000546 dated Sep. 25, 2012.
Written Opinion for International Application No. PCT/CA2012/000546 dated Sep. 25, 2012.
Database CAS Registry (Registry No. 942153-34-6) 2010.
Chao et al., "Some Synergistic Antioxidant for Synthetic Lubricants", American Chemical Society, Division of Petroleum Chemistry, Mar. 28, 1982, 27(2) 362.
Database CAS Registry (Registry No. 1313610-01-3) 2009; (Registry No. 1369179-14-5) 2009; (Registry No. 1372771-03-3) 2009; (Registry No. 1372771-29-3) 2009; (Registry No. 1372772-79-6) 2009; (Registry No. 1372779-42-4) 2009.
Database CAS Registry (Registry No. 5051-97-8) 2010.
Database CAS Registry (Registry No. 833453-23-9) 2010; (Registry No. 833453-24-0) 2010.
Hanthorn et al., "Inc. of Ring Nitrogens into Diphenylamine Antioxidants: Striking a Balance between Reactivity and Stability" J. Am. Chem. Soc. Feb. 2012, 34, 8306-8309.

\* cited by examiner

SUBSTITUTED DIARYLAMINES AND USE OF SAME AS ANTIOXIDANTS

FIELD OF THE INVENTION

This invention relates to substituted heteroaromatic diarylamine compounds which are particularly useful as antioxidants.

BACKGROUND OF THE INVENTION

Antioxidants are compounds that can retard oxidation, and thus are useful as additives to increase the stability and lifespan of one or more organic substrates that are subject to oxidative degradation that can be induced by heat and/or light. Antioxidants can be useful as protective additives in engine oils, automatic transmission fluids, industrial utility grade oils, compressor oils, gear and hydraulic oils, biodiesels, plastics, rubber and rubber like substances, unsaturated monomers, elastomers, adhesives, cosmetics preparations, coatings, dyes, inks, and pharmaceutical preparations. Antioxidants are also useful as additives present during the processing or synthesis of many organic substrates, for example as additives during polymerization, because of the ability of the antioxidant to scavenge free radicals, and thus improve the yield, stability and longevity of the desired resulting product.

Antioxidants are commonly added to organic substrates such as combustion engine lubricating oils, to assist in reducing unwanted oxidation, and increasing performance standards. Combustion engine lubricants oxidize readily at the high operating temperatures of an engine, and in turn, have diminished lubricating capacity as the viscosity of the lubricant increases, and the oxidation products accumulate to form deposits, which in turn leads to greater wear on engine parts.

The chemical mechanism of a typical oxidation reaction (a free radical chain reaction) which benefits from the addition of an antioxidant is shown in Equation 1 below for a generic hydrocarbon R—H:

Equation 1

Initiation:

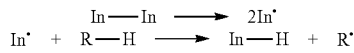

Propagation:

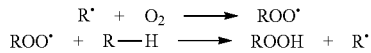

Termination:

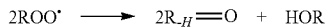

The initiation reaction is typically a reaction that gives rise to radicals, but is often the homolytic decomposition of a hydroperoxide at high temperatures, or the dissociative electron transfer to a hydroperoxide in the presence of low valent metal ions (e.g. $Fe^{2+}$, $Cu^{1+}$) or other good reductants.

A key strategy in decreasing the rate at which an organic substrate oxidizes is the addition of small quantities of antioxidant compounds which trap the intermediate radicals that carry on the oxidation process. These antioxidants should be compatible with the organic product of interest and/or the formulation thereof, and should themselves be robust and stable.

One of the common types of compounds used as an antioxidant additive are compounds based on diphenylamines (Formula A).

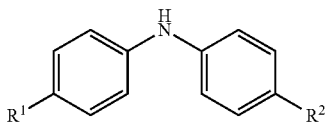

Formula A

Diphenylamines with antioxidant activity are well known in the art. See for example, U.S. Pat. No. 2,180,936, U.S. Pat. No. 3,655,559; U.S. Pat. No. 3,944,492; U.S. Pat. No. 5,750,787; U.S. Pat. No. 6,315,925, and U.S. Pat. No. 2,530,769, all of which, without adopting any definitions as found therein, are incorporated herein by reference.

For example, U.S. Pat. No. 3,655,559 discloses alkylated diphenylamines useful as additives to lubricating oils. U.S. Pat. No. 2,180,936 describes use of substituted diphenylamines in the manufacture of rubber and rubber like compounds to impart age-resisting qualities as a result of the antioxidant capabilities of these compounds.

Other diphenylamines are also well known in the art. See for example U.S. Pat. No. 3,944,492 which discloses use of derivatives of diphenylamines and phenylnapthylamines as antioxidants and U.S. Pat. No. 5,750,787 which describes octyl-substituted diphenylamines.

While substituted diphenylamine antioxidants are used commercially as the additives of choice at high temperatures, the radical trapping activities of these compounds are only modest at ambient temperatures due to relatively low inhibition rate constants ($k_{inh}$, see Eq. 2) that is the rate controlling parameter in inhibited autoxidations.

Equation 2

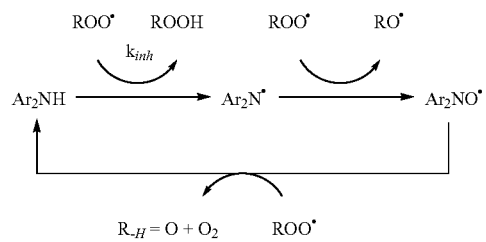

At higher temperatures, these compounds become more effective, since catalytic activities, which are not fully understood but are ascribed to the intervention of nitroxides, become relevant (Korcek, S, and Jensen, R. K. "Relation Between Base Oil Composition and Oxidation Stability at Increased Temperatures", *ASLE Transactions*, Vol. 19, No. 2, 1975 pp. 83-94 and Jensen, R. K.; Korcek, S.; Zinbo, M.; Gerlock, J. L. *J. Org. Chem.* 1995, 60, 5396-5400).

Efforts to design diphenylamine-based antioxidants with improved reactivity while maintaining stability have met with little success, since the candidates are often unstable in air, making them more likely to act as pro-oxidants and complicating their preparation, handling and storage.

As such, it would be advantageous to have antioxidant compounds that are stable with longevity and utility, while still maintaining their reactivity. The ability to be stable at both ambient temperature and elevated temperatures would also be beneficial.

SUMMARY OF THE INVENTION

It is an object of the present invention to obviate or mitigate at least one of the disadvantages of the prior art, by providing novel substituted diarylamines, wherein at least one of the aryl rings is a heteroaryl, and/or providing novel uses thereof. Compounds of the invention are particularly useful as antioxidants.

In a first aspect, the present invention provides for a compound of Formula I or a salt thereof, Formula I wherein X is carbon or nitrogen, wherein $R^1$ and $R^2$ are each independently a hydrogen or an electron donating group, but are not both hydrogen, and wherein $R^1$ and $R^2$ are each bonded to a carbon atom within their respective aryl ring.

In another aspect, the present invention provides for a compound of Formula IA or a salt thereof, Formula IA wherein each of X and Y are independently a carbon or nitrogen atom, and wherein $R^1$ and $R^2$ are each independently a hydrogen or an electron donating group, but are not both hydrogen, and wherein $R^1$ and $R^2$ are each bonded to a carbon atom within their respective aryl ring.

In another aspect, the present invention provides for a compound of Formula IB or a salt thereof, Formula IB wherein each of X, Y, and Z are independently a carbon or nitrogen atom, and wherein $R^1$ and $R^2$ are each independently a hydrogen or an electron donating group, but are not both hydrogen, and wherein $R^1$ and $R^2$ are each bonded to a carbon atom within their respective aryl ring.

In another aspect, the present invention provides a compound of Formula I, Formula IA, and/or Formula IB, or a salt thereof, wherein the electron donating group is: (i) an aliphatic moiety; (ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect, the present invention provides a compound of Formula I, Formula IA, and/or Formula IB, or a salt thereof, wherein the electron donating group is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently hydrogen aromatic moiety, an aliphatic moiety or a combination thereof.

In another aspect, the present invention provides a compound of Formula I, Formula IA, and/or Formula IB or a salt thereof, wherein the electron donating group is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another embodiment, $R^4$ and $R^5$ are not both hydrogen. In yet another embodiment $R^3$ is not a hydrogen.

In another aspect, $R^1$ is bonded to a carbon atom at any one of positions 3, 4, 5, and 6 of Formula I, Formula IA, and/or Formula IB. In yet another aspect $R^2$ is bonded to a carbon atom at any one of positions 9, 10, 11, 12, and 13 of Formula I, Formula IA, and/or Formula IB.

In yet another aspect, $R^1$ is bonded to a carbon atom at position 6 of Formula I and/or Formula IA and is: i) a hydrogen; (ii) a $C_1$ to $C_3$ hydrocarbon group; (iii) $OR^3$ group wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In yet another aspect, $R^2$ is bonded to a carbon atom at position 9 or 13 of Formula I, Formula IA, and/or Formula IB and is: i) a hydrogen; (ii) a $C_1$ to $C_3$ hydrocarbon group; (iii) $OR^3$ wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In yet another aspect, $R^1$ is bonded to a carbon atom at position 4 of Formula I, Formula IA, and/or Formula IB and is: i) a hydrogen; (ii) a $C_1$ to $C_{20}$ hydrocarbon group; (iii) $OR^3$ wherein $R^3$ is a hydrogen or $C_1$ to $C_{20}$ hydrocarbon group; or
(iv) $NR^4R^5$ wherein $R^4$ and $R^5$ are each independently hydrogen or a $C_1$ to $C_{20}$ hydrocarbon group; wherein $R^1$ and $R^2$ are not both hydrogen.

In yet another aspect, $R^2$ is bonded to a carbon atom at position 11 of Formula I, Formula IA, and/or Formula IB and is: i) a hydrogen; (ii) a $C_1$ to $C_{20}$ hydrocarbon group; (iii) $OR^3$ wherein $R^3$ is a hydrogen or $C_1$ to $C_{20}$ hydrocarbon group, or (iv) $NR^4R^5$ wherein $R^4$ and $R^5$ are each independently hydrogen or a $C_1$ to $C_{20}$ hydrocarbon group; wherein $R^1$ and $R^2$ are not both hydrogen.

In another aspect, the present invention provides a compound of Formula II or a salt thereof, Formula II wherein each of X, Y, and Z are independently a carbon or nitrogen atom, wherein $R^1$ and $R^2$ are each independently a hydrogen or an electron donating group, but are not both hydrogen, and wherein $R^1$ and $R^2$ are each bonded to a carbon atom in their respective aryl ring, with the proviso that the compound is not $N^1,N^1$-dimethyl-$N^4$-(pyridin-3-yl)benzene-1,4-diamine, and is not N-(pyridine-3-yl)-3-methylaniline.

In another aspect, the present invention provides a compound of Formula II or a salt thereof, wherein the electron donating group is: (i) an aliphatic moiety; (ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect, the present invention provides a compound of Formula II or a salt thereof, wherein the electron donating group is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently hydrogen aromatic moiety, an aliphatic moiety or a combination thereof.

In another aspect, the present invention provides a compound of Formula II or a salt thereof, wherein the electron donating group is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another embodiment, $R^4$ and $R^5$ are not both hydrogen. In yet another embodiment $R^3$ is not a hydrogen.

In another aspect, $R^1$ is bonded to a carbon atom at any one of positions 2, 4, 5, and 6 of Formula II. In yet another aspect $R^2$ is bonded to a carbon atom at any one of positions 9, 10, 11, 12, and 13 of Formula II.

In yet another aspect, $R^1$ is bonded to a carbon atom at position 2 or 6 of Formula II and is: i) a hydrogen; (ii) a $C_1$ to $C_3$ hydrocarbon group; (iii) $OR^3$ wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In yet another aspect, $R^2$ is bonded to a carbon atom at position 9 or 13 of Formula II and is: i) a hydrogen; (ii) a $C_1$ to $C_3$ hydrocarbon group; (iii) $OR^3$ wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In yet another aspect, $R^1$ is bonded to a carbon atom at position 4 of Formula II and is: i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; wherein $R^1$ and $R^2$ are not both hydrogen.

In yet another aspect, $R^2$ is bonded to a carbon atom at position 11 of Formula II and is: i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; wherein $R^1$ and $R^2$ are not both hydrogen.

In another aspect, the present invention is a composition comprising an organic substrate and one or more compounds of Formula I, Formula IA, and/or Formula IB, or a salt thereof, wherein X, Y and Z (if present) are independently a carbon or nitrogen atom, wherein each of $R^1$ and $R^2$ are independently a hydrogen or an electron donating group, but are not both hydrogen, and wherein $R^1$ and $R^2$ are each bonded to a carbon atom within their respective aryl ring, wherein the compounds are present in a an amount sufficient to reduce the level of degradation of the organic substrate when compared to the level of degradation of said organic substrate in the absence of said compound(s).

In yet another aspect, the present invention is a composition comprising an organic substrate and one or more compounds of Formula II, or a salt thereof, wherein each of X, Y, and Z are independently a carbon or nitrogen atom, wherein each of $R^1$ and $R^2$ are independently a hydrogen or an electron donating group, but are not both hydrogen, and wherein $R^1$ and $R^2$ are each bonded to a carbon atom within their respective aryl ring, wherein the compound(s) are present in an amount sufficient to reduce the level of degradation of the organic substrate, when compared to the level of degradation of said organic substrate in the absence of said compound(s).

In another aspect, the electron donating group of the composition is: (i) an aliphatic moiety; (ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect, the electron donating group of the composition is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently a hydrogen or an aromatic moiety, an aliphatic moiety, or a combination thereof.

In another aspect, the electron donating group of the composition is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another embodiment, $R^4$ and $R^5$ of the composition are not both hydrogen. In yet another embodiment $R^3$ of the composition is not a hydrogen.

In another aspect, $R^1$ is bonded to a carbon atom at any one of positions 3, 4, 5, and 6 of Formula I, Formula IA, and/or Formula IB. In yet another aspect $R^2$ is bonded to a carbon atom at any one of positions 10, 11, 12, and 13 of Formula I, Formula IA, and/or Formula IB.

In another aspect, $R^1$ is bonded to a carbon atom at any one of positions 2, 4, 5, and 6 of Formula II. In yet another aspect $R^2$ is bonded to a carbon atom at any one of positions 9, 10, 11, 12, and 13 of Formula II.

In some embodiments, the organic substrate is selected from the group consisting of lubricants, biofuels, plastics, rubbers, polymers, elastomers, cosmetic preparations, coatings, dyes, inks, pharmaceutical preparations, food preparations and adhesives. In some embodiments, the organic substrate is a lubricant and the one or more compounds are present in an amount of about 0.01 to about 6 weight percent of the lubricant. In other embodiments, the compounds are present in an amount of about 0.03 to about 2.5 weight percent. In other embodiments, additional antioxidants are added. In yet other embodiments, the additional antioxidant is a sterically hindered phenol.

In another aspect, the present invention is a composition comprising an organic substrate and one or more compounds of Formula I, Formula IA, and/or Formula IB, or a salt thereof, wherein X, Y and Z (if present) are independently a carbon or nitrogen atom, wherein each of $R^1$ and $R^2$ are independently a hydrogen or an electron donating group, but are not both hydrogen, wherein $R^1$ and $R^2$ are each bonded to a carbon atom within their respective aryl ring, and wherein the compound(s) are present in an amount sufficient to scavenge at least one free radical species existing and/or formed within the composition.

In yet another aspect, the present invention is a composition comprising an organic substrate and one or more compounds of Formula II, or a salt thereof, wherein each of X, Y, and Z are independently a carbon or nitrogen atom, wherein $R^1$ and $R^2$ are each independently a hydrogen or an electron donating group, but are not both hydrogen, wherein $R^1$ and $R^2$ are each bonded to a carbon atom within their respective aryl ring, and wherein the compounds are present in an amount sufficient to scavenge at least one free radical species existing and/or formed within the composition.

In another aspect, the present invention provides a composition of Formula I, Formula IA, and/or Formula IB, or a salt thereof, wherein the electron donating group is: (i) an aliphatic moiety;
(ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect, the present invention provides a composition of Formula I, Formula IA, and/or Formula IB, or a salt thereof, wherein the electron donating group is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently a hydrogen or an aromatic moiety, an aliphatic moiety, or a combination thereof.

In another aspect, the present invention provides a composition of Formula I, Formula IA, and/or Formula IB, or a salt thereof, wherein the electron donating group is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another aspect, the present invention provides a composition of Formula II or a salt thereof, wherein the electron donating group is: (i) an aliphatic moiety;
(ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect, the present invention provides a composition of Formula II or a salt thereof, wherein the electron donating group is: (i) an aromatic moiety, aliphatic moiety or combinations thereof; (ii) $OR^3$ wherein $R^3$ is a hydrogen or an aromatic moiety, an aliphatic moiety or combinations thereof; or (iii) $NR^4R^5$ wherein $R^4$ and $R^5$ are each independently hydrogen or an aromatic moiety, an aliphatic moiety, or combinations thereof.

In another aspect, the present invention provides a composition of Formula II or a salt thereof, wherein the electron donating group is: (i) a $C_1$ to $C_{20}$ hydrocarbon group;
(ii) $OR^3$ wherein $R^3$ is a hydrogen or a $C_1$ to $C_{20}$ hydrocarbon group; or
(iii) $NR^4R^5$ wherein $R^4$ and $R^5$ are each independently hydrogen or a $C_1$ to $C_{20}$ hydrocarbon group.

In another embodiment $R^4$ and $R^5$ of Formula I, Formula IA, Formula IB and/or Formula II are not both hydrogen. In yet another embodiment $R^3$ of Formula I Formula IA, Formula IB and/or Formula II is not a hydrogen.

In some embodiments, the invention encompasses the use of a compound of Formula I, Formula IA and/or Formula IB, or a salt thereof, as an antioxidant, wherein X is a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring.

In some embodiments, the invention encompasses the use of a compound of Formula II, or a salt thereof, as an antioxidant, wherein each of X, Y, and Z are independently a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring.

In another aspect of the use, the electron donating group of Formula I, Formula IA, Formula IB, and/or Formula II is: (i) an aliphatic moiety; (ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another aspect of the use, the electron donating group of Formula I, Formula IA, Formula IB, and/or Formula II is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently a hydrogen or an aromatic moiety, an aliphatic moiety, or a combination thereof.

In another aspect of the use, the electron donating group of Formula I, Formula IA, Formula IB, and/or Formula II is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another embodiment $R^4$ and $R^5$ of Formula I, Formula IA, Formula IB and/or Formula II are not both hydrogen. In yet another embodiment $R^3$ of Formula I, Formula IA, Formula IB and/or Formula II is not a hydrogen.

In another aspect, the invention encompasses the use of a compound of Formula I, Formula IA, Formula IB (or a salt thereof) as an antioxidant, wherein $R^1$ is bonded to a carbon atom at any one of positions 3, 4, 5, and 6. In yet another aspect $R^2$ is bonded to a carbon atom at any one of positions 9, 10, 11, 12, and 13.

In another aspect, the invention encompasses the use of a compound of Formula II (or a salt thereof) as an antioxidant, wherein $R^1$ is bonded to a carbon atom at any one of positions 2, 4, 5, and 6. In yet another aspect $R^2$ is bonded to a carbon atom at any one of positions 9, 10, 11, 12, and 13.

In yet other embodiments, the invention encompasses a method of preventing or reducing the level of degradation of an organic substrate, comprising adding to the composition comprising or resulting in the organic substrate, an effective amount of an antioxidant of Formula I, Formula IA, and/or Formula IB (or a salt thereof) wherein X, Y and Z (if present) are independently a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring.

In yet other embodiments, the invention encompasses a method of preventing or reducing the level of degradation of an organic substrate, comprising adding to the composition comprising or resulting in the organic substrate, an effective amount of an antioxidant of Formula II (or a salt thereof) wherein each of X, Y, and Z are independently a carbon or nitrogen atom, wherein $R^1$ and $R^2$ are each independently a hydrogen or an electron donating group, but are not both hydrogen, and wherein $R^1$ and $R^2$ are each bonded to a carbon atom within their respective aryl ring.

In yet another embodiment, the invention encompasses a method of improving the stability and/or yield of an organic substrate in a composition by adding to the composition comprising or resulting in the organic substrate, an effective amount of an antioxidant of Formula I, Formula IA, and/or Formula IB (or a salt thereof), wherein each of X, Y, and Z (if present) are independently a carbon or nitrogen atom, $R^1$ and $R^2$ are each independently a hydrogen or an electron donating group, but are not both hydrogen, and $R^1$ and $R^2$ are each bonded to a carbon atom within their respective aryl ring, so that said compound can scavenge at least one free radical species existing and/or formed within the composition, thus improving the stability and/or yield of the organic substrate.

In yet another embodiment, the invention encompasses a method of improving the stability and/or yield of an organic substrate in a composition by adding to the composition comprising or resulting in the organic substrate, an effective amount of an antioxidant of Formula II (or a salt thereof), wherein each of X, Y, and Z are independently a carbon or nitrogen atom, $R^1$ and $R^2$ are each independently a hydrogen or an electron donating group, but are not both hydrogen, and $R^1$ and $R^2$ are each bonded to a carbon atom within their respective aryl ring so that said compound can scavenge at least one free radical species existing and/or formed within the composition, thus improving the stability and/or yield of the organic substrate.

In yet another embodiment, the composition comprises one or more monomers, which are to be used in the synthesis of a polymer.

In yet another embodiment, the composition comprising one or more compounds of Formula I, Formula IA, and/or Formula IB, or a salt thereof, wherein each of X, Y, and Z (if present) are independently a carbon or nitrogen atom, wherein each of $R^1$ and $R^2$ are independently a hydrogen or an electron donating group, but are not both hydrogen; and wherein $R^1$ and $R^2$ are each bonded to a carbon atom in their respective aryl ring, and one or more additives; wherein the composition, when added to a mixture comprising or resulting in an organic substrate, reduces the level of degradation of the organic substrate, when compared to the level of degradation of the organic substrate in the absence of said composition.

In another embodiment, the invention encompasses a composition of Formula I, Formula IA, and/or Formula IB, or a salt thereof and one or more additives, wherein the electron donating group of Formula I Formula IA, and/or Formula IB is: (i) an aliphatic moiety; (ii) $OR^3$ wherein $R^3$ is a hydrogen an aliphatic moiety; or (iii) $NR^4R^5$ wherein $R^4$ and $R^5$ are each independently hydrogen or an aliphatic moiety.

In another embodiment, the invention encompasses a composition of Formula I, Formula IA, and/or Formula IB, or a salt thereof and one or more additives, wherein the electron donating group of Formula I Formula IA, and/or Formula IB is: (i) an aromatic moiety, an aliphatic moiety or a combination thereof; (ii) $OR^3$ wherein $R^3$ is a hydrogen or an aromatic moiety, an aliphatic moiety or a combination thereof; or (iii) $NR^4R^5$ wherein $R^4$ and $R^5$ are each independently a hydrogen or an aromatic moiety, an aliphatic moiety, or a combination thereof.

In another embodiment, the invention encompasses a composition of Formula I, Formula IA, and/or Formula IB or a salt thereof and one or more additives, wherein the electron donating group of Formula I Formula IA, and/or Formula IB is: (i) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In yet another embodiment, the composition comprising one or more compounds of Formula II, or a salt thereof, wherein each of X, Y, and Z are independently a carbon or nitrogen atom, wherein each of $R^1$ and $R^2$ are independently a hydrogen or an electron donating group, but are not both hydrogen; and wherein $R^1$ and $R^2$ are each bonded to a carbon atom in their respective aryl ring, and one or more additives; wherein the composition, when added to a mixture comprising or resulting in an organic substrate, reduces the level of degradation of the organic substrate, when compared to the level of degradation of the organic substrate in the absence of said composition.

In another embodiment, the invention encompasses a composition of Formula II or a salt thereof and one or more additives, wherein the electron donating group of Formula II is: (i) an aliphatic moiety; (ii) $OR^3$ wherein $R^3$ is a hydrogen or an aliphatic moiety; or (iii) $NR^4R^5$ wherein $R^4$ and $R^5$ are each independently hydrogen or an aliphatic moiety.

In another embodiment, the invention encompasses a composition of Formula II or a salt thereof and one or more additives, wherein the electron donating group of Formula II is: (i) an aromatic moiety, an aliphatic moiety, or a combination thereof; (ii) $OR^3$ wherein $R^3$ is a hydrogen or an aromatic moiety, an aliphatic moiety, or a combination thereof; or (iii) $NR^4R^5$ wherein $R^4$ and $R^5$ are each independently hydrogen or an aromatic moiety, an aliphatic moiety, or a combination thereof.

In another embodiment, the invention encompasses a composition of Formula II or a salt thereof and one or more additives, wherein the electron donating group of Formula II is: (1) a $C_1$ to $C_{20}$ hydrocarbon group; (ii) $OR^3$ wherein $R^3$ is a hydrogen or a $C_1$ to $C_{20}$ hydrocarbon group; or (iii) $NR^4R^5$ wherein $R^4$ and $R^5$ are each independently hydrogen or a $C_1$ to $C_{20}$ hydrocarbon group.

In another embodiment $R^4$ and $R^5$ of Formula I, Formula IA, Formula IB and/or Formula II are not both hydrogen. In yet another embodiment $R^3$ of Formula I, Formula IA, Formula IB and/or Formula II is not a hydrogen.

In yet another embodiment the one or more additives is selected from the group consisting of: one or more traditional anti-oxidants, anti-wear agents, zinc salts, anti-deposition agents, hydrolytic stabilizers, friction modifiers, seal swell agents, anti-rust agents, foam suppressing agents, and pour point depressants.

In another aspect, the invention encompasses a kit of a compound of Formula I, Formula IA, and/or Formula IB (or a salt thereof) wherein each of X, Y, and Z (if present) are independently a carbon or nitrogen atom, wherein $R^1$ and $R^2$ are each independently a hydrogen or an electron donating group, but are not both hydrogen, and wherein $R^1$ and $R^2$ are each bonded to a carbon atom within their respective aryl ring; and instructions for use of said compound as an antioxidant to improve the stability and/or yield of an organic substrate.

In another aspect, the invention encompasses a kit of a compound of Formula II, (or a salt thereof) wherein each of X, Y, and Z are independently a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring; and instructions for use of said compound as an antioxidant to improve the stability and/or yield of an organic substrate.

In another aspect, the invention encompasses a kit of a compound of Formula I, Formula IA, and/or Formula IB (or a salt thereof) wherein each of X, Y, and Z (if present) are independently a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring; and instructions for use of said compound as an antioxidant to scavenge at least one free radical species from within a composition containing or used to synthesize an organic substrate, thus improving the stability and/or yield of the organic substrate.

In another aspect, the invention encompasses a kit of a compound of Formula II, (or a salt thereof) wherein each of X, Y, and Z are independently a carbon or nitrogen atom, $R^1$ and $R^2$ are each independently a hydrogen or an electron donating group, but are not both hydrogen, and wherein $R^1$ and $R^2$ are each bonded to a carbon atom within their respective aryl ring; and instructions for use of said compound as an antioxidant to scavenge at least one free radical species from within a composition containing or used to synthesize an organic substrate, thus improving the stability and/or yield of the organic substrate.

Other aspects and features of the present invention will become apparent to those ordinarily skilled in the art, upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Definitions

Figure 1A:
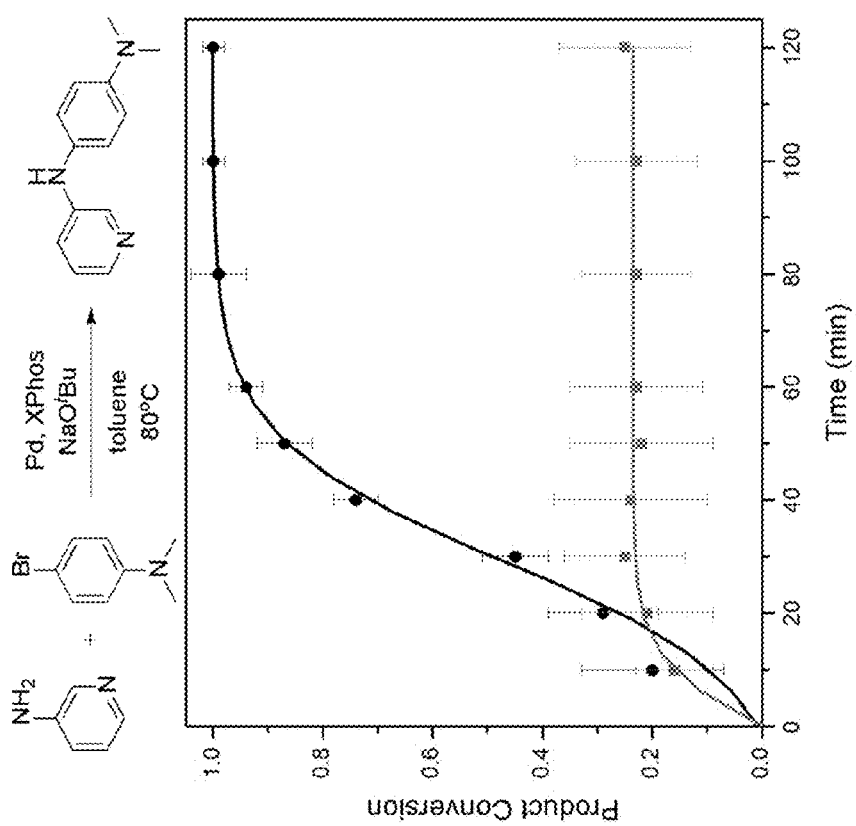
FIGS. 1A, 1B and 1C respectively illustrate, in one embodiment, the comparative reaction profiles of three selected compounds in cross-coupling reactions using two different catalysts.

As used herein, "aliphatic" refers to hydrocarbon moieties that are linear, branched or cyclic, may be alkyl, alkenyl or alkynyl, and may be substituted or unsubstituted.

The term "aromatic hydrocarbon", as used herein, includes hydrocarbons containing at least one aromatic ring.

The terms "aryl", "aryl ring" and "aryl group", as used herein, mean a moiety including a substituted or unsubstituted aromatic ring, including heteroaryl moieties and moieties with more than one conjugated aromatic ring; optionally such moiety may also include one or more non-aromatic ring. The terms "aryl", "aryl ring" and "aryl group" also include heteroaryl groups, wherein at least one ring atom is a non-carbon atom (e.g., Nitrogen (N)).

Accordingly, as used herein, "heteroaryl" means a moiety including a substituted or unsubstituted aromatic ring or ring system having from 3 to 20, or 4 to 10 carbon atoms and at feast one heteroatom in one or more conjugated aromatic rings. As used herein, "heteroatom" refers to non-carbon and non-hydrogen atoms, such as, for example, O, S, and N. Examples of heteroaryl moieties include pyridyl, bipyridyl, indolyl, thienyl, and quinolinyl.

The term "effective amount" herein refers to the amount of compound (or compounds) which is added to an organic substrate so as to provide activity. In some embodiments, the "effective amount" is an amount of compound(s) sufficient to reduce the level of degradation of an organic substrate when compared to the level of degradation of the organic substrate in the absence of said compound(s). In some embodiments, the "effective amount" is an amount sufficient to enable the compound(s) to scavenge one or more free radicals existing, or formed within a composition. In some embodiments, the "effective amount" is an amount sufficient to enable the compound(s) to scavenge one or more free radicals during synthesis of an organic substrate. In some embodiments, the "effective amount" includes up to about 6.0% by weight of the composition, in some embodiments up to about 5.0% by weight of the composition, in some embodiments up to about 3.0% by weight of the composition, in some embodiments up to about 2.5% by weight of the composition, in some embodiments up to about 1.0% by weight of the composition, in some embodiments up to about 0.7% by weight of the composition, in some embodiments up to about 0.5% by weight of the composition, in some embodiments up to about 0.3% by weight of the composition, in some embodiments up to about 0.1% by weight of the composition, in some embodiments about 0.1% to about 6.0% by weight of the composition, in some embodiments about 0.5% to about 3.0% by weight of the composition, in some embodiments about 0.5% to about 1.0% by weight of the composition, in some embodiments about 0.1% to about 1.0% by weight of the composition, in some embodiments about 0.1% to about 2.5% by weight of the composition, in some embodiments about 0.5% to about 1.5% by weight of the composition.

The term "electron donating group" as used herein includes a hydrocarbon group, an alkoxy group ($OR^3$), an amine group, a monosubstituted amine ($NHR^4$), and a disubstituted amine ($NR^4R^5$). The electron-donating strength of the alkoxy or amine group comes largely from the lone pairs of electrons on the O and N atoms, respectively, such that each of $R^3$, $R^4$ and $R^5$ can be a hydrogen or a saturated or unsaturated branched or straight chain hydrocarbon moiety and/or may include one or more cycloaliphatic groups and/or one or more aromatic hydrocarbons, or a combination thereof, while not detracting from the electron donating characteristic of the alkoxy or amine group.

The term "cycloaliphatic" as used herein includes a saturated or unsaturated carbocyclic moiety comprising mono- or bicyclic rings. Cycloaliphatic includes a 3- to 7-membered saturated carbocyclic moiety. Examples of cycloaliphatic moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

The term "hydrocarbon group", as used herein, includes a hydrocarbon containing between 1 to 24 carbons, 1 to 23 carbons, 1 to 22 carbons, 1 to 21 carbons, 1 to 20 carbons, 1 to 19 carbons, 1 to 18 carbons, 1 to 17 carbons, 1 to 16 carbons, 1 to 15 carbons, 1 to 14 carbons, 1 to 13 carbons, 1 to 12 carbons, 1 to 11 carbons, 1 to 10 carbons, 1 to 9 carbons, 1 to 8 carbons, 1 to 7 carbons, 1 to 6 carbons, 1 to 5 carbons, 1 to 4 carbons, 1 to 3 carbons, 2 to 24 carbons, 2 to 21 carbons, 2 to 20 carbons, 2 to 19 carbons, 2 to 18 carbons, 2 to 17 carbons, 2 to 16 carbons, 2 to 15 carbons, 2 to 14 carbons, 2 to 13 carbons, 2 to 12 carbons, 2 to 11 carbons, 2 to 10 carbons, 2 to 9 carbons, 2 to 8 carbons, 2 to 7 carbons, 2 to 6 carbons, 2 to 5 carbons, 2 to 4 carbons, 2 to 3 carbons, 3 to 24 carbons, 3 to 23 carbons, 3 to 22 carbons, 3 to 21 carbons, 3 to 20 carbons, 3 to 19 carbons, 3 to 18 carbons, 3 to 17 carbons, 3 to 16 carbons, 3 to 15 carbons, 3 to 14 carbons, 3 to 13 carbons, 3 to 12 carbons, 3 to 11 carbons, 3 to 10 carbons, 3 to 9 carbons, 3 to 8 carbons, 3 to 7 carbons, 3 to 6 carbons, 3 to 5 carbons, less than 20 carbons, less than 15 carbons, less than 10 carbons, less than 5 carbons, less than 3 carbons, and 1 or 2 carbons, and includes saturated or unsaturated, branched or straight chain hydrocarbon moieties, including aliphatic moieties and/or one or more cycloaliphatic groups and/or one or more aromatic hydrocarbons, or a combination thereof.

The term "degradation", as used herein, includes a process that benefits from the activity of antioxidants. Degradation includes damage that occurs as a result of oxidation and/or the activity of one or more free radicals.

The term "level of degradation", as used herein, refers to a qualitative, semi-qualitative, quantitative or semi-quantitative assessment of the amount and/or extent of damage resulting from degradation, including degradation caused by oxidation and/or the activity of one or more free radicals. The assessment can include functional measurements of the activity of the substance for which the level of degradation is being assessed.

The term "lubricant", as used herein, includes a substance (often a liquid) that can be introduced between two moving surfaces to reduce the friction between them.

The term "organic substrate", as used herein, includes a non-living carbon based compound or composition and includes those carbon based compounds or compositions that can be subjected to oxidative degradation that can be induced by heat and/or light, and can benefit from the addition of an antioxidant. Organic substrates are also compounds that can benefit from a compound that can scavenge at least one free radical species and improve the yield, stability and/or longevity of the organic substrate, for example, a compound added during synthesis of a polymer to scavenge free radicals formed. Therefore, organic substrates include monomers, dimers, trimers and polymers including triglycerides, phospholipids, sphingolipids, and other lipids, which can benefit from the addition of one or more antioxidants able to scavenge free radicals. Included within the definition of organic substrates are oils such as engine oils, automatic transmission fluids, industrial oils, compressor oils, gear and hydraulic oils, and the like. Also included are hydraulic fluids and fuels, biodiesels, plastics, rubber and rubber-like substances, unsaturated monomers, cosmetic preparations, coatings, dyes, inks, pharmaceutical preparations, elastomers, adhesives, and other hydrocarbon based polymers. Also included are oils, fats and waxes typically used in the cosmetic and/or pharmaceutical industry, including those oils, fats and/or waxes comprising esters of saturated and/or monounsaturated and/or polyunsaturated fatty acids, including unsaponifiable fractions obtained from such oils, fats and waxes. Also included are dietary oils and fats, and oils and fats used in manufacturing of food or food ingredients. Included also are oils, fats and waxes such as almond oil, apricot oil, castor oil, corn oil, macadamia nut oil, olive oil, sesame oil, soybean oil, fish oil, bird oil, jojoba oil, bees wax, lanolin, oleic acid, linoleic acid, linolenic acid, and the like, as well as their esters.

The term "salt" as used herein includes, for example, acid addition salts and base addition salts. Acid addition salts include salts wherein the diaryl amine of Formula I or Formula II remains protonated, for example at the heterocyclic nitrogen or the 'reactive' bridging nitrogen. Base addition salts include compounds of Formula I or Formula II resulting in deprotonated amine, as well as the amide form of the amine, which may be generated by treatment with a strong base, for example lithium diisopropylamide.

Compositions

A novel class of substituted diarylamines has been designed, and various examples synthesized and tested, to demonstrate the utility of this new family of heterocyclic amines as antioxidants.

We have found that by creating compounds whereby one or more carbon atoms within either or both of the phenyl rings of a substituted diphenylamine are replaced with nitrogen, we were able to identify compounds which had improved predicted activation enthalpies ($\Delta H^\ddagger$) for reactions with peroxyl radicals, while also maintaining a relatively high predicted ionization enthalpy ($\Delta H^{Ion}$) which reflects their stability in air.

Without wishing to be bound by theory, it is thought that substitution of nitrogen atoms at certain positions within one or both of the phenyl rings of substituted diphenylamines produces an increase in the ionization enthalpy ($\Delta H^{Ion}$), thus stabilizing the compound to one-electron oxidation (such as by reaction with $O_2$ in air or hydroperoxides arising from hydrocarbon oxidation). The greater stability of these derivatives permits substitution with electron-donating groups to increase their reactivities as radical-trapping antioxidants by lowering the activation enthalpy ($\Delta H^\ddagger$) for reactions with peroxyl radicals. Thus it is expected that all diphenylamines demonstrating antioxidant activity can be improved by the replacement of the substituted phenyl rings with substituted heteroaryl rings.

In certain embodiments, the heteroaryl group(s) contain one or more atoms at the ortho position of the aryl group(s) which are nitrogen. In other embodiments, the heteroaryl group(s) contain one or more atoms at the meta position of the aryl group(s) which are nitrogen.

As such, compounds of the invention are particularly useful as antioxidants, alone or in combination with other antioxidants. Compounds of the invention can also have improved stability at ambient temperature and/or increased longevity and/or greater stability than previously known antioxidants, including diphenylamines, and thus can be particularly beneficial in the preparation, handling and/or storage of these compounds.

Compounds of the invention include compounds of Formula I, or an acid or base addition a salt thereof,

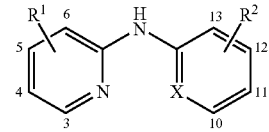

Formula I wherein X is a carbon or nitrogen atom; wherein $R^1$, and $R^2$ are each independently a hydrogen or an electron donating group, but are not both hydrogen; and wherein $R^1$ and $R^2$ are each bonded to a carbon atom within their respective aryl ring;

Formula IA, or an acid or base addition a salt thereof,

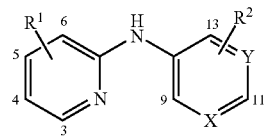

Formula IA wherein each of X and Y are independently a carbon or nitrogen atom, and wherein $R^1$ and $R^2$ are each independently a hydrogen or an electron donating group, but are not both hydrogen, and wherein $R^1$ and $R^2$ are each bonded to a carbon atom within their respective aryl ring.

and/or include Formula IB, or an acid or base addition a salt thereof,

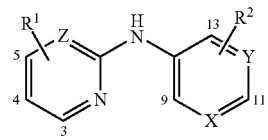

Formula IB wherein each of X, Y and Z are independently a carbon or nitrogen atom; wherein $R^1$, and $R^2$ are each independently a hydrogen or an electron donating group, but are not both hydrogen; and wherein $R^1$ and $R^2$ are each bonded to a carbon atom within their respective aryl ring Compounds of the invention also include compounds of Formula II, or an acid or base addition a salt thereof,

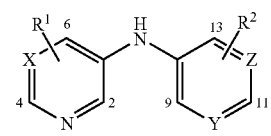

Formula II wherein each of X, Y, and Z are independently a carbon or nitrogen atom, wherein $R^1$, and $R^2$ are each independently a hydrogen or an electron donating group, but are not both hydrogen, and wherein $R^1$ and $R^2$ are each bonded to a carbon atom within their respective aryl ring.

In some embodiments compounds of the invention do not include $N^1,N^1$-dimethyl-$N^4$-(3-pyridyl)phenylenediamine. In some embodiments compounds of the invention do not include N-(3-pyridyl)-3-methylaniline. In some embodiment compounds of the invention do not include either $N^1,N^1$-dimethyl-$N^4$-(3-pyridyl)phenylenediamine or N-(3-pyridyl)-3-methylaniline. In some embodiments compounds of the invention are those of Formula II where X, Y, and Z are all carbons, $R^1$ is a hydrogen and $R^2$ is an electron donating group, but is not a methyl group or a dimethylamine.

In some embodiments of Formula I, Formula IA, Formula IB and/or Formula II, $R^2$ is a hydrogen and $R^1$ is an electron donating group. In some embodiments $R^1$ is a hydrogen and $R^2$ is an electron donating group. In some embodiments, both $R^1$ and $R^2$ are electron donating groups and the $R^1$ and $R^2$ electron donating groups are the same. In other embodiments both $R^1$ and $R^2$ are electron donating groups and the $R^1$ and $R^2$ electron donating groups are different. In some embodiments, at least one electron donating group is a hydrocarbon group. In some embodiments the hydrocarbon group is a saturated or unsaturated, branched or straight chain hydrocarbon moiety. In some embodiments, the hydrocarbon group is aliphatic. In some embodiments the hydrocarbon group is a saturated or unsaturated, branched or straight chain hydrocarbon moiety covalently linked to one or more aromatic hydrocarbons. In other embodiments, the hydrocarbon group is a saturated or unsaturated, branched or straight chain hydrocarbon moiety covalently linked to a cycloaliphatic group. In other embodiments the hydrocarbon group is a saturated or unsaturated, branched or straight chain hydrocarbon moiety covalently linked to one or more aromatic hydrocarbons and/or one or more cycloaliphatic groups. In yet other embodiments, $R^1$ and/or $R^2$ is one or more cycloaliphatic groups. In yet other embodiments, $R^1$ and/or $R^2$ is one or more aromatic hydrocarbons. In yet other embodiments, and/or $R^2$ is one or more cycloaliphatic groups covalently linked to one or more aromatic hydrocarbons (or vice versa). In yet other embodiments, $R^1$ is a hydrogen and $R^2$ is a hydrocarbon group which is not a methyl group. In yet other embodiments, $R^1$ is a hydrogen and $R^2$ is a hydrocarbon group which is not a dimethylamine group.

In some embodiments of Formula I, Formula IA, Formula IB and/or Formula II, the electron donating group is an alkoxy group ($OR^3$). In some embodiments, the $R^3$ group is a hydrogen. In some embodiments the $R^3$ is a hydrocarbon group and in some embodiments is a saturated or unsaturated, branched or straight chain hydrocarbon moiety. In other embodiments $R^3$ is a saturated or unsaturated, branched or straight chain hydrocarbon moiety covalently linked to one or more aromatic hydrocarbons. In other embodiments, $R^3$ is a saturated or unsaturated, branched or straight chain hydrocarbon moiety covalently linked to a cycloaliphatic group. In other embodiments $R^3$ is a saturated or unsaturated, branched or straight chain hydrocarbon moiety covalently linked to one or more aromatic hydrocarbons and/or one or more cycloaliphatic groups. In yet other embodiments, $R^3$ is one or more cycloaliphatic groups. In yet other embodiments, $R^3$ is one or more aromatic hydrocarbons. In yet other embodiments, $R^3$ is one or more cycloaliphatic groups covalently linked to one or more aromatic hydrocarbons (or vice versa).

In some embodiments of Formula I, Formula IA, Formula IB and/or Formula II, at least one electron donating group is an amine group ($NR^4R^5$). In some embodiment $R^4$ and $R^5$ cannot both be hydrogen. In other embodiments $R^4$ is a hydrogen and $R^5$ is an electron donating group. In other embodiments $R^4$ is an electron donating group and $R^5$ is a hydrogen. In other embodiments both $R^4$ and $R^5$ are both electron donating groups. In other embodiments both $R^4$ and $R^5$ are hydrogens. In some embodiments, $R^4$ and/or $R^5$ is a saturated or unsaturated, branched or straight chain hydrocarbon moiety. In other embodiments $R^4$ and/or $R^5$ is a saturated or unsaturated, branched or straight chain hydrocarbon moiety covalently linked to one or more aromatic hydrocarbons. In other embodiments, $R^4$ and/or $R^5$ is a saturated or unsaturated, branched or straight chain hydrocarbon moiety covalently linked to a cycloaliphatic group. In other embodiments $R^4$ and/or $R^5$ is a saturated or unsaturated, branched or straight chain hydrocarbon moiety covalently linked to one or more aromatic hydrocarbons and/or one or more cycloaliphatic groups. In yet other embodiments, $R^4$ and/or $R^5$ is one or more cycloaliphatic groups. In yet other embodiments, $R^4$ and/or $R^5$ is one or more aromatic hydrocarbons. In yet other embodiments, $R^4$ and/or $R^5$ is one or more cycloaliphatic groups covalently linked to one or more aromatic hydrocarbons (or vice versa). In yet other embodiments, when $R^1$ is a hydrogen and $R^4$ and $R^5$ are not both a methyl group.

The Substituent $R^1$ in Formula I, Formula IA, and/or Formula IB is bonded to a carbon atom at any one of positions 3, 4, 5, or 6. In another embodiment $R^1$ is bonded to a carbon atom at any one of positions 4, 5, or 6. In yet another embodiment $R^1$ is bonded to a carbon atom at position 4 or 6. In yet another embodiment $R^1$ is bonded to a carbon atom at position 3. In yet another embodiment $R^1$ is bonded to a carbon atom at position 4. In yet another embodiment $R^1$ is bonded to a carbon atom at position 5. In yet another embodiment $R^1$ is bonded to a carbon atom at position 6. Similarly, $R^2$ is bonded to a carbon atom at any one of positions 9, 10, 11, 12 or 13. In another embodiment $R^2$ is bonded to a carbon atom at any one of positions 10, 11, or 12. In another embodiment $R^2$ is bonded to a carbon atom at any one of positions 9 or 13. In another embodiment $R^2$ is bonded to a carbon atom at any one of positions 10 or 12. In another embodiment $R^2$ is bonded to a carbon atom at position 9. In yet another embodiment $R^2$ is bonded to a carbon atom at position 10. In another embodiment $R^2$ is bonded to a carbon atom at position 11. In another embodiment $R^2$ is bonded to a carbon atom at position 12. In another embodiment $R^2$ is bonded to a carbon atom at position 13.

The Substituent $R^1$ in Formula II is bonded to a carbon atom at any one of positions 2, 4, 5, or 6. In another embodiment $R^1$ is bonded to a carbon atom at any one of positions 4, 5, or 6. In yet another embodiment $R^1$ is bonded to a carbon atom at position 4 or 6. In yet another embodiment $R^1$ is bonded to a carbon atom at position 4. In yet another embodiment $R^1$ is bonded to a carbon atom at position 5. In yet another embodiment $R^1$ is bonded to a carbon atom at position 6. Similarly, $R^2$ is bonded to a carbon atom at any one of positions 9, 10, 11, 12 or 13. In another embodiment $R^2$ is bonded to a carbon atom at any one of positions 10, 11, or 12. In another embodiment $R^2$ is bonded to a carbon atom at any one of positions 9 or 13. In another embodiment $R^2$ is bonded to a carbon atom at any one of positions 10 or 12. In another embodiment $R^2$ is bonded to a carbon atom at any one of position 9. In yet another embodiment $R^2$ is bonded to a carbon atom at position 10. In another embodiment $R^2$ is bonded to a carbon atom at position 11. In another embodiment $R^2$ is bonded to a carbon atom at position 12. In another embodiment $R^2$ is bonded to a carbon atom at position 13.

Useful compounds include those of Formula II, wherein one or more selected atoms within one or both of the aryl rings are nitrogen. In particular, compounds of the invention include compounds wherein there is a nitrogen atom at either position 3 or position 5 of Formula II. Compounds of the invention also include compounds where there is a nitrogen atom at both positions 3 and 5 of Formula II. Compounds of the invention also include compounds wherein there is a nitrogen atom at positions 3 and 10 of Formula II. Compounds of the invention also include compounds wherein there is a nitrogen atom at positions 3 and 12 of Formula II. In another embodiment, compounds of the invention include compounds wherein there is a nitrogen atom at positions 3, 5, and 10 of Formula II. In another embodiment, compounds of the invention include compounds wherein there is a nitrogen atom at positions 3, 5, and 12 of Formula II. In another embodiment, compounds of the invention include compounds wherein there is a nitrogen atom at positions 3, 5, 10 and 12 of Formula II. In another embodiment, compounds are those wherein X, Y, and Z are each nitrogen. In another embodiment, compounds are those wherein X is nitrogen, and Y and Z are carbon. In another embodiment, compounds are those wherein X and Y are nitrogen and Z is carbon. In another embodiment, compounds are those wherein Y is nitrogen, and X and Z are carbon. In another embodiment, compounds are those wherein Y and Z are nitrogen, and X is carbon.

Compounds of the invention also encompass those of Formula II wherein $R^1$ and $R^2$ are each independently:
 (i) a hydrogen;
 (ii) a $C_2$ to $C_{20}$ hydrocarbon group;
 (iii) $OR^3$ wherein $R^3$ is a hydrogen or a $C_1$ to $C_{20}$ hydrocarbon group; or
 (iv) $NR^4R^5$ wherein $R^4$ and $R^5$ are each independently hydrogen or a $C_2$ to $C_{20}$ hydrocarbon group; and
wherein $R^1$ and $R^2$ are not both hydrogen.

Compounds of the invention also encompass those of Formula II wherein $R^1$ and $R^2$ are each independently:
 (i) a hydrogen;
 (ii) a $C_1$ to $C_{20}$ hydrocarbon group;
 (iii) $OR^3$ wherein $R^3$ is a hydrogen or a $C_1$ to $C_{20}$ hydrocarbon group; or
 (iv) $NR^4R^5$ wherein $R^4$ and $R^5$ are each independently hydrogen or a $C_1$ to $C_{20}$ hydrocarbon group; and
wherein $R^1$ and $R^2$ are not both hydrogen.

In another embodiment, compounds are those of Formula II wherein $R^1$ is attached to a carbon at position 2 or 6, and is:
 (i) a hydrogen;
 (ii) a $C_1$ to $C_3$ hydrocarbon group;
 (iii) $OR^3$ wherein $R^3$ is a hydrogen or a $C_1$ to $C_3$ hydrocarbon group; or
 (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In another embodiment, compounds are those of Formula II wherein $R^2$ is attached to a carbon at position 9 or 13, and is:
 (i) a hydrogen;
 (ii) a $C_1$ to $C_3$ hydrocarbon group;
 (iii) $OR^3$ wherein $R^3$ is a hydrogen or a $C_1$ to $C_3$ hydrocarbon group; or
 (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In another embodiment, compounds are those of Formula II wherein $R^1$ is attached to a carbon at position 5, and is:
 (i) a hydrogen;
 (ii) a $C_1$ to $C_{20}$ hydrocarbon group;
 (iii) $OR^3$ wherein $R^3$ is a hydrogen or a $C_1$ to $C_{20}$ hydrocarbon group; or
 (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^2$ is attached to a carbon at position 10 or 12, and is:
 (i) a hydrogen;
 (ii) a $C_1$ to $C_{20}$ hydrocarbon group;
 (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^1$ is attached to a carbon at position 4, and is:
(i) a hydrogen;
(ii) a $C_1$ to $C_{20}$ hydrocarbon group;
(iii) $OR^3$ wherein $R^3$ is a hydrogen or a $C_1$ to $C_{20}$ hydrocarbon group; or
(iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^2$ is attached to a carbon at position 11, and is:
(i) a hydrogen;
(ii) a $C_1$ to $C_{20}$ hydrocarbon group;
(iii) $OR^3$ wherein $R^3$ is a hydrogen or a $C_1$ to $C_{20}$ hydrocarbon group; or
(iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In some embodiments, $R^4$ and $R^5$ are not both hydrogen. In some embodiments $R^3$ is not hydrogen. In some embodiments none of $R^3$, $R^4$, or $R^5$ are hydrogen.

Formulations and Applications

One or more compounds of the invention may be combined with one or more organic substrates to form compositions wherein the compounds of the invention assist in protecting the organic substrate from oxidative degradation.

Therefore, one or more compounds of the invention are combined with one or more organic substrates to form compositions wherein the one or more compounds are added in an effective amount to ensure sufficient antioxidant activity to reduce or inhibit the level of degradation of the organic substrate(s) within the composition when compared with the level of degradation that occurs to the organic substrate in the absence of the compound of the invention.

One or more compounds of the invention may also be combined with one or more organic substrates to scavenge free radicals in a composition containing the organic substrate(s). Therefore, one or more compounds of the invention are combined with one or more organic substrates, wherein the one or more compounds are added in an effective amount to ensure an amount sufficient to scavenge at least one free radical species which may exist, or be formed in the composition.

One or more compounds of the invention may also be combined with compounds required for the synthesis of an organic substrate such as a polymer. The compounds required for the synthesis can include organic substrates themselves, for example monomers which will react to form a polymer. The one or more compounds of the invention are useful in scavenging at least one free radical species which may exist or be formed by the monomers, and therefore may improve the yield, stability and/or longevity of the organic substrate and/or the monomers which form the polymer.

One or more compounds of the invention are added, blended, sprayed, adhered, used to cover, impregnate or are otherwise combined with one or more organic substrates to form compositions of the invention.

In some embodiments, compounds of the invention are added to organic substrates which are natural or synthetic polymers such as alpha-olefin polymers, polyamides, polyesters, polyacetals, acrylonitrile-butadiene-styrene thermoplastics, and other resin or rubber polymers to protect the polymers against excessive breakdown during the synthesis, aging, and/or heat treatment involved in the making or use.

One or more compounds of the invention, for example, can be added during the synthesis of one or more polymers and preferentially react with, and/or decompose free radicals that are generated during the synthesis of a polymer to thereby prevent or reduce activities which prevent effective polymerization and/or degradation during the preparation of the polymer. Addition of antioxidants to one or more polymers during the preparation and/or use is well known in the art. See for example U.S. Pat. No. 2,543,329 which describes the stabilization of polyethylene with diphenylamine; U.S. Pat. No. 3,072,603 describes the stabilization of poly-alpha-olefins by use of a stabilizer combination consisting of a diester of 3,3'-thiodipropionic acid and para substituted diphenylamines which contain alkyl group substitutions of $C_1$ to $C_{12}$ in length. Both U.S. Pat. No. 2,543,329 and U.S. Pat. No. 3,072,603, without adopting any definitions as found therein, are incorporated herein by reference.

In other embodiments, compounds of the invention are added to organic substrates which are typically used in the cosmetic and/or pharmaceutical industry including those oils, fats and/or waxes comprised of esters of saturated and/or monounsaturated and/or polyunsaturated fatty acids, including the unsaponifiable fractions obtained from such oils, fats and waxes so as to scavenge free radicals that may exist or be formed in the preparation or use of the cosmetic and/or pharmaceutical product. See for example U.S. Pat. No. 5,672,574 as well as a description of the type of lipids used for this applications as described in Rabasco Alvarez, A. M., and Gonzalez Rodriguez, M. L. "Lipids in pharmaceutical and cosmetic preparations" Grases y Aceites Vol. 51, Fasc. 1-2 (2000) 74-96.

The compounds of the invention are particularly suited to being used as both antioxidants and inhibitors of radical polymerization to stabilize unsaturated monomers used in the preparation of polymers because of their ability to trap both peroxyl (ROO·) radicals that mediate autoxidation of the monomer and alkyl radicals (R·) that mediate polymerization (see Example 14).

In other embodiments, compounds of the invention are added to organic substrates such as biomass derived fuel components (biodiesel fuel) as an antioxidant to prevent oxidative degradation. Biodiesels include a variety of ester-based oxygenated fuels made from vegetable oils, fats, greases, or other sources of triglycerides. They are nontoxic and biodegradable substitute and supplement for petroleum diesel. Organic fuels, such as biodiesel, often include a wide variety of contaminants such that stability, especially by oxidative degradation, is a serious problem in these fuels, and such degradation often leads to gummy decomposition products. The use of traditional substituted diphenylamines, alone or in mixtures with other materials, as an additive to biodiesel fuels to reduce oxidative degradation is well known in the art. See, for example, U.S. Pat. No. 3,322,520, U.S. Pat. No. 3,556,748; U.S. Pat. No. 5,509,944, and U.S. Pat. No. 5,169,410 all of which, without adopting any definitions as found therein, are incorporated herein by reference.

Thus, encompassed within the scope of the invention are compositions of biodiesel fuels with one or more substituted diarylamines of the current invention wherein one or more of the ring atoms in one or both aryl groups are nitrogen. More particularly, in certain embodiments one or more of the atom(s) at the meta positions relative to the amine are nitrogen.

In some embodiments, the compounds of the invention are used in conjunction with a lubricant or fuel to form a lubricating composition. In some embodiments, the lubricant includes a natural and/or a synthetic oil, oil derived from hydrocracking, hydrogenation, hydrofinishing, unrefined, refined and re-refined oils, and mixtures thereof, the lubricant having a viscosity appropriate for the particular lubricant application. In some embodiments the lubricating composition is useful as a crankcase lubricant. In other embodiments, the lubricating composition is useful for engines such as gasoline powered engines and diesel engines. In other embodiments, the lubricating composition is one which is conventionally employed in and/or adapted for use as power transmitting fluid such as automatic transmission fluids, tractor fluids, universal tractor fluids and hydraulic fluids, heavy duty hydraulic fluids, power steering fluids and the like. In yet other embodiments, gear lubricants, industrial oils, pump oils and other lubricating oil compositions can also benefit from the incorporation therein of one or more of the compositions of the present invention.

The organic substrate can be present within the composition in an amount greater than about 40% by weight, greater than about 50% by weight, greater than about 60% by weight, greater than about 70%, greater than about 75% by weight, greater than about 80% by weight, greater than 85% by weight or greater than 90% by weight.

In some embodiments, the composition may further comprise one or more other antioxidants combined with one or more of the antioxidants of the current invention. In some embodiments the one or more other antioxidants include sterically hindered phenols. In some embodiments, the composition may further comprise other additives well known in the art. For example, "additives" as used herein in reference to viscosity improving materials, anti-wear agents, zinc salts, anti-deposition agents, hydrolytic stabilizers, friction modifiers, seal swell agents, anti-rust agents, foam suppressing agents, or pour point depressants.

Kits

In some embodiments, kits can be produced and distributed which incorporate one or more of the compounds of the invention along with instructions for use.

Kits may be generated and comprise one or more antioxidant compounds as described herein along with instructions for use as an antioxidant. In one embodiment the instructions describe the means to prevent or reduce degradation of the organic substrate during storage, handling or use. Such kits may additionally comprise one or more "additives" including viscosity improving materials, anti-wear agents, zinc salts, anti-deposition agents, hydrolytic stabilizers, friction modifiers, seal swell agents, anti-rust agents, foam suppressing agents, or pour point depressants. Such kits may also comprise one or more traditional antioxidants in combination with one or more compounds of the invention. In one embodiment, one or more traditional antioxidants include sterically hindered phenols.

Kits may also be generated and comprise one or more antioxidant compounds along with instructions for use of the compound(s) as an additive during synthesis of one or more organic substrates, to improve the stability or yield of the organic substrate during synthesis. Such kits may additionally comprise one or more monomers, dimers or trimers and appropriate solvents and/or buffers suitable for such synthesis of polymers from said monomers, dimers or trimers.

EXAMPLES

The following examples are given for illustrative purposes and are not intended to be limiting to the invention as disclosed herein.

In order to identify particularly promising candidates, we carried out a series of computational studies employing quantum chemical methods at the B3LYP level of density functional theory. Specifically, we calculated the theoretical activation enthalpies ($\Delta H^{\ddagger}$) for the reactions of a variety of proposed substituted diarylamines with peroxyl radicals (using methylperoxyl as a model autoxidation chain-carrying peroxyl radicals, ROO·) and compared them to the ionization enthalpies ($\Delta H_{Ion}$) of these diarylamines, to identify candidates that are particularly adept at the formal H-atom transfer reaction, but relatively stable to electron transfer reactions. For ease of reference, compounds have been numbered. Prior art compounds are noted as such.

Example 1A Calculating Theoretical Ionization and Activation Enthalpies of Selected Unsubstituted Diarylamines Ionization enthalpies and activitation enthalpies for reactions with peroxyl radicals were calculated for unsubstituted diarylamines as described above. The results of these calculations are show in Table 1A.

Table 1A. Calculated Theoretical Ionization Enthalpies and Activation Enthalpies for the Reactions with Peroxyl Radicals of Some Unsubstituted Diarylamines. All values in kcal/mol at 298 K. Compound 1 is prior art. Compound 2 through 6 are compounds without substitutions. Data is shown for $\Delta H_{Ion}$ and $\Delta H^{\ddagger}$, and incremental changes in the $\Delta H_{Ion}$ and $\Delta H^{\ddagger}$ for each compound as compared with compound 1 is shown in brackets.

TABLE 1A

| Amine | $\Delta H_{ion}$ | $\Delta H^{\ddagger}$ |
|---|---|---|
| 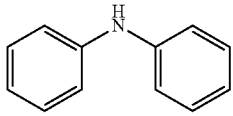 [SMILES: c1ccc(Nc2ccccc2)cc1] | 1 160.5 (0.0) | 1.58 (0.00) |
| 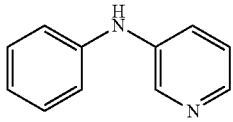 [SMILES: c1ccc(Nc2cccnc2)cc1] | 2 166.1 (5.6) | 1.85 (0.27) |
| 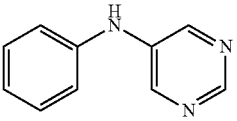 [SMILES: c1ccc(Nc2cncnc2)cc1] | 3 172.1 (11.6) | 1.98 (0.40) |
| 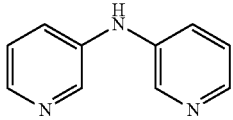 [SMILES: c1cncc(Nc2cccnc2)c1] | 4 172.0 (11.5) | 2.35 (0.77) |
| 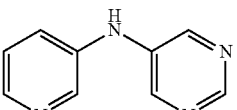 | 5 178.4 (17.9) | 2.59 (1.01) |
| 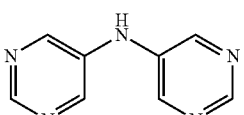 | 6 185.2 (24.7) | 2.85 (1.27) |

The calculations on the unsubstituted compounds also reveal that the incorporation of each N into a diphenylamine increases $\Delta H_{Ion}$ by roughly 6 kcal/mol and $\Delta H^{\ddagger}$ by roughly a third of a kcal/mol. Indeed, while the incorporation of even 4 nitrogen atoms increases the ionization enthalpy by more than 24.7 kcal/mol, the barrier to the reaction with peroxyls is predicted to increase by less than 1.3 kcal/mol.

Example 1B—Calculating Theoretical N—H Bond Dissociation Enthalpies (BDE) and Ionization Potential (IP) of Unsubstituted Diarylamines Quantum chemical calculations using the complete basis set approach at the CBS-QB3 level (Montgomery, J. A.; Frisch, M. J.; Ochterski, J. W.; Petersson, G. A. *J. Chem. Phys.* 1999, 110, 2822) were carried out in order to predict the effects that heteroatom incorporation would have on the N—H BDE and IP of diphenylamine. All of the possible positions of attachment of either a pyridine or pyrimidine ring to the diphenylamine nitrogen in place of one of the phenyl rings were considered (Table 1B). The incorporation of each of the 2-, 3- and 4-pyridyl substituents resulted in increases in both the calculated N—H BDE and the IP, with the 2-pyridyl substituent giving rise to the largest increase in BDE (+3.7 kcal/mol), but the smallest increase in IP (+2.7 kcal/mol). The largest increase in IP was predicted for the 4-pyridyl substituent (+10 kcal/mol), which was accompanied by an increase in the BDE of 2.5 kcal/mol. The best compromise between a negligible effect on BDE (0.4 kcal/mol), but significant increase in IP (6.4 kcal/mol) was predicted for the 3-pyridyl substituent. The same trends were predicted when each of 2-, 4- and 5-pyrimidyl substituents were incorporated in place of one of the phenyl rings.

The results herein make it clear that incorporation of nitrogen atoms at the 3 and 5 positions strikes the best compromise between maximally increasing the IP while minimally increasing the N—H BDE. Since both phenyl rings in diphenylamine could be replaced with pyridyl and/or pyrimidyl rings, we expanded our calculations to include the corresponding dipyridylamines and dipyrimidylamines as well as the unsymmetric pyridyl pyrimidyl amines (Table 2). The results suggest that the N—H BDEs in diarylamines are almost invariant with nitrogen incorporation at the 3 and/or 5 positions relative to the amine nitrogen (predicted to be within 0.6 kcal/mol of each other), and that ionization potentials increase systematically by roughly 6 kcal/mol per nitrogen atom.

TABLE 1B

| Structure | BDE | IP |
|---|---|---|
| diphenylamine | 86.4 | 168.3 |
| N-phenyl-2-pyridylamine | 90.1 | 171.0 |
| N-phenyl-3-pyridylamine | 86.8 | 174.7 |
| N-phenyl-4-pyridylamine | 88.9 | 178.3 |
| diphenylamine | 86.4 | 168.3 |
| N-phenyl-2-pyrimidylamine | 96.0 | 175.4 |
| N-phenyl-5-pyrimidylamine | 86.4 | 179.3 |
| N-phenyl-4-pyrimidylamine | 92.8 | 181.0 |

In Table 1B, calculated (CBS-QB3) gas phase N—H bond dissociation enthalpies (BDEs) and ionization potentials (IPs) are as shown for a series of heteroatom-containing diphenylamines in kcal/mol.

TABLE 1C

| Structure | BDE | IP |
|---|---|---|
| diphenylamine | 86.4 | 168.3 |
| N-phenyl-3-pyridylamine | 86.8 | 174.7 |
| di(3-pyridyl)amine | 87.0 | 180.2 |
| N-phenyl-5-pyrimidylamine | 86.4 | 179.3 |
| N-(3-pyridyl)-5-pyrimidylamine | 86.6 | 186.0 |

TABLE 1C-continued

| Structure | BDE | IP |
|---|---|---|
| 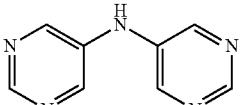 | 86.5 | 193.0 |

Table 1C Calculated (CBS-QB3) gas phase N—H bond dissociation enthalpies (BDEs) and ionization potentials (IPs) for a series of diphenylamines incorporating heteroatoms at the 3- and 5-positions in kcal/mol.

Example 2—Calculating Theoretical Ionization and Activation Enthalpies of Selected Monosubstituted and Disubstituted Diarylamines Various substitutions affect both $\Delta H_{Ion}$, and $\Delta H^{\ddagger}$ were tested. To provide a basis for comparison compound 7 (prior art) was used as a model to demonstrate the typical reactivity of a 4,4'-dialkylated diphenylamine. This sets a target for the design of compounds with comparable $\Delta H^{Ion}$, but lower $\Delta H^{\ddagger}$. Incremental changes in the $\Delta H_{Ion}$ and $\Delta H^{\ddagger}$ for compound 7 as compared with compound 1 are shown in brackets.

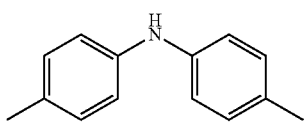

7

$\Delta H_{ion} = 153.0 \, (-7.5)$
$\Delta H_{act} = 0.13 \, (-1.45)$

The N,N-dimethylamino substituent group was compared with substituted diarylamines containing one or two of the N,N-dimethylamino substituent group on each of the symmetric and asymmetric diarylamines in the para position relative to the reactive amine N—H. The results are shown in Tables 2 and Table 3 respectively. Incremental changes in the $\Delta H_{Ion}$ and $\Delta H^{\ddagger}$ for each compound as compared with compound 1 are shown in brackets Table 2. Calculated Ionization Enthalpies and Activation Enthalpies for the Reactions with Peroxyl Radicals of Some Monosubstituted Diarylamines. Data is shown for $\Delta H_{Ion}$ and $\Delta H^{\ddagger}$, and incremental changes in the $\Delta H_{Ion}$ and $\Delta H^{\ddagger}$ for each compound as compared with compound 1 is shown in brackets. All values are indicated in kcal/mol at 298 K.

TABLE 2

| | Amine | | $\Delta H^{ion}$ | $\Delta H^{\ddagger}$ |
|---|---|---|---|---|
| 8 | 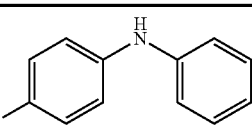 | | 139.0 (−21.5) | −3.10 (−4.68) |
| 9 | 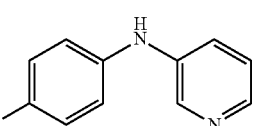 | | 142.9 (−17.6) | −3.09 (−4.67) |

TABLE 2-continued

| | Amine | $\Delta H^{ion}$ | $\Delta H^{\ddagger}$ |
|---|---|---|---|
| 10 | 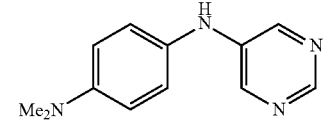 [SMILES: CN(C)c1ccc(Nc2cncnc2)cn1] | 147.2 (−13.3) | −2.95 (−4.53) |
| 11 | 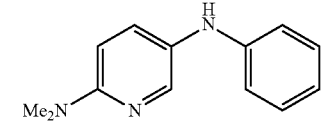 [SMILES: CN(C)c1ncc(Nc2ccccc2)cn1] | 143.7 (−16.8) | −2.69 (−4.27) |
| 12 | 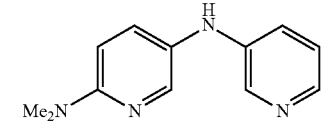 [SMILES: CN(C)c1ncc(Nc2cccnc2)cn1] | 147.8 (−12.7) | −2.62 (−4.20) |
| 13 | 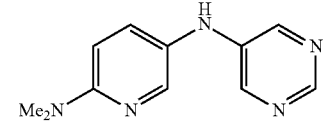 | 152.3 (−8.2) | −2.37 (−3.95) |
| 14 | 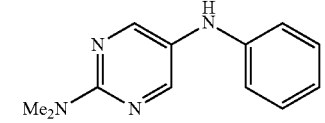 | 149.5 (−11.0) | −2.29 (−3.87) |
| 15 | 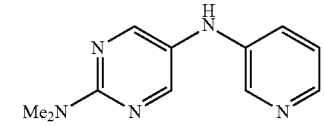 | 154.0 (−6.5) | −1.97 (−3.55) |
| 16 | 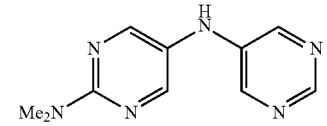 | 158.7 (−1.8) | −1.69 (−3.27) |

In the monosubstituted diarylamines 8-16, the ionization enthalpy increases by approx. 4-5 kcal/mol per nitrogen. The incremental margin is smaller than for the unsubstituted diarylamines since the ring is already quite electron rich. Interestingly, we note that there is a preference for the interaction of the peroxyl radical with the most electron rich of the two aromatic rings. For example, on comparing amines 8, 9 and 10, the ionization enthalpy increases 3.9 and 4.2 kcal/mol upon incorporation of the first and second nitrogen, respectively, into one of the aromatic rings, while the activation enthalpy is essentially the same in each case. Similarly, on comparing amines 11, 12 and 13, the ionization enthalpies increases 4.1 and 4.5 kcal/mol for incorporation of one and two nitrogens into one of the aromatic rings, while the activation enthalpy increases by 0.1 and 0.3 kcal/mol, respectively. Consideration of the last trio of 14, 15 and 16 reveals increases in ionization enthalpy of 4.5 and 4.7 kcal/mol for each nitrogen and 0.3 and 0.6 kcal/mol in activation enthalpy for each nitrogen. Overall, in going from the monosubstituted diphenylamine to dipyrimidylamine, the ionization enthalpy increases 19.7 kcal/mol and the enthalpy of activation only 1.4 kcal/mol.

Table 3. Calculated Theoretical Ionization and Activation Enthalpies for the Reactions with Peroxyl Radicals of Some Disubstituted Diarylamines. Data is shown for $\Delta H_{Ion}$, and $\Delta H^{\ddagger}$, and incremental changes in the $\Delta H_{Ion}$, and $\Delta H^{\ddagger}$ for each compound as compared with compound 1 is shown in brackets. All values in kcal/mol at 298 K.

TABLE 3

| Amine | | $\Delta H^{ion}$ | $\Delta H^{\ddagger}$ |
|---|---|---|---|
| (structure: 4,4'-bis(dimethylamino)diphenylamine) | 17 | 126.8 (−33.7) | −5.67 (−7.25) |
| (structure: mixed phenyl-pyridyl diarylamine) | 18 | 130.2 (−30.3) | −5.57 (−7.15) |
| (structure: phenyl-pyrimidyl diarylamine) | 19 | 134.0 (−26.5) | −5.55 (−7.13) |
| (structure: dipyridyl diarylamine) | 20 | 133.7 (−28.8) | −5.57 (−7.15) |
| (structure: pyridyl-pyrimidyl diarylamine) | 21 | 137.8 (−22.7) | −5.34 (−6.92) |
| (structure: dipyrimidyl diarylamine) | 22 | 142.4 (−18.1) | −5.13 (−6.71) |

Again, the introduction of nitrogen in the aromatic rings of the diarylamines leads to fairly systematic changes in both ionization enthalpies and activation enthalpies. For example, in going from compound 17 to 18 to 19 the ionization enthalpy increases by 3.4 and then 3.8 kcal/mol, respectively, while the activation enthalpy increases by 0.1 and 0 kcal/mol. On comparing 18 to 20 to 21, the ionization enthalpy increases by 3.5 and 4.1, but now the activation enthalpy increases by 0 and 0.2 kcal/mol. Finally, in going from 19 to 21 to 22, the ionization enthalpy increases by 3.8 and 4.6 kcal/mol with the first and second nitrogens, respectively, and the activation enthalpy by 0.2 and 0.2 kcal/mol, respectively. Overall, the ionization enthalpy and activation enthalpy increase by 15.6 and 0.6 kcal/mol, respectively on going from the disubstituted diphenylamine to the disubstituted dipyrimidylamine.

Example 3—Typical Preparation of Diarylamines

Synthesis of selected substituted diarylamines of embodiments of the invention were undertaken so as to be able to study and compare the reactivities of these compounds to peroxyl radicals, as well as determine and compare their oxidation potentials. Similar synthesis strategies were applied using both pyridyl groups ($RC_5H_4N$) and/or pyrimidyl groups ($RC_4H_3N_2$). When either is appropriate, it is described throughout as pyri(mi)dyl or pyr(im)idyl.

The synthetic strategy used was straightforward and used contemporary Pd-catalyzed C—N cross-coupling techniques. For example, to an oven-dried schlenk flask was added $Pd_2(dba)_3$ or $(\eta^3\text{-}1\text{-}PhC_3H_4)(\eta^5\text{-}C_5H_5)$ (0.02 mmol) and XPhos (0.04 mmol). Under an argon atmosphere, dry, degassed toluene (2 mL) was added and the resulting solution heated to 60° C. for 15 minutes. The selected Pyr(im)idyl amine (1.2 mmol) was then added, followed by a selected pyri(mi)dyl bromide (1.0 mmol) and NaOtBu (1.4 mmol). The temperature was then raised to 90° C. and reaction was monitored by thin layer chromatography (TLC) until completion. The reaction mixture was then cooled to room temperature and filtered through celite. Column chromatography using silica gel with hexanes/EtOAc afforded pure diarylamines.

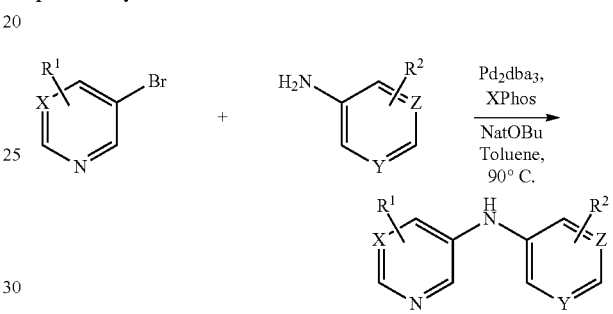

Example 4—Typical Preparation of Arylamines

Pyri(mi)dyl bromides bearing alkoxy (—OR) or dialkylamino (—$NR_2$) substitution are best converted to the corresponding amines using the two-step benzylamination/hydrogenolysis sequence as described in Pratt et al. (Nara, S. J.; Jha, M.; Brinkhorst, J.; Zemanek, T. J.; Pratt, D. A. *J. Org. Chem.* 2008, 73, 9326). For example, to an oven-dried schlenk flask was added the aryl bromide (1.0 mmol), CuI (0.2 mmol), L-proline (0.4 mmol) and $K_2CO_3$ (1.5 mmol). The flask was evacuated and backfilled with argon. Degassed dimethyl sulfoxide (DMSO) (1.0 mL) was then added and the reaction stirred at room temperature for 5 minutes prior to the addition benzylamine (1.5 mmol). The flask was capped and the reaction mixture heated to 90° C. until completion (monitored by thin layer chromatography (TLC)). Once complete, the reaction mixture was cooled, added to 10 mL of aqueous $NH_4Cl$ and extracted with ether. Purification by column chromatography using silica gel (hexanes/EtOAc) afforded pure N-benzylarylamines. Removal of the benzyl group was achieved in MeOH degassed with argon, via 10% Pd/C (10 wt %) and ammonium formate (5.0 mmol) for 1 mmol of starting material. The solution was heated to reflux and reaction progress was monitored by TLC. Upon completion, the reaction was cooled to room temperature and filtered through celite. The solvent was removed in vacuo and the crude material was redissolved in EtOAc and filtered through celite to obtain material of sufficient purity for use to prepare the diarylamines as described above.

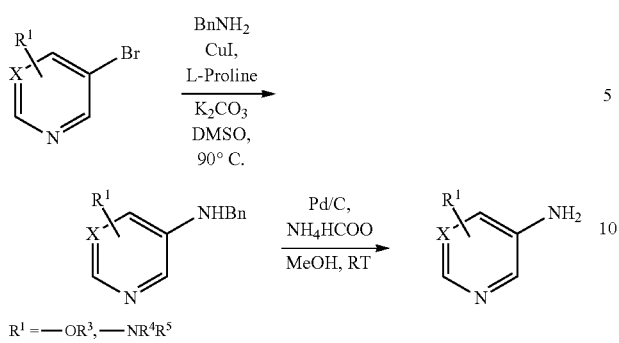

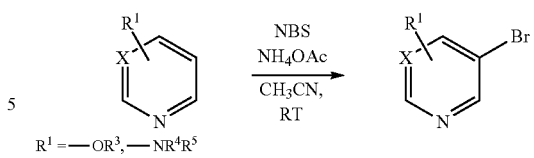

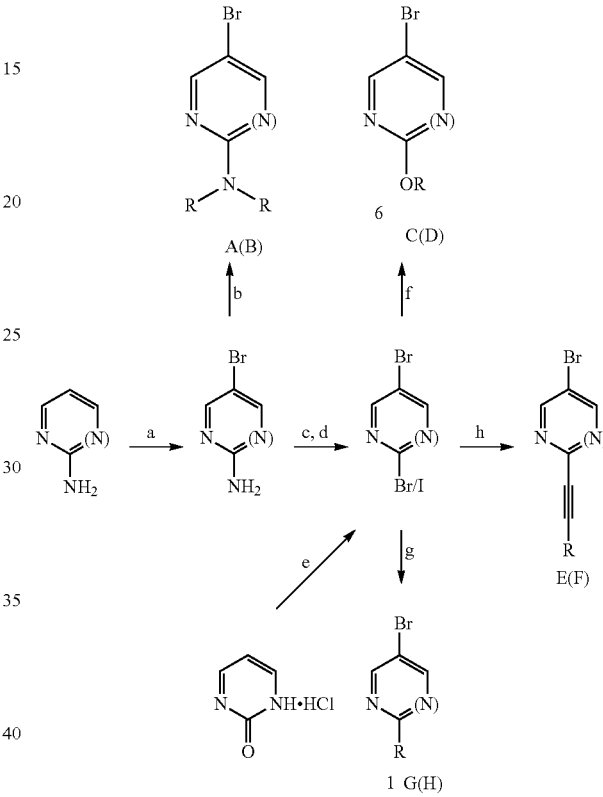

The above conditions were less effective for less electron rich compounds (R=H, alkyl, alkynyl). Increasing catalyst loading, or changing to Pd(OH)$_2$ or Raney Nickel catalyst, did not improve the outcome up to several atmospheres of H$_2$. Instead, unsubstituted pyri(mi)dyl bromides, or those bearing alkyl (—R) substitutions were best converted to the corresponding amines directly using aqueous ammonia as described by Kim and Chang (Kim, J.; Chang, S. *Chem. Commun.* 2008, 3052-3054). For example, to an oven-dried schlenk flask was added the aryl bromide (1.0 mmol), CuI (0.2 mmol), L-proline (0.4 mmol) and K$_2$CO$_3$ (1.5 mmol). The flask was evacuated and backfilled with argon. Degassed DMSO (1.0 mL) was then added and the reaction stirred at room temperature for 5 minutes prior to the addition NH$_4$OH (1.5 mmol). The flask was capped and the reaction mixture heated to 90° C. until completion (monitored by TLC). Once complete, the reaction mixture was cooled, added to 10 mL of aqueous NH$_4$Cl and extracted with ether. Purification by column chromatography using silica gel (hexanes/EtOAc) afforded pure arylamines.

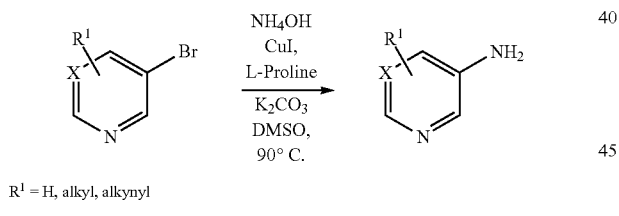

Example 5—Typical Preparation of Aryl Halides

Pyri(mi)dyl bromides were commercially available (e.g. from Sigma Aldrich) (Oakville, Ontario, Canada) or were prepared from commercially available pyridines or pyrimidines (10 mmol) in MeCN (40 mL) at room temperature in the presence of NH$_4$OAc (1.0 mmol) and NBS (10.5 mmol), as suggested by Das and co-workers (Das, B.; Venkatswarlu, K.; Majhi, A.; Siddaiah, V.; Reddy, K. *J. Mol. Cat. A* 2007, 267, 30-33). Reactions were monitored by thin layer chromatography (TLC) and typically were complete within minutes. After removal of acetonitrile in vacuo, water was added (100 mL) and the mixture extracted with EtOAc (3×50 mL). Non aqueous layers were combined and washed with 50 mL brine and dried over MgSO$_4$. Products were used without further purification.

Preparation Scheme of Pyri(mi)dyl Halides-Scheme 1

Scheme 1.
Preparation of relevant pyri(mi)dyl halides A-H. Key: (a) NBS, NH$_4$OAc, MeCN, rt, 5 min, pyr: 85-90%; pym: quant; (b) pyr: RCHO, Na(CN)BH$_3$, MeCN, reflux, 1-12 h (82%, R=C$_5$H$_{11}$); pym: NaH, RI, THF, rt, overnight (85%, R=Me); (c) Me$_3$(Bn)NBr, t-BuONO, CH$_2$Br$_2$, rt, overnight, pyr: 77-83%; pym: 30-40%; (d) pym: H$_1$, CH$_2$Cl$_2$, 0° C., 80-85%; (e) i. NaOH, Br$_2$, H$_2$O, rt, 50-60%, ii. POCl$_3$, PhNEt$_2$, reflux, 4 h, 75-85%, iii. H$_1$, CH$_2$Cl$_2$, 0° C., 80-85%; (f) ROH, Na, rt, 1-12 h, quant.; (g) RZnI, Cl$_2$Pd(PPh$_3$)$_2$, DMF/THF, rt, overnight, pyr (Br): 72% (R=C$_6$H$_{13}$), pym (I) 81%, (R=C$_6$H$_{13}$); (h) alkyne, CuI, Cl$_2$Pd(PPh$_3$)$_2$, Et$_3$N, MeCN, rt, 1-12 h, quant.

Preparation of 3-pyridyl and 5-pyrimidyl halides.
2-Aminopyridine and 2-aminopyrimidine were employed as common starting materials for each of the pyridyl and pyrimidyl halides due to their commercial availability at very low cost. Synthesis of the various pyridyl bromides began with bromination of the 5-position of 2-aminopyridine using NBS/NH$_4$OAc (Das, B.; Venkateswarlu, K.; Majhi, A.; Siddaiah, V.; Reddy, K. R. *J. Mol. Catal, A-Chem.* 2007, 267, 30). This intermediate was either alkylated by reductive amination with appropriate aldehydes to prepare 5-bromo-2-N,N-dialkylaminopyridines (A) or subjected to aqueous (Bhasin, K. K.; Kumar, R.; Mehta, S. K.; Raghavaiah, P.; Jacob, C.; Klapotke, T. M. *Inorg. Chim. Act.* 2009, 362, 2386.) or non-aqueous (Nara, S. J.; Jha, M.; Brinkhorst, J.; Zemanek, T. J.; Pratt, D. A. *J. Org. Chem.* 2008, 73, 9326.) diazotization/halo-dediazoniation to afford 2,5-dibromopyridine. This compound served as the precursor to all other substituted pyridines: 2-alkoxy-5-bromopyridines (C) were obtained by nucleophillic substitution with an appropriate sodium alkoxide17 and 2-alkynyl-5-bromopyridine (E) and 2-alkyl-5-bromopyridines (G) were prepared via Sonogoshira (Tilley, J. W.; Zawoiski, S. *J. Org. Chem.* 1988, 53, 386.) and Negeishi (Getmanenko, Y. A.; Twieg, R. J. *J. Org. Chem.* 2008, 73, 830.) cross-coupling reactions, respectively.

The pyrimidyl bromides were prepared in a similar manner, beginning with bromination of 2-aminopyrimidine. N-Alkylation could not be achieved by reductive amination (presumably due to the decreased nucleophilicity of the amine) and was instead accomplished using NaH and an appropriate alkyl halide to give (B). Non-aqueous diazotization/halo-dediazoniation was used to prepare 5-bromo-2-halopyrimidines, but in diminished yield relative to the analogous reaction with the 2-aminopyridine (again, presumably due to the decreased nucleophilicity of the amine group). Alternatively, 2-pyrimidinone could serve as a precursor to 5-bromo-2-halopyrimidines (Lutz, F.; Kawasaki, T.; Soai, K. *Tetrahedron-Asymmetry* 2006, 17, 486.) or as a substrate for alkylation to generate 5-bromo-2-alkoxypyrimidines (D) (Kokatla, H. P.; Lakshman, M. K. *Org. Lett.* 2010, 12, 4478.) Introduction of an alkyne substituent at the 2-position to give (proceeded satisfactorily under Sonogoshira conditions, but alkylation using Negishi conditions was unselective. Since reduction of the 2-alkynylpyrimidyl bromide (F) to the corresponding 2-alkyl pyrimidyl bromide (H) was complicated by competing removal of the bromine, we turned to 5-bromo-2-iodopyrimidine as a precursor for the cross coupling reactions and saw a dramatic improvement in selectivity and yields.

Example 5B—Alternative Preparation of Pyrimidyl Halides

An alternative for preparation of pyrimidyl halides that has been utilized is shown in Scheme 1B below.

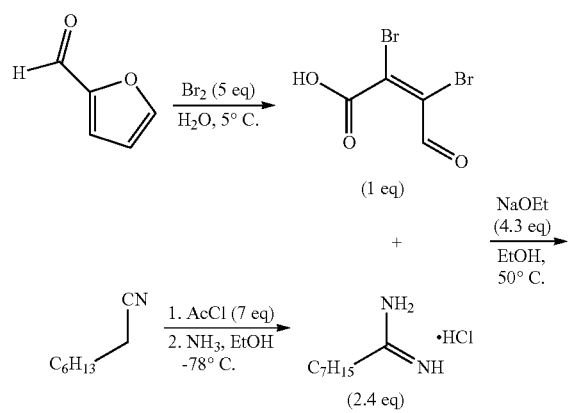

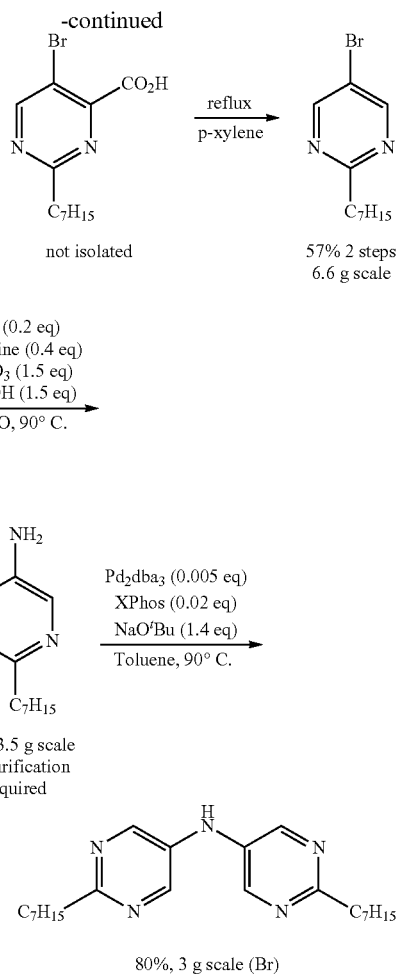

Since the preparation of the pyrimidyl bromides H by the route described in Scheme 1 may not be the most economical solution, we sought an alternative, which is shown in Scheme 1B. The key starting material is furfural, which was brominated in water and then cyclocondensed with an amidine prepared from amination of a nitrile. The resultant product was then decarboxylated on heating to yield the desired product. It is important to note that switching the amidine for an O-alkyl isourea in the cyclocondensation step affords access to the pyrimidyl bromides D, whereas use of an N-alkyl guanidine in the cyclocondensation step affords the pyrimidyl bromides B.]

Example 6 Confirmation of Identity of Selected Compounds

Various compounds used in one or more of the Examples herein were synthesized and the identity of the resulting compound confirmed using $^{1}$H- and $^{13}$C-NMR spectroscopy and high resolution mass spectrometry as noted herein. These compounds include prior art compounds, novel compounds of the invention, compounds used as intermediates in synthesis, and compounds which have been used as controls to demonstrate the utility of the compounds of the invention. While all compounds were synthesized and their identify confirmed by NMR, Confirmation of the identity of only a selection of the synthesized compounds is noted herein in Example 6.

Example 6A N$^1$,N$^1$-dimethyl-N$^4$-(pyridin-3-yl)benzene-1,4-diamine (23)

Compound 23 was previously disclosed in German patent DE 586879 (Maier-Bode, H.), without any recognition of the value of this compound for use as an antioxidant. Compound 23 was prepared in 74% yield from 4-bromo-N,N-dimethylaniline (Aldrich) and 3-aminopyridine (Aldrich) as outlined in Example 3.

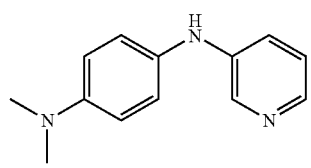

23

$^1$H NMR (CDCl$_3$, 400 MHz) δ ppm 8.22 (d, J=3.2 Hz, 1H), 8.03 (d, J=5.6 Hz, 1H), 7.16-7.07 (m, 4H), 6.76 (d, J=11.6 Hz, 2H), 5.57 (bs, 1H), 2.95 (s, 6H). $^{13}$C NMR (d-6 Acetone, 100 MHz) δ ppm 149.303, 144.865, 140.867, 139.425, 133.391, 125.254, 124.568, d124.493, 121.149, 115.595, 42.117. Calculated 213.1266. Actual 213.1259.

Example 6B N$^1$,N$^1$-dibutyl-N$^4$-(pyrimidin-5-yl)benzene-1,4-diamine (24)

Compound 24 was prepared in 45% yield from 4-amino-N,N-dibutylaniline (prepared by catalytic hydrogenation of 4-nitro-N,N-dibutylaniline prepared as in Mansour, G.; Creedon, W.; Dorrestein, P. C.; Maxka, J.; MacDonald, J. C.; Helburn, R. *J. Org. Chem.* 2001, 66, 4050-4054) and 5-bromopyrimidine (Aldrich) as outlined in Example 3.

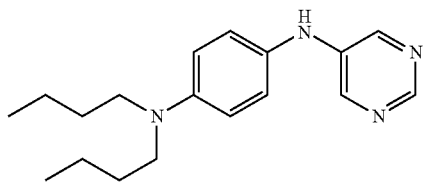

24

$^1$H NMR (CDCl$_3$, 400 MHz) δ ppm 8.62 (s, 1H), 8.27 (s, 2H), 7.02 (dd, J=2.0, 7.2 Hz, 2H), 6.27 (dd, J=2.0, 7.2 Hz, 2H), 5.40 (bs, 1H), 3.26 (t, J=7.6 Hz, 4H), 1.53-1.59 (m, 4H), 1.33-1.39 (m, 4H), 0.96 (t, J=7.2 Hz, 6H). $^{13}$C NMR (d-6 Acetone, 100 MHz) δ ppm 150.247, 147.419, 143.452, 143.426, 130.531, 125.629, 125.559, 114.794, 52.564, 21.906, 15.286. Calculated 298.2157. Actual 298.2152.

Example 6C N$^1$,N$^1$-dimethyl-N$^4$-(pyridin-2-yl)benzene-1,4-diamine (25)

Compound 25 was prepared in 80% yield from 4-bromo-N,N-dimethylaniline (Aldrich) and 2-bromopyridine (Aldrich) as outlined in Example 3.

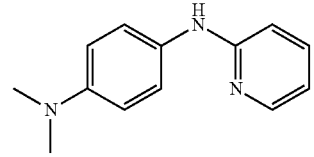

25

$^1$H NMR (CDCl$_3$, 400 MHz) δ ppm 8.13 (d, J=4.0 Hz, 1H), 7.38 (t, J=7.2 Hz, 1H), 7.17 (d, J=4.0 Hz, 2H), 6.75 (d, J=3.6 Hz, 2H), 6.62 (d, J=3.6 Hz, 2H), 6.25 (bs, 1H), 2.94 (s, 6H). $^{13}$C NMR (CDCl$_3$, 100 MHz) δ ppm 158.062, 148.348, 148.076, 137.516, 129.640, 124.928, 113.732, 113.576, 106.708, 41.003. Calculated 213.1266, Actual 213.1260

Example 6D N$^1$,N$^1$-dipropyl-N$^4$-(pyrimidin-2-yl)benzene-1,4-diamine (26)

Compound 26 was prepared in 47% yield from 4-amino-N,N-dipropylaniline (prepared by catalytic hydrogenation of 4-nitro-N,N-dipropylaniline prepared as in Mansour, G.; Creedon, W.; Dorrestein, P. C.; Maxka, J.; MacDonald, J. C.; Helburn, R. *J. Org. Chem.* 2001, 66, 4050-4054) and 2-bromopyrimidine (Aldrich) as outlined in Example 3.

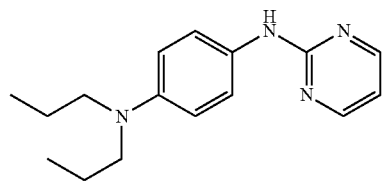

26

$^1$H NMR (CDCl$_3$, 400 MHz) δ ppm 8.33 (d, J=4.8 Hz, 2H), 7.31 (dd, J=2.0, 6.8 Hz, 2H), 6.97 (bs, 1H), 6.37 (dd, J=2.0, 6.8 Hz, 2H), 6.59 (t, J=4.8 Hz, 1H), 3.21 (t, J=8.0 Hz, 4H), 1.55-1.64 (m, 4H), 0.92 (t, J=7.2 Hz, 6H). $^{13}$C NMR (CDCl$_3$, 100 MHz) δ ppm 161.173, 158.070, 145.354, 127.228, 123.401, 112.315, 111.394, 53.182, 20.430, 11.461. Calculated 270.1844. Actual 270.1864.

Example 6E N$^2$,N$^2$-dimethyl-N$^5$-phenylpyridine-2,5-diamine (27)

Compound 27 was prepared in 94% yield from 2-(N,N-dimethylamino)-5-bromopyridine (prepared as in Example 5, see also: Nara, S. J.; Jha, M.; Brinkhorst, J.; Zemanek, T. J.; Pratt, D. A. *J. Org. Chem.* 2008, 73, 9326) and aniline (Aldrich) as outlined in Example 3.

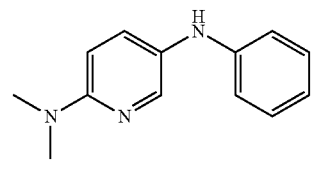

27

$^1$H NMR (CDCl$_3$, 400 MHz) δ ppm 8.06 (d, J=2.4 Hz, 1H), 7.35 (dd, J=2.8, 9.2 Hz, 1H), 7.17 (t, J=8.0 Hz, 1H), 6.75-6.79 (m, 3H), 6.52 (d, J=8.4 Hz, 1H), 5.33 (bs, 1H), 3.08 (s, 6H). $^{13}$C NMR (CDCl$_3$, 100 MHz) δ ppm 156.753, 146.497, 143.671, 133.964, 129.294, 127.555, 118.828, 114.278, 106.114, 38.473. Calculated 213.1266. Actual 213.1185.

Example 6F N²,N²-dimethyl-N⁵-phenylpyrimidine-2,5-diamine (28)

Compound 28 was prepared in 93% yield from 2-(N,N-dimethylamino)-5-bromopyrimidine (prepared as in Example 5, see also: Nara, S. J.; Jha, M.; Brinkhorst, J.; Zemanek, T. J.; Pratt, D. A. *J. Org. Chem.* 2008, 73, 9326) and aniline (Aldrich 132934) as outlined in Example 3.

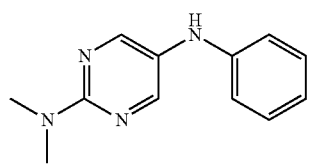

28

¹H NMR (CDCl3, 400 MHz) δ ppm 8.25 (s, 2H), 7.18 (dt, J=2.0, 7.6 Hz, 2H), 6.79 (t, J=7.6 Hz, 1H), 6.72 (dd, J=1.2, 7.8 Hz, 2H). ¹³C NMR (CDCl₃, 100 MHz) δ ppm 159.953, 155.019, 146.393, 129.420, 125.308, 119.120, 113.393, 37.419. Calculated 214.1218. Actual 214.1197.

Example 6G N⁵-(4-(dimethylamino)phenyl)-N²,N²-dimethylpyridine-2,5-diamine (29)

Compound 29 was prepared in X % yield from 2-(N,N-dimethylamino)-5-bromopyridine and N,N-dimethyl-p-phenylenediamine (Aldrich) as outlined in Example 3.

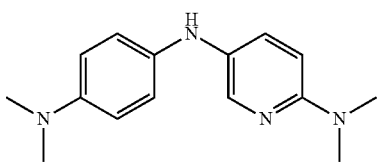

29

¹H NMR (400 MHz, (CD₃)₂CO) δ ppm 7.93 (d, J=2.8 Hz, 1H), 7.27 (dd, J=9.2, 2.8 Hz, 1H), 6.83 (m, 2H), 6.70 (m, 2H), 6.58 (d, J=9.2 Hz, 1H), 6.39 (bs, 1H), 2.99 (s, 6H), 2.82 (s, 6H). ¹³C (100 MHz, (CD₃)₂CO) δ ppm 157.212, 147.356, 141.178, 138.789, 133.454, 131.217, 119.668, 116.501, 107.804, 42.732, 39.629. Calculated 256.1688. Actual 256.1692.

Example 6H N⁵-(6-(dimethylamino)pyridin-3-yl)-N²,N²-dimethylpyridine-2,5-diamine (30)

Compound 30 was prepared in 72% yield from 2-(N,N-dimethylamino)-5-bromopyridine and 2-(N,N-dimethylamino)-5-aminopyridine (prepared as in Examples 4 and 5, respectively, see also: Nara, S. J.; Jha, M.; Brinkhorst, J.; Zemanek, T. J.; Pratt, D. A. *J. Org. Chem.* 2008, 73, 9326) as outlined in Example 3.

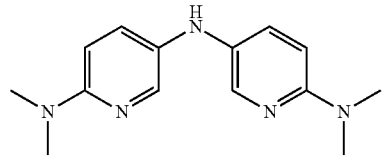

30

¹H NMR (CDCl₃, 400 MHz) δ ppm 7.94 (d, J=2.4 Hz, 2H), 7.19 (dd, J=2.8, 8.8 Hz, 2H), 6.49 (d, J=8.8 Hz, 2H), 4.95 (bs, 1H), 3.05 (s, 12H). ¹³C NMR (CDCl₃, 100 MHz) δ ppm 155.707, 139.145, 131.279, 121.439, 106.440, 38.677. Calculated 257.1640, Actual 257.1646

Example 6I N⁵-(4-(dimethylamino)phenyl)-N²,N²-dimethylpyrimidine-2,5-diamine (31)

Compound 31 was prepared in 87% yield from 2-(N,N-dimethylamino)-5-bromopyrimidine (prepared as in Example 5, see also: Nara, S. J.; Jha, M.; Brinkhorst, J.; Zemanek, T. J.; Pratt, D. A. *J. Org. Chem.* 2008, 73, 9326) and N,N-dimethyl-p-phenylenediamine (Aldrich 193992) as outlined in Example 3.

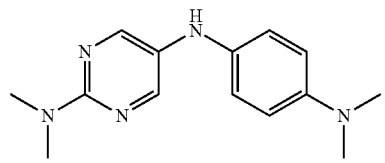

31

¹H NMR (d-₆ DMSO, 400 MHz) δ ppm 8.15 (s, 2H), 7.15 (bs, 1H), 6.74 (dd, J=2.4, 6.8 Hz, 2H), 6.65 (dd, J=2.4, 6.8 Hz, 2H), 3.07 (s, 3H), 2.77 (s, 3H). ¹³C NMR (d-₆ DMSO, 100 MHz) δ ppm 157.971, 149.638, 144.656, 136.186, 128.849, 116.514, 114.485, 41.106, 36.959. Calculated 257.1640, Actual 257.1632.

Example 6J N⁵-(6-(dimethylamino)pyridin-3-yl)-N², N²-diethylpyrimidine-2,5-diamine (32)

Compound 32 was prepared in 91% yield from 2-(N,N-dimethylamino)-5-bromopyridine (prepared as in Example 5, see also: Nara, S. J.; Jha, M.; Brinkhorst, J.; Zemanek, T. J.; Pratt, D. A. *J. Org. Chem.* 2008, 73, 9326) and 2-(N,N-diethylamino)-5-aminopyrimidine (prepared as in Example 4) as outlined in Example 3.

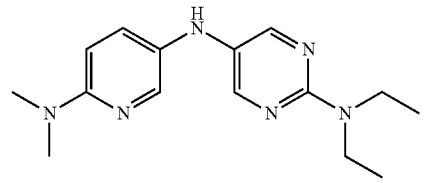

32

¹H NMR (CDCl₃, 400 MHz) δ ppm 8.70 (s, 2H), 7.87 (d, J=2.8 Hz, 1H), 7.10 (dd, J=2.8, 8.8 Hz, 1H), 6.46 (d, J=8.8 Hz, 1H), 4.75 (bs, 1H), 3.58 (q, J=7.2 Hz, 4H), 3.03 (s, 3H), 1.18 (t, J=6.8 Hz, 6H). ¹³C NMR (CDCl₃, 100 MHz) δ ppm 158.089, 155.506, 151.619, 137.817, 137.787, 131.823, 128.154, 127.972, 42.092, 38.709, 13.162. Calculated 286.1906, 286.1907.

Example 6K N$^5$-(2-(diethylamino)pyrimidin-5-yl)-N$^2$,N$^2$-diethylpyrimidine-2,5-diamine (33)

Compound 33 was prepared in 78% yield from 2-(N,N-diethylamino)-5-bromopyrimidine (prepared as in Example 5) and 2-(N,N-diethylamino)-5-aminopyrimidine (prepared as in Example 4) as outlined in Example 3.

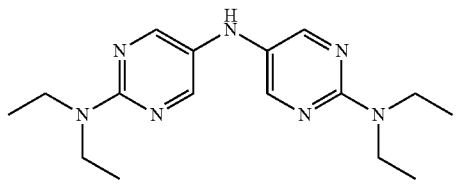

33

$^1$H NMR (CDCl$_3$, 400 MHz) δ ppm 8.01 (s, 4H), 4.52 (bs, 1H), 3.51 (q, 6.8 Hz, 8H), 1.17 (t, 6.8 Hz, 12H). $^{13}$C NMR (CDCl$_3$, 100 MHz) δ ppm 157.938, 150.354, 128.517, 128.499, 42.116, 13.012. Calculated 315.2171, Actual 315.2150.

Example 6L bis(6-methoxypyridin-3-yl)amine (34)

Compound 34 was prepared in 64% yield from 5-bromo-2-methoxypyridine (Aldrich 510297) and 5-amino-2-methoxypyridine (Aldrich A61209) as outlined in Example 3.

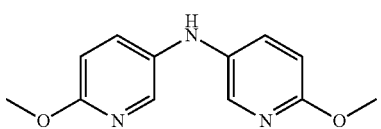

34

$^1$H NMR (CDCl$_3$, 400 MHz) δ ppm 7.80 (d, J=2.6 Hz, 2H), 7.20 (dd, J=2.6, 8.8 Hz, 2H), 6.61 (d, J=8.8 Hz, 2H), 5.12 (bs, 1H), 3.83 (s, 6H). $^{13}$C NMR (CDCl3, 100 MHz) δ ppm 159.644, 136.842, 134.541, 130.397, 111.081, 53.490. Calculated 231.1008, Actual 231.0996.

Example 6M bis(6-(hex-1-ynyl)pyridin-3-yl)amine (35)

Compound 35 was prepared in 48% yield from 3-bromo-6-(hex-1-ynyl)-pyridine (prepared as in Robbins, M. J.; Nowak, I.; Rajwanshi, V. K.; Miranda, K.; Cannon, J. F.; Peterson, M. A.; Andrei, G.; Snoeck, R.; De Clercq, E.; Balzarini, J. *J. Med. Chem.* 2007, 50, 3897-3905) and 3-amino-6-(hex-1-ynyl)-pyridine (prepared as in Example 4) as outlined in Example 3.

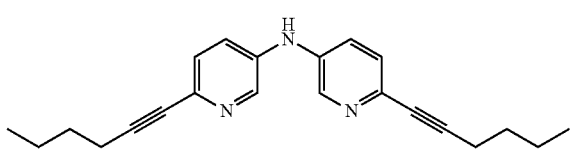

35

$^1$H NMR (CDCl$_3$, 400 MHz) δ ppm 8.25 (s, 2H), 7.58 (bs, 1H), 7.30 (d, J=6.8 Hz, 2H), 7.19 (d, J=8.8 Hz, 2H), 2.28 (t, J=6.8 Hz, 4H), 1.32-1.47 (m, 8H), 0.82 (t, J=7.2 Hz, 6H). $^{13}$C NMR (CDCl$_3$, 100 MHz) δ ppm 140.085, 137.705, 135.939, 127.065, 123.482, 89.967, 79.873, 30.357, 21.895, 18.859, 13.479. Calculated 331.2048, Actual 331.2054.

Example 6N bis(6-hexylpyridin-3-yl)amine (36)

Compound 36 was prepared in 66% yield from 3-bromo-6-hexylpyridine (prepared as in Robbins, M. J.; Nowak, I.; Rajwanshi, V. K.; Miranda, K.; Cannon, J. F.; Peterson, M. A.; Andrei, G.; Snoeck, R.; De Clercq, E.; Balzarini, J. *J. Med. Chem.* 2007, 50, 3897-3905) and 3-amino-6-hexylpyridine (prepared as in Example 4) as outlined in Example 3.

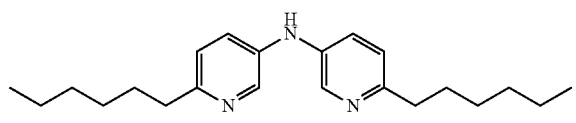

36

$^1$H NMR (CDCl$_3$, 400 MHz) δ ppm 8.29 (d, J=2.4 Hz, 2H), 7.31 (dd, J=2.8, 8.4 Hz, 2H), 7.04 (d, J=8.4 Hz, 2H), 5.89 (bs, 1H), 2.73 (t, J=8.0 Hz, 4H), 1.66-1.73 (m, 4H), 1.29-1.37 (m, 12H), 0.88 (t, J=6.8 Hz, 6H). $^{13}$C NMR (CDCl$_3$, 100 MHz) δ ppm 155.434, 139.786, 136.952, 124.901, 122.723, 37.574, 31.729, 30.038, 29.063, 22.602, 14.093. Calculated 339.2674, Actual 339.2685.

Example 6O
6-methoxy-N-(4-methoxyphenyl)pyridin-3-amine (37)

Compound 37 was prepared in 58% yield from p-anisidine (Aldrich A88255) and 5-bromo-2-methoxypyridine (Aldrich) as outlined in Example 3.

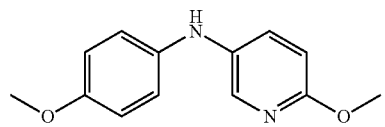

37

$^1$H NMR (CDCl$_3$, 400 MHz) δ ppm 7.90 (d, J=3.2 Hz, 1H), 7.32 (dd, J=3.2, 12 Hz, 1H), 6.89 (dd, J=3.2, 8.8 Hz, 2H), 6.83 (dd, J=3.2, 12 Hz, 2H), 6.68 (d, J=12 Hz, 1H), 5.39 (bs, 1H), 3.91 (s, 3H), 3.77 (s, 3H). $^{13}$C NMR (CDCl$_3$, 100 MHz) δ ppm 159.121, 154.391, 137.383, 136.603, 134.934, 130.699, 119.172, 114.750, 110.810, 55.559, 53.468. Calculated 230.1055, Actual 230.1042.

Example 6P 6-hexyl-N-phenylpyridin-3-amine (38)

Compound 38 was prepared in 88% yield from 3-bromo-6-hexylpyridine (prepared as in Robbins, M. J.; Nowak, I.; Rajwanshi, V. K.; Miranda, K.; Cannon, J. F.; Peterson, M. A.; Andrei, G.; Snoeck, R.; De Clercq, E.; Balzarini, J. *J. Med. Chem.* 2007, 50, 3897-3905) and aniline (Aldrich) as outlined in Example 3.

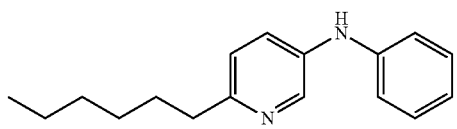

¹H NMR (CDCl₃, 400 MHz) δ ppm 8.29 (d, J=2.8 Hz, 1H), 7.34 (dd, J=2.8, 8.4 Hz, 1H), 7.21-7.26 (m, 2H), 6.98-7.02 (m, 3H), 6.91 (tt, J=1.2, 7.6 Hz, 1H), 5.90 (bs, 1H), 2.71 (t, J=8.0 Hz, 2H), 1.64-1.72 (m, 2H), 1.26-1.35 (m, 6H), 0.86 (t, J=6.8 Hz, 3H). ¹³C NMR (CDCl₃, 100 MHz) δ ppm 154.970, 142.860, 140.103, 137.057, 129.373, 125.389, 122.537, 121.038, 117.103, 37.478, 31.653, 30.002, 28.997, 22.526, 14.029. Calculated 254.1783. Actual 254.1796.

Example 6Q 6-methoxy-N-phenylpyridin-3-amine (39)

Compound 39 was prepared in 93% yield from 5-bromo-2-methoxypyridine (Aldrich) and aniline (Aldrich) as outlined in Example 3.

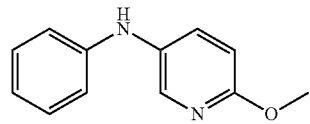

¹H NMR (CDCl₃, 400 MHz) δ ppm 8.25 (d, J=2.4 Hz, 1H), 8.06 (dd, J=1.6, 4.8 Hz, 1H), 7.20 (ddd, J=1.4, 2.4, 8.3 Hz, 1H), 7.06-7.11 (m, 3H), 6.87-6.90 (m, 2H), 5.58 (bs, 1H), 3.81 (s, 3H). ¹³C NMR (CDCl₃, 100 MHz) δ ppm 155.928, 141.672, 140.678, 140.655, 138.390, 134.360, 123.653, 122.728, 121.145, 114.844, 55.567.

Example 6R
2-methoxy-N-(4-methoxyphenyl)pyrimidin-5-amine (40)

Compound 40 was prepared in 18% yield from 5-bromo-2-methoxypyrimidine (Aldrich) and p-anisidine (Aldrich) as outlined in Example 3.

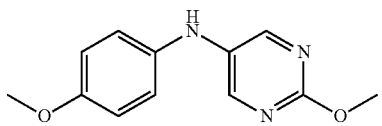

¹H NMR (d-3MeCN, 400 MHz) δ ppm 8.29 (s, 1H), 6.98 (d, J=8.8 Hz, 2H), 6.87 (d, J=8.8 Hz, 2H), 3.92 (s, 3H), 3.77 (s, 3H); Calculated 231.1008, Actual 231.1018.

Example 6S N¹,N¹-dimethyl-N⁴-(pyrimidin-5-yl)benzene-1,4-diamine (41)

Compound 41 was prepared in 77% yield from N,N-dimethylphenylenediamine (Aldrich) and 5-bromopyrimidine (Aldrich) as outlined in Example 3.

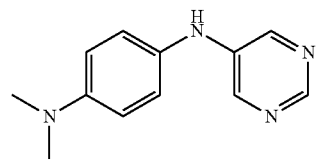

¹H NMR (CDCl₃, 400 MHz) δ ppm 8.64 (s, 1H), 8.29 (s, 2H), 7.07 (d, J=8.8 Hz, 2H), 6.74 (d, J=8.8 Hz, 2H), 5.41 (bs, 1H), 2.96 (s, 6H). ¹³C NMR (CDCl₃, 100 MHz) δ ppm 149.449, 148.444, 142.434, 140.737, 128.831, 124.315, 113.678, 40.874. Calculated 214.1218, Actual 214.1226.

Example 6T N¹,N¹-dimethyl-N⁴-(pyrimidin-2-yl)benzene-1,4-diamine (42)

Compound 42 was prepared in 45% yield from N,N-dimethylphenylenediamine (Aldrich) and 2-bromopyrimidine (Aldrich) as outlined in Example 3.

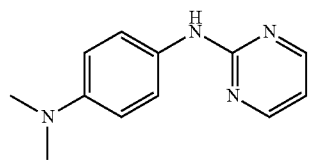

¹H NMR (CDCl₃, 400 MHz) δ ppm 8.34 (d, J=4.8 Hz, 2H), 7.57 (bs, 1H), 7.40 (d, J=8.8 Hz, 2H), 6.76 (d, J=2.0 Hz, 2H), 6.60 (t, J=4.8 Hz, 1H), 2.93 (s, 6H). ¹³C NMR (CDCl₃, MHz) δ ppm 161.016, 158.006, 147.617, 128.986, 122.770, 113.445, 111.447, 41.084. Calculated 214.1218, Actual 214.1221.

Example 6U N⁵-(6-(dipentylamino)pyridin-3-yl)-N²,N²-dipentylpyridine-2,5-diamine (43)

Compound 43 was prepared in 84% yield from N²,N²-dipentylpyridine-2,5-diamine (prepared as described below) and 5-bromo-N,N-dipentylpyrimidin-2-amine (prepared as described below) as outlined in Example 3.

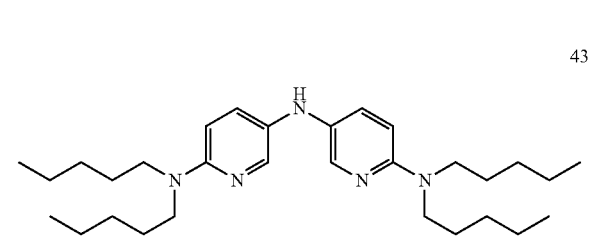 [SMILES: CCCCCN(CCCCC)c1ccc(Nc2ccc(N(CCCCC)CCCCC)nc2)cn1]

After preparation, yield 84% green solid. ¹H NMR (CDCl₃, 400 MHz) δ ppm 7.89 (d, J=2.4 Hz, 2H), 7.14 (dd, J=2.8, 9.0 Hz, 2H), 6.38 (d, J=9.0 Hz, 2H), 4.82 (bs, 1H), 3.39 (t, J=7.4 Hz, 8H), 1.59 (m, 8H), 1.34 (m, 16H), 0.92 (t, J=6.8 Hz, 12H). ¹³C NMR (CDCl₃, 100 MHz) δ ppm 154.332, 139.416, 130.693, 129.655, 105.875, 48.972, 29.377, 27.455, 22.657, 14.114. Calculated 481.4144, Actual 481.4146.

Example 6V 6-(Hex-1-ynyl)pyridin-3-amine (44)

Compound 44 was prepared in 95% yield from 3-bromo-6-(hex-1-ynyl)-pyridine (prepared as in Robbins, M. J.;

Nowak, I.; Rajwanshi, V. K.; Miranda, K.; Cannon, J. F.; Peterson, M. A.; Andrei, G.; Snoeck, R.; De Clercq, E.; Balzarini, J. *J. Med. Chem.* 2007, 50, 3897-3905) as described in Example 4.

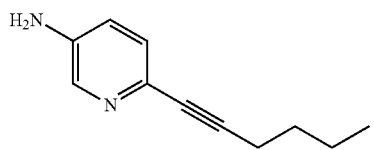

¹H NMR (CDCl₃, 300 MHz) δ ppm 8.02 (s, 1H), 7.16 (d, J=8.3 Hz, 1H), 6.88 (dd, J=2.1, 8.3 Hz, 1H), 3.80 (s, 2H), 2.41 (t, J=6.6 Hz, 2H), 1.44-1.64 (m, 4H), 0.93 (t, J=7.1 Hz, 3H). ¹³C NMR (CDCl₃, 100 MHz) δ ppm 141.436, 137.152, 133.619, 127.103, 121.326, 88.497, 30.601, 22.025, 18.987, 13.614. Calculated 174.1157, Actual 174.1150.

Example 6W
5-Bromo-N,N-dipentylpyrimidin-2-amine (45)

Compound 45 was prepared as follows. To a solution of 5-bromo-2-aminopyridine (348 mg, 2.0 mmol) and pentanel (689 mg, 8.0 mmol) in MaCN (7.0 mL) was added Na(OAc)₃BH (1.70 g, 8.0 mmol) in one portion. The solution was heated to reflux and the reaction monitored by TLC. Upon completion, MeCN was removed in vacuo and the reaction mixture was redissolved in EtOAc (20 mL), washed with water (2×20 mL) and brine (20 mL) and dried over MgSO₄. Purification by column chromatography using silica gel with hexanes/EtOAc (98:2) afforded 79% yield of the desired compound.

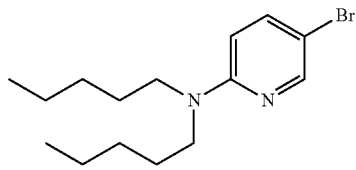

¹H NMR (CDCl₃, 400 MHz) δ ppm 8.14 (d, J=2.5 Hz, 1H), 7.42 (dd, J=2.5, 9.1 Hz, 1H), 6.33 (d, J=9.1 Hz, 1H), 3.39 (t, J=7.5 Hz, 4H), 1.54-1.62 (m, 4H), 1.25-1.39 (m, 8H), 0.92 (t, J=7.1 Hz, 6H). ¹³C NMR (CDCl₃, 100 MHz) δ ppm 156.457, 148.538, 139.046, 106.890, 104.987, 48.885, 29.275, 27.196, 22.614, 14.086. Calculated 312.1201, Actual 312.1208.

Example 6X N⁵-benzyl-N²,N²-dipentylpyridine-2,5-diamine (46)

Compound 46 was prepared in 87% yield from compound 45 as described in Example 4.

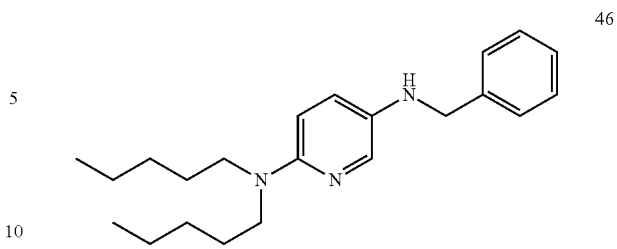

After preparation, yield 87% yellow solid. ¹H NMR (CDCl₃, 300 MHz) δ ppm 7.73 (d, J=2.8 Hz, 1H), 7.30-7.39 (m, 5H), 6.96 (dd, J=2.9, 9.0 Hz, 1H), 6.40 (d, J=9.0 Hz, 1H), 4.27 (s, 2H), 3.37 (t, J=7.6 Hz, 4H), 1.54-1.58 (m, 4H), 1.25-1.40 (m, 8H), 0.91 (t, J=6.8 Hz, 6H). ¹³C NMR (CDCl₃, 100 MHz) δ ppm 152.714, 139.890, 134.913, 133.777, 128.596, 127.621, 127.164, 125.054, 106.337, 49.862, 49.076, 29.494, 27.623, 22.758, 14.217. Calculated 337.2518, Actual 337.2519

Example 7 Additional Preparation of Diarylamines

Additional synthesis of various substituted diarylamines was undertaken so as to be able to provide a comprehensive array of diarylamines for purposes of the studies and comparisons as described herein. Many of these compounds have also been described as prepared in Example 3. A great number of phosphine ligands have been developed for Pd-catalyzed C—N bond forming reactions, and the original ligand screen showed a broad structural variety of phosphines were useful when coupling substituted bromo-pyri (mi)dines with aniline (e.g. BINAP, Josiphos, SPhos, DPPF). However, 2-dicyclohexylphosphino-2',4',6'-triisopropylbiphenyl (XPhos) (Anderson, K. W.; Tundel, R. E.; Ikawa, T.; Altman, R. A.; Buchwald, S. L. *Angew. Chem. Int. Edit.* 2006, 45, 6523) gave consistently good results, showing the least sensitivity to the electronics of the aryl bromides and also has the added benefit of being air stable and therefore easily handled. Based on these results, the catalytic system of 2 mol % Pd2(dba)₃ as a palladium source was used along with 4 mol % XPhos as a ligand. An additional series of dialkylamino-substituted pyridine and pyrimidine-based diarylamines were prepared, with alkyl groups varied to improve solubility in hydrocarbon solvents, as shown in Table 4. The conversions were very good for nearly all of the substrates shown—the exception being 2-substituted pyrimidine 51; however, the isolated yields in some cases do not reflect product conversion due to difficulty with purification and/or sensitivity to oxidation in solution. It was surmises that the poor reactivity of 2-aminopyrimidine is due the relatively low pKa (6.8) of this compound, 47 and corresponding poor nucleophilicity. Switching nucleophile and electrophile and using N,N-dimethylbenzene-1,4-diamine and 2-bromopyrimidine also resulted in poor yields due to competing reduction of the aryl bromide by the highly electron-rich aryl amine.

A similar set of compounds were prepared having alkyl substituents that allowed the exploration of the effect of heteroatom incorporation on stability and reactivity using the industry standards (4,4'-dialkyldiphenylamines) as a baseline for comparison (Table 5). The isolated yields for these compounds are generally quite good. As noted previously, compounds such as those with unsubstituted pyrimidines (66) can be difficult to purify by chromatography.

To round out the series, a set of alkoxy-substituted compounds were prepared that were anticipated to have reactivities/stabilities in between the dialkylamino- and alkyl-compounds (Table 6). In the case of alkoxy-substituted compounds the reaction becomes more complicated because the alkoxide represents a reasonable leaving group and when in the electrophilic 2-position of a pyridine or pyrimidine ring and in the presence of a nucleophillic amine coupling partner a competing SNAr reaction can occur. This is reflected in some of the isolated yields—although it was found that the use of bulkier alkyl groups helped to minimize the undesired substitution reaction.

Unfortunately, the symmetrical 2-alkoxypyrimidine compound (64) could not be prepared by the C—N coupling approach as the amines always underwent nucleophillic substitution at the 2-position prior to the desired coupling. Because products were obtained for 77, 82 and 84—compounds which also feature 2-alkoxypyrimidine rings—it is believed that the desired coupling reaction is sluggish due to the arylamine coupling partner not readily participating in the catalytic cycle. An attempt was made to decrease the rate of nucleophillic substitution relative to that of amine ligation to palladium by using relatively bulky alkyl substituents (—OCy, —OMeCy, —OBn, —OEtPh, etc.), keeping in mind that the substituent must be small enough to allow conjugation of the oxygen p-orbital (lone pair) with the pyrimidine ring to be effective as an antioxidant. However, none of these compounds gave the desired result.

TABLE 4

N,N-Dialkylamino-substituted diarylamines prepared by palladium-catalyzed cross-couplings of aryl bromides and aryl amines.

$$\text{Ar—Br} + \text{Ar}^1\text{—NH}_2 \xrightarrow[\text{toluene, 90° C.}]{\text{Pd}_2\text{dba}_3, \text{XPhos, NaO}^t\text{Bu}} \text{Ar—NH—Ar}^1$$

| Ar—NH—Ar¹ | # | X | Y | R | Yield[a] |
|---|---|---|---|---|---|
| structure 1 | 47 | CH | CH | Me | 93 b |
|  | 48 | N | CH | Me | 74 b |
|  | 49 | N | N | Pr | 77 b |
| structure 2 | 50 | N | CH | Me | 80 b |
|  | 51 | N | N | Pr | 45 b |
| structure 3 | 52 | N | CH | Me | 94 |
|  | 53 | N | N | Me | 93 |
|  | 54 | CH | CH | Me | 89 |
| structure 4 | 55 | N | CH | Me | 62 |
|  | 56 | N | N | Pr | 87 b |
| structure 5 | 57 | CH | CH | Me | 72 |
|  | 58 | N | CH | Et/Me | 91 |
|  | 59 | N | N | Et | 81 b |

The conditions used resulting in yield as shown in Table 4[a] were: ArBr (1.0 mmol), ArNH2 (1.1 mmol), Pd (2 mol %), XPhos (4 mol %), NaOtBu (1.4 mmol) in degassed toluene (2 mL) heated to 90° C. As shown in Table 4, b indicates reactions were done using Pd(η³-1-PhC₃H₄)(η⁵-C₅H₅) (compound 86).

Upon preparation of a series of diarylamines, it could be readily seen that with increasing nitrogen incorporating into the aromatic rings the diarylamines were much more stable to oxidation. For example, on comparing the series of symmetrically-substituted diarylamines in Table 4, compounds 54 and 55 became intensely colored (due to formation of a radical cation, vide supra) almost immediately upon exposure to air in solution, while compounds 56, 57, 58 and 59 were bench stable.

TABLE 5

Alkyl-substituted diarylamines prepared by palladium-catalyzed cross-couplings of aryl bromides and aryl amines.

$$\text{Ar—Br} + \text{Ar}^1\text{—NH}_2 \xrightarrow[\text{toluene, 90°C}]{\text{Pd}_2\text{dba}_3,\ \text{XPhos, NaO}^t\text{Bu}} \text{Ar—NH—Ar}^1$$

| Ar—NH—Ar¹ (structure) | # | X | Y | R/R' | Yield[a] |
|---|---|---|---|---|---|
| Structure A (2-R-pyridyl/pyrimidyl-NH-phenyl) | 60 | CH | CH | Bu | 95 |
|  | 61 | N | CH | C$_6$H$_{13}$ | 88 |
|  | 62 | N | N | C$_7$H$_{15}$ | 83 |
|  | 63 | N | CH | H | 94 b |
|  | 64 | N | N | H | 82 b |
| Structure B (pyridyl-NH-(4-R-phenyl)) | 65 | N | CH | Bu | 73 |
|  | 66 | N | N | Bu | 62 |
| Structure C (2-R-pyridyl/pyrimidyl-NH-(4-R'-phenyl)) | 67 | CH | CH | C$_8$H$_{17}$ | 86 b |
|  | 68 | N | CH | C$_6$H$_{13}$/Bu | 62 |
|  | 69 | N | N | C$_6$H$_{13}$/Bu | 84 |
| Structure D (bis-pyrimidyl diarylamine) | 70 | CH | CH | C$_6$H$_{13}$ | 85 |
|  | 71 | N | CH | C$_6$H$_{13}$/C$_7$H$_{15}$ | 71 |
|  | 72 | N | N | C$_7$H$_{15}$ | 81 |
|  | 73 | CH | CH | H | 89 b |
|  | 74 | N | N | H | 77 b |

The conditions used resulting in yield as shown in Table 5[(a)] were: ArBr (1.0 mmol), ArNH2 (1.1 mmol), Pd (2 mol %), XPhos (4 mol %), NaOtBu (1.4 mmol) in degassed toluene (2 mL) heated to 90° C. As shown in Table 5, b indicates reactions were done using Pd($\eta^3$-1-PhC$_3$H$_4$)($\eta^5$-C$_5$H$_5$) (compound 86).

TABLE 6

Alkoxy-substituted diarylamines prepared by palladium-catalyzed cross-couplings of aryl bromides and aryl amines.

$$\text{Ar—Br} + \text{Ar}^1\text{—NH}_2 \xrightarrow[\text{toluene, 90° C.}]{\text{Pd}_2\text{dba}_3, \text{XPhos, NaO}^t\text{Bu}} \text{Ar—NH—Ar}^1$$

| Ar—NH—Ar¹ | | X | Y | R/R' | Yield[a] |
|---|---|---|---|---|---|
| (RO-pyridine-NH-phenyl) | 75 | CH | CH | Me | 90 |
| | 76 | N | CH | Me | 93 |
| | 77 | N | N | Cy | 57 |
| (RO-phenyl-NH-pyridine) | 78 | N | CH | Me | 98 b |
| | 79 | N | N | Me | 87 b |
| (RO-pyridine-NH-phenyl-OR) | 80 | CH | CH | Me | 96 b |
| | 81 | N | CH | Me | 58 b |
| | 82 | N | N | EtPh | 84 b |
| (RO-pyrimidine-NH-pyrimidine-OR') | 83 | CH | CH | Me | 98 |
| | 84 | N | CH | EtPh/Bu | 43 |
| | 85 | N | N | N/A | N/A |

The conditions used resulting in yield as shown in Table 6[(a)] were: ArBr (1.0 mmol), ArNH2 (1.1 mmol), Pd (2 mol %), XPhos (4 mol %), NaOtBu (1.4 mmol) in degassed toluene (2 mL) heated to 90° C. As shown in Table 6, b indicates reactions were done using Pd($\eta^3$-1-PhC$_3$H$_4$)($\eta^5$-C$_5$H$_5$) (compound 86).

Although the Pd$_2$(dba)$_3$/XPhos catalyst system was effective for the preparation of the bulk of the diarylamines shown in Tables 4-6, it was found that Pd($\eta^3$-1-PhC$_3$H$_4$)($\eta^5$-C$_5$H$_5$) precatalyst (86) afforded higher isolated yields in essentially all cases where a direct comparison was made. It is believed that the increased yields from the 86/XPhos system can be attributed to the rapid and irreversible formation of the active PdL$_2$ catalyst (Norton, D. M.; Mitchell, E. A.; Botros, N. R.; Jessop, P. G.; Baird, M. C. *J. Org. Chem.* 2009, 74, 6674) compared to when Pd$_2$(dba)$_3$ is used, which remains in equilibrium with PdL$_2$.

Figure 1B:
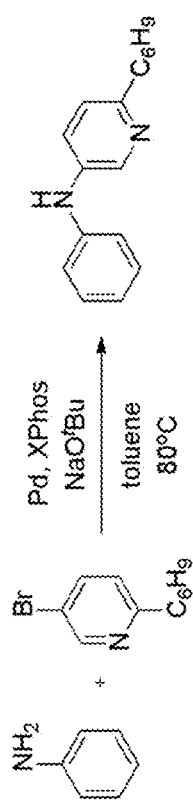
Figure 1B:
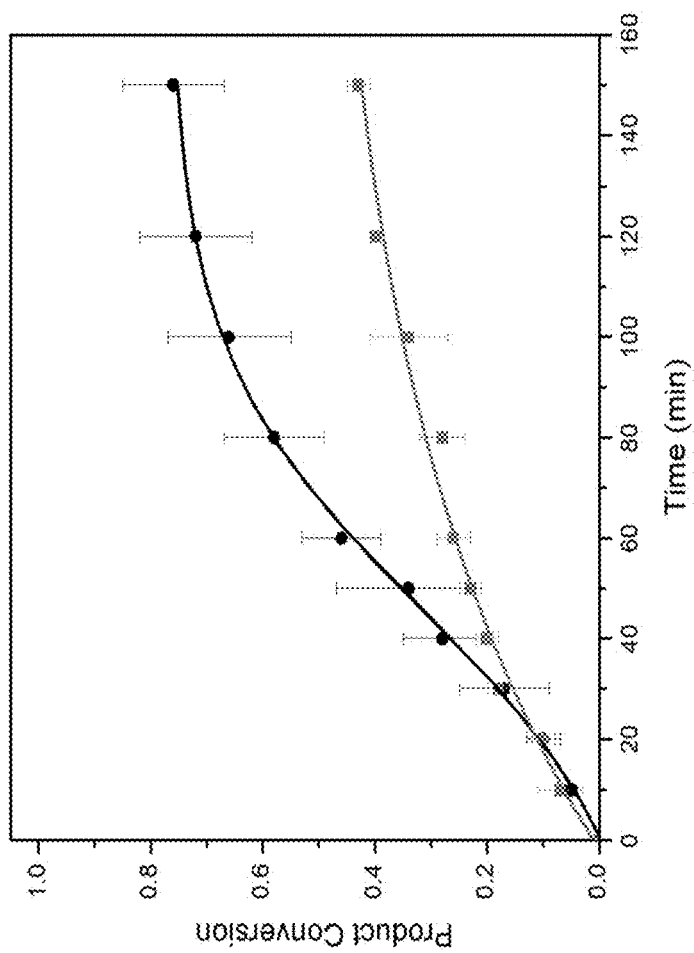
Figure 1C:
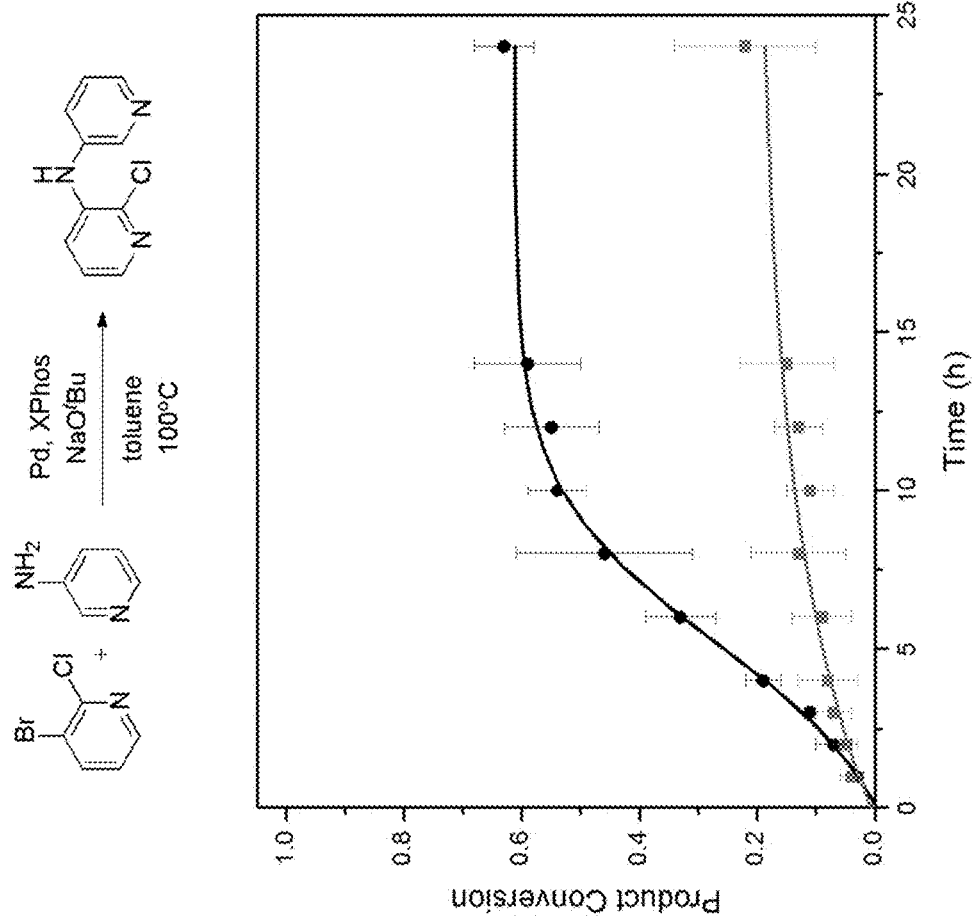

Example 8 Comparison of Pd$_2$(dba)$_3$ and Pd($\eta^3$-1-PhC$_3$H$_4$)($\eta^5$-C$_5$H$_5$) as PreCatalysts The reaction progress of these two Pd precatalysts in three representative reactions was monitored under otherwise identical conditions (FIGS. 1A, 1B and 1C). The first two compounds selected for the reactions (FIGS. 1A and 1B) were randomly chosen from the many examples of compounds described herein, and the third compound was selected based on previous discussion in the prior art of problems making this compound (FIG. 1C); the diarylamine product could be obtained in a modest 56% yield, but required high precatalyst loading (Pd(OAc)2, 15 mol %), large amounts of ligand (XantPhos, 30 mol %), long reaction time (48 h) and utilized 3-iodo-2-chloropyridine as a more reactive coupling partner than the corresponding 3-bromo-2-chloropyridine (which was used below) (Patriciu, O. I.; Finaru, A. L.; Massip, S.; Leger, J. M.; Jarry, C.; Guillaumet, G. Eur. *J. Org. Chem.* 2009, 3753). In each case, the reaction progress was monitored under typical preparative conditions at regular time intervals by gas chromatography using hexadecane as an internal standard. The results are shown in FIGS. 1A, 1B, and 1C which show comparative reaction profiles for a series of cross-coupling reactions where either compound 86 (●) or Pd$_2$(dba)$_3$ (■) was used a precatalyst. Reactions A and B: Pd (1 mol %), XPhos (2 mol %), ArBr (1 mmol), ArNH$_2$ (1.1 mmol), NaOtBu (1.4 mmol) in toluene (2 mL) at 80° C. Reaction C: Pd (3 mol %), XPhos (6 mol %), ArBr (1 mmol), ArNH$_2$ (1.3 mmol), NaOtBu (1.4 mmol) in toluene (3 mL) at 100° C. All reactions were done with 0.1 mmol hexadecane as an internal standard. Data were fit to sigmoidal functions; no attempt was made to analyze the kinetics of these reactions.

The reaction progress data clearly show higher rates of catalyst turnover when 65 is used in place of $Pd_2(dba)_3$ as the precatalyst. Since the actual catalyst in both cases is the same $[Pd(XPhos)_2]$, the different rates must arise from different concentrations of the catalyst available to turnover. This is consistent with the observed rapid irreversible formation of $PdL_2$ from 86 and phosphine ligands. It is interesting to note that the initial rates of the reactions utilizing 86 are slowed due to the presence of an induction period. We ascribe this induction period to the undesired formation of coordination complexes between the Lewis basic pyridines and 86 in competition with reductive elimination to form the active $PdL_2$ species (Scheme 2). (Norton, D. M.; Mitchell, E. A.; Botros, N. R.; Jessop, P. G.; Baird, M. C. *J. Org. Chem.* 2009, 74, 6674). As the PdL2 catalyst forms, it is less electrophilic than the precatalyst and less likely to form unreactive coordination complexes, leading to a steady increase in concentration of active catalyst and therefore an increased rate of product formation. A recent report comparing 65 with other Pd precatalysts for the Suzuki-Miyaura coupling of bromoanisole and phenylboronic acid do not display induction periods, presumably because of the lack of competitively coordinating substrates (Fraser, A. W.; Besaw, J. E.; Hull, L. E.; Baird, M. C. *Organometallics* 2012, Articles ASAP).

Reaction Scheme 2

Scheme 2. Proposed origin of the induction periods observed in reactions shown in FIGS. 1A, 1B and 1C: competition between reversible formation of the Lewis-base (B) coordination complex of 86 and irreversible reductive elimination of the Cp and Cinn ligands of 86 in the presence of XPhos to form the catalytically active $Pd(XPhos)_2$.

Unlike with 86, the formation of inactive coordination complexes with $Pd_2(dba)_3$ remains in continuous equilibrium with formation of $PdL_2$—each intermediate (e.g. (dba)$PdL_2$ (Amatore, C.; Jutand, A. Coordin. *Chem. Rev.* 1998, 178, 511) can form new complexes with lewis bases. This equilibrium may explain why the product yields are much lower than reactions using 86 for A, B and C in FIG. 1—the concentration of active catalyst never reaches a sustained level suitable for catalysis to occur. The relative Lewis-basicities of the substrates support this explanation, as the $Pd_2(dba)_3$ product
yields are lower for the reactions with 3-aminopyridine as a substrate (A and C in FIG. 1) than for 2-hexynylpyridine (B).

Example 9 Measuring Kinetic and Electrochemical Data Resulting from the Reaction of Peroxyl Radicals with a Selection of Compounds Rate constants ($k_H$ ($M^{-1}$ $s^{-1}$)) were obtained for the reaction between peroxyl radicals and diarylamines using a radical clock method. The approach is identical to the clock reported by Jha and Pratt (Jha, M.; Pratt, D. A.; Chem. Commun., 2008, 1252) with the exception that a naphthyl-based perester (A) was used in place of phenyl-based perester (B). By measuring the ratio of conjugated/non-conjugated products, the rate constant for H-atom transfer ($k_H$) can be measured.

Reaction Scheme 3

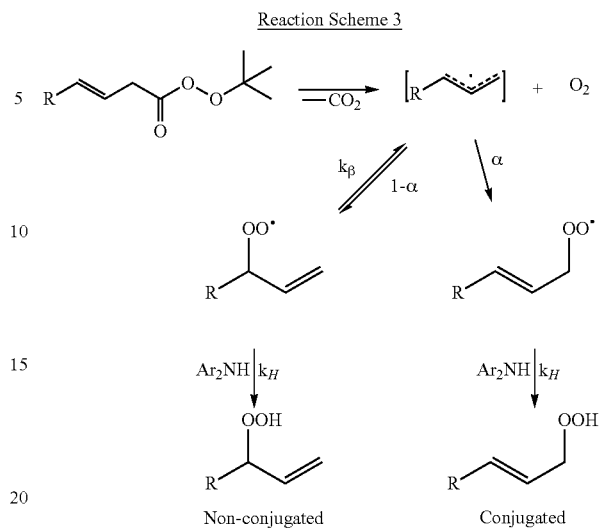

$$\frac{[\text{Conjugated}]}{[\text{Non-Conjugated}]} = \frac{k_\beta}{k_H[\text{Ar}_2\text{NH}]}\left(\frac{1-\alpha}{\alpha}\right) + \frac{1-\alpha}{\alpha} \quad \text{Equation 1}$$

In a typical experiment, perester (15 mM) is incubated at 37° C. with the antioxidant (10-120 mM) in a solvent of choice for 14 hours. In this case, the solvent of choice was chlorobenzene at 37 C. The sample was then quenched with 100 uL of 1 M $PPh_3$ and analyzed by GC using a J&B scientific DB-5 (30 m×320 μm×0.25 μm) column with temperature program: 130° C. hold 5 min, 2° C./min to 170° C., 22° C./min to 280° C., hold 5 min. Standard retention times: Non-conjugated ketone 12.08 min, Non-conjugated alcohol 12.38 min, Conjugated aldehyde 17.71, Conjugated alcohol 19.34. Response factors vs. BnOH are 1.25, 1.85, 1.83 and 1.21 respectively.

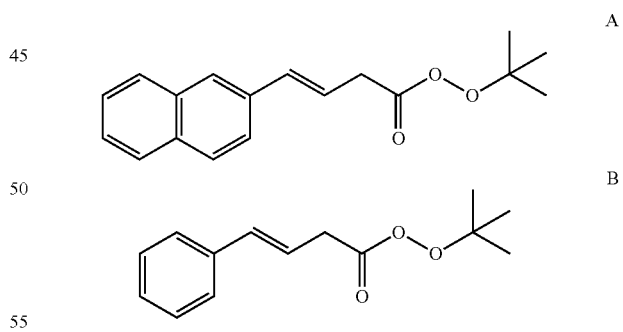

Standard potentials) (E°) and anodic peak potentials ($E_{pa}$) were obtained by cyclic voltammetry and differential pulse voltammetry, respectively, utilizing a glassy carbon working electrode, a platinum counter electrode and a $Ag/AgNO_3$ (0.005 M) reference electrode. Measurements were obtained at room temperature (25 C) in degassed acetonitrile (dried over $CaH_2$) using $Bu_4N$—$PF_6$ (0.1 M, recrystallized twice from abs. EtOH) as electrolyte and sample concentrations of 0.002 M. Fc/Fc+ was used as a reference, corrected to +110 mV vs. $Ag/AgNO_3$ and given vs. NHE (+630 mV). Cyclic voltammagrams revealed reversible or quasi-reversible redox chemistry for all of the N,N-dialkylamino-substituted compounds (be they symmetrical 93, 94-98 or unsymmetrical 104-108) and irreversible for nearly all of the alkyl- and alkoxy-substituted compounds. For compounds displaying reversible redox chemistry, cyclic voltammograms were obtained using a scan rate of 100 mV/s. For compounds displaying irreversible redox chemistry, differential pulse voltammograms were obtained using a scan rate of 20 mV/s.

Differential pulse voltammetry was used to measure anodic peak potentials ($E_{pa}$) for a series of compounds with irreversible redox chemistry. Resulting data for synthesized compounds 23 to 37 are shown in Table 7 below and compared with commercially available known substituted diphenylamines 4,4'-dioctyl diphenylamine and N-phenyl-N',N'-dimethylphenylenediamine. Also included is data obtained for testing 4,4'(dimethylamino)diphenylamine which provides an unstable diphenylamine as a useful negative control in our experiments, and N,N'-bis(4-butylphenyl)phenylenediamine, which provides a comparison for generic N,N'-bis(phenyl)phenylenediamines. Compounds shown in Table 7 are as outlined in Example 6 and are identified by compound number and name as described therein. Inhibition rate constants $k_H (M^{-1} s^{-1})$ and $E°$ vs NHE are obtained as described herein.

TABLE 7

Kinetic/Electrochemical Data with Novel Diarylamines 23 to 37.

| Compound | $k_H (M^{-1}s^{-1})^a$ | $E°$ vs NHE[b] |
|---|---|---|
| 4,4'-dioctyl Diphenylamine | $(4.9 \pm 1.1) \times 10^4$ | 1058 |
| 4,4'-(dimethylamino) diphenylamine | n/a[c] | 343 |
| N-phenyl-N',N'-dimethyl phenylenediamine | $(1.0 \pm 0.3) \times 10^7$ | 514 |
| 24 $N^1,N^1$-dibutyl-$N^4$-(pyrimidin-5-yl)benzene-1,4-diamine | $(3.9 \pm 0.1) \times 10^6$ | 557 |
| 25 $N^1,N^1$-dimethyl-$N^4$-(pyridin-2-yl)benzene-1,4-diamine | $(3.0 \pm 0.4) \times 10^6$ | 571 |
| 26 $N^1,N^1$-dipropyl-$N^4$-(pyrimidin-2-yl) benzene-1,4-diamine | $(7.2 \pm 0.1) \times 10^4$ | 639 |
| 27 $N^2,N^2$-dimethyl-$N^5$-phenyl pyridine-2,5-diamine | $(5.3 \pm 0.8) \times 10^6$ | 603 |
| 28 $N^2,N^2$-dimethyl-$N^5$-phenyl pyrimidine-2,5-diamine | $(1.3 \pm 0.5) \times 10^6$ | 807 |
| 29 $N^5$-(6-dimethylamino pyridin-3-yl)-$N^2,N^2$-dimethyl pyridine-2,5-diamine | $(9.2 \pm 1.1) \times 10^6$ | 436 |
| 30 $N^5$-(4-(dimethylamino)phenyl)-$N^2,N^2$-dimethyl pyrimidine-2,5-diamine | n/a[c] | 437 |
| 31 $N^5$-(4-(dimethylamino)phenyl)-$N^2,N^2$-dimethyl pyridine-2,5-diamine | n/a[c] | 369 |
| 32 $N^5$-(6-(dimethylamino)pyridin-3-yl)-$N^2,N^2$-diethylpyrimidine-2,5-diamine | $(8.4 \pm 1.2) \times 10^6$ | 497 |
| 33 $N^5$-(2-(diethylamino)pyrimidin-5-yl)-$N^2,N^2$-diethylpyrimidine-2,5-diamine | $(4.9 \pm 1.9) \times 10^6$ | 648 |

TABLE 7-continued

Kinetic/Electrochemical Data with Novel Diarylamines 23 to 37.

| Compound | $k_H (M^{-1}s^{-1})^a$ | $E°$ vs NHE[b] |
|---|---|---|
| 34 bis(6-methoxypyridin-3-yl)amine | $(9.1 \pm 1.1) \times 10^5$ | 1029[d] |
| 35 bis(6-(hex-1-ynyl)pyridin-3-yl)amine | $(3.3 \pm 2.1) \times 10^5$ | 1469[d] |
| 36 bis(6-hexylpyridin-3-yl)amine | $(2.1 \pm 0.7) \times 10^5$ | n/a |
| 37 6-methoxy-N-(4-methoxyphenyl)pyridin-3-amine | $(1.0 \pm 0.9) \times 10^6$ | 1101 |

[a]Data obtained in chlorobenzene at 37° C.
[b]Data obtained in acetonitrile at 25° C.
[c]This compound was unstable to the experimental condition measurement impossible.
[d]Anodic peak potentials; voltammagrams were not revers 59/2 mV to compare with $E°$.

It was demonstrated that most compounds that have been synthesized and tested are at least 100-fold more reactive at trapping peroxyl radicals than the commercial standard, 4,4'-dioctyldiphenylamine under ambient conditions. The results are also consistent with our theoretical predictions from calculations based on model structures.

Inhibition rate constants ($k_H$) were also measured for additional compounds in a comprehensive manner to more easily determine trends, and five sets of diarylamine antioxidants were tested—including those substituted with alkyl, alkoxyl, and N,N-dialkylamino groups symmetrically (ie. The same para-substituents on both aromatic rings) and those substituted with alkoxy and N,N-dialkylamino groups unsymmetrically (i.e. para-substituents on only one aromatic ring). The results are shown below in Tables 8-11. (Note that compounds have been sequentially numbered for ease of reference to the corresponding data, but as will be understood, the same compounds may already be referred to herein with a different numerical reference).

TABLE 8

Reactivity of Disubstituted Alkylated Diarylamines Towards Peroxyls and Corresponding Oxidation Potentials.

| | A | B | C | D | R, R'[a] | $k_H (\times 10^5)$[b] | $E_{pa}$[c] |
|---|---|---|---|---|---|---|---|
| 87 | CH | CH | CH | CH | $C_8, C_8$ | $1.8 \pm 1.1$ | 1.02 |
| 88 | N | CH | CH | CH | $C_6, C_4$ | $1.5 \pm 1.1$ | 0.95 |
| 89 | N | N | CH | CH | $C_7, C_4$ | $1.3 \pm 0.1$ | 1.13 |
| 90 | N | CH | N | CH | $C_6, C_5$ | $0.9 \pm 0.3$ | 1.12 |
| 91 | N | N | N | CH | $C_7, C_6$ | $0.8 \pm 0.1$ | 1.50 |
| 92 | N | N | N | N | $C_7, C_7$ | $0.3 \pm 0.1$ | 1.55 |

[a]Linear alkyl chain of indicated lengths.
[b]Values in $M^{-1}s^{-1}$ determined at 37° C. in PhCl using the peroxyl radical clock methodology.
[c]Anodic peak potentials in V vs. NHE determined at 25° C. by differential pulse voltammetry in $CH_3CN$.

TABLE 9

Reactivity of Disubstituted NA-Dialkylaminated Diarylamines Towards Peroxyls and Corresponding Oxidation Potentials.

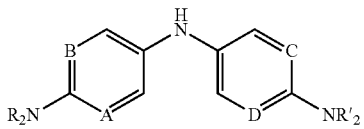

| | A | B | C | D | R, R' | $k_H$ (x$10^7$)[a] | $E^{o}$[b] |
|---|---|---|---|---|---|---|---|
| 93 | CH | CH | CH | CH | Me, Me | —[c] | 0.34 |
| 94 | N | CH | CH | CH | Me, Me | —[c] | 0.37 |
| 95 | N | N | CH | CH | Me, Me | 3.7 ± 1.0 | 0.44 |
| 96 | N | CH | N | CH | Me, Me | 3.4 ± 1.1 | 0.44 |
| 97 | N | N | N | CH | Me, Et | 3.1 ± 1.2 | 0.50 |
| 98 | N | N | N | N | Et, Et | 1.8 ± 1.9 | 0.65 |

[a]Values in $M^{-1}s^{-1}$ determined at 37° C. in PhCl using the peroxyl radical clock methodology.
[b]Values in V vs. NHE determined at 25° C. by cyclic voltammetry in acetonitrile.
[c]Compounds were unstable under reaction conditions.

TABLE 10

Reactivity of Disubstituted Alkoxylated Diarylamines Towards Peroxyls and Corresponding Oxidation Potentials.

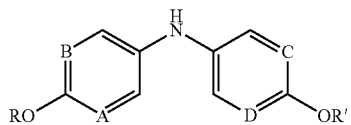

| | A | B | C | D | R,R'[a] | $k_H$ (x$10^6$)[b] | $E_{pa}$[c] |
|---|---|---|---|---|---|---|---|
| 99 | CH | CH | CH | CH | Me, Me | 3.7 ± 0.4 | 0.70 |
| 100 | N | CH | CH | CH | Me, Me | 1.4 ± 1.0 | 0.74 |
| 101 | N | N | CH | CH | PhEt, Bu | nd | 0.88 |
| 102 | N | CH | N | CH | Me, Me | 0.9 ± 0.2 | 0.95 |
| 103 | N | N | N | CH | PhEt, Bu | 0.6 ± 0.1 | 1.03 |

[a]Linear alkyl chain of indicated lengths.
[b]Values in $M^{-1}s^{-1}$ determined at 37° C. in PhCl using the peroxyl radical clock methodology.
[c]Anodic peak potentials in V vs. NHE determined at 25° C. by differential pulse voltammetry in $CH_3CN$.

TABLE 11

Reactivity of Mono-Substituted Diarylamines Towards Peroxyl Radicals and Associated One-Electron Oxidation Potentials.

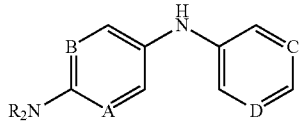

| | A | B | C | D | R | $k_H$ (x$10^7$)[b] | $E^{o}$[c] |
|---|---|---|---|---|---|---|---|
| 104 | CH | CH | CH | CH | Me | 1.3 ± 1.6 | 0.51 |
| 105 | N | CH | CH | CH | Me | 1.1 ± 0.8 | 0.60 |
| 106 | N | N | CH | CH | Me | 0.3 ± 0.6 | 0.81 |
| 107 | CH | CH | N | CH | Me | 0.8 ± 0.2 | 0.53 |
| 108 | CH | CH | N | N | Bu | 0.8 ± 0.1 | 0.56 |
| 109 | CH | CH | CH | CH | Me | 3.0 ± 0.5 | 0.94 |
| 110 | N | CH | CH | CH | Me | 2.9 ± 0.6 | 1.02 |
| 111 | N | N | CH | CH | $C_7$ | 0.6 ± 0.1 | 1.17 |
| 112 | CH | CH | N | CH | Bu | 2.1 ± 0.4 | 0.90 |
| 113 | CH | CH | N | N | $C_{12}$ | nd | 1.34 |

[a]Linear alkyl chain of indicated lengths.
[b]Values in $M^{-1}s^{-1}$ determined at 37° C. in PhCl using the peroxyl radical clock methodology.
[c]Values in V vs NHE determined at 25° C. by cyclic voltammetry in acetonitrile.
[d]Anodic peak potentials in V vs. NHE determined at 25° C. by differential pulse voltammetry in $CH_3CN$.

The same trends are observed for each subset of compounds—oxidation potentials increase upon nitrogen atom incorporation (as little as 0.3 V and as much as 0.53 V for max number of N-atoms) and the inhibition rate constants decrease ca. 2-6 fold upon incorporation of N-atoms, depending on the para-substituents.

With respect to the symmetrically substituted compounds, it was noted that while both series of compounds had increased one-electron oxidation potentials which correlated systematically with N-atom content (between 1.02 and 1.55 V for the alkyl-substituted series and 0.34 and 0.65 V for the N,N-dialkylamino-substituted series), they maintained their reactivities towards peroxyl radicals (cf. Tables 8 and 9). In fact, the N,N-dialkylamino substituted compounds were excellent peroxyl radical trapping antioxidants, having rate constants ca. 200-fold higher than that of the industry standard.

The corresponding alkoxyl-substituted compounds were also preparing and characterizing, and it was found that the oxidation potentials for the series of symmetrically-substituted alkoxylated diarylamines systematically increased with N-atom incorporation and spanned the gap in between the symmetrical alkyl- and N,N-dialkylamino-substituted compounds (0.7-1.03 V), as did the peroxyl-trapping rate constants ($k_H \sim 10^8$ $M^{-1}$ $s^{-1}$) (Table 10).

In addition to the symmetrically-substituted series of diarylamines, two series of mono-substituted compounds having either alkoxy or N,N-dialkylamino substituents on either an aryl or heteroaryl ring were also prepared and tested (Table 11). Interestingly, the substituent effects on the one-electron oxidation potential and rate constants for peroxyl trapping appear to be greater when the substituent group was placed on the heteroaryl ring. At first glance, it is unclear as to why this may be the case. Combining these data with the data for the symmetrically substituted compounds, we correlated the reactivity of each diarylamine towards peroxyl radicals on the basis of N-atom incorporation by plotting log $k_H$ vs. $\Sigma\sigma_p+$ for the para-substituents. Each subset afforded an excellent linear correlation with p+, indicating that the substituent effects on the two aryl rings of the diarylamines are approximately additive. The reaction constants and correlation coefficients as shown in Table 12 below.

TABLE 12

Reaction constants (ρ⁺) from plots of log $k_H$ vs. $\Sigma\sigma_p^+$ for the reactions of substituted diarylamines containing either phenyl, 3-pyridyl or 5-pyrimidyl rings.

| Ar—NH—Ar' | Compounds | ρ⁺(r²) |
|---|---|---|
| Ph—NH—Ph | 87, 93, 99, 104, 109 | −1.59 (0.98) |
| Pyr—NH—Ph | 88, 94, 100, 105, 110, 107, 112 | −1.51 (0.93) |
| Pym-NH—Ph | 89, 95, 101, 106, 111, 108 | −1.00 (0.86) |
| Pyr—NH—Pyr | 90, 96, 102 | −0.94 (0.99) |
| Pym-NH—Pyr | 91, 97, 103 | −0.91 (0.94) |

The negative reaction constants in Table 12 imply that the reaction centre becomes more electrophilic in the transition state compared to the starting material. This follows the established trend that the N—H bond dissociation enthalpies of diphenylamines correlate with $\Sigma\sigma_p+$ because EDGs stabilize the electron-poor diarylaminyl radical (and destabilize the electron-rich diarylamine). Interestingly, the magnitudes of the p+-values decrease with increasing heteroatom incorporation into the aryl rings. This can be attributed to the electronegative nitrogen atoms inductively counteracting the effects of the EDGs thereby reducing their effect on the reactivity of the diarylamines.

Selection of compounds for testing was originally based on hypothetical calculations such as those set out in Example 1. As such, it was important to determine whether the substitution patterns predicted by the calculations are indeed optimal for reactivity/oxidative stability. As such, mono-substituted 2-pyridyl and 2-pyrimidyl derivatives 107B and 108B were prepared and their reactivities compared to their counterpart 3-pyridyl and 5-pyrimidyl compounds 107 and 108.

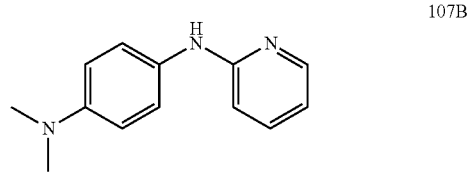

107B

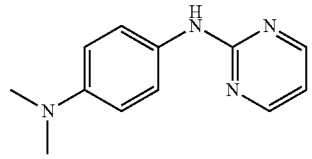

108B

It was found that $k_H=(6.4\pm0.8)\times10^6$ M⁻¹ s⁻¹ and E°=0.57 V for compound 107B, and that $k_H=(1.5\pm0.4)\times10^5$ M⁻¹ s⁻¹ and E°=0.64 V for compound 108B. Although these compounds have only slightly higher one-electron oxidation potentials than their counterparts having nitrogen atoms in the 3 and 5 positions (107, E°=0.53 V and 108, E°=0.56 V), their inhibition rate constants are depressed 1.3-fold and 53-fold respectively for reactions with peroxyl radicals. Therefore, although it is indeed the case that the 2-pyridyl and 2-pyrimidyl analogs are less effective as radical-trapping antioxidants than their 3-pyridyl and 5-pyrimidyl counterparts when tested, the difference is less obvious than was expected from the results of our theoretical calculations on the unsubstituted compounds (cf. Table 1B) when comparing the pyridyl derivatives.

Example 10 Additional Measurement of Kinetic and Electrochemical Data

Rate constants ($k_H$ (M⁻¹ s¹)) can also be obtained for other compounds of the invention by similar reaction between peroxyl radicals and diarylamines using a radical clock method as described in Example 9. Data for synthesized compounds 38 to 41, 43 and 46, for example can be determined and compared with commercially available known substituted diphenylamines 4,4'-dioctyl diphenylamine and N-phenyl-N', N'-dimethylphenylenediamine and 4,4' (dimethylamino)diphenylamine.

Example 11 Testing the Reactivity of Selected Compounds with Alkyl Radicals at 298K Summary data of the reactivity of various other diphenylamines and diarylamines with alkyl radicals at 298K were measured using the radical clock method as described in Example 9. The choice of solvent and the particular group used as a "clock" are noted in Table 13.

TABLE 13

| Compound | $k_H$(M⁻¹s⁻¹) | SOLVENT | Clock |
|---|---|---|---|
| Ph-NH-Ph | 9.6×10⁴ | benzene | neophyl |
| (4-Me-C₆H₄)-NH-(4-Me-C₆H₄) | 6.5×10⁵ | benzene | neophyl |
| (4-MeO-C₆H₄)-NH-(4-MeO-C₆H₄) | 8.8×10⁵ | benzene | neophyl |

TABLE 13-continued

| Compound | $k_H(M^{-1}s^{-1})$ | SOLVENT | Clock |
|---|---|---|---|
| (H₃C)₂N–C₆H₄–NH–C₆H₄–N(CH₃)₂ | (6.5x10⁶) | t-butylbenzene | hexenyl |
| di(pyridin-3-yl)amine | (1.5x10⁵) | benzene | neophyl |
| bis(6-methylpyridin-3-yl)amine | 3.5x10⁵ | benzene | neophyl |
| bis(6-methoxypyridin-3-yl)amine | 9.8x10⁵ | benzene | neophyl |
| bis(6-(dimethylamino)pyridin-3-yl)amine | 4.6x10⁷ | t-butylbenzene | hexenyl |

Rate constants ($k_H$ {M⁻¹ s⁻¹}) were obtained for the reaction between peroxyl radicals and diarylamines using the radical clock method using either hexenyl or neophyl as noted in Table 13, the various noted diarylamines were tested in a thermostatted photoreactor. The competing monomolecular process was the rearrangement of neophyl radical ($k_r$=1.03×10³ s⁻¹), (Franz, J. A.; Barrows, R. D.; Camaioni, D. M. *J. Am. Chem. Soc.* 1984, 106, 3964-4967) or hexenyl radical ($k_r$=2.3×10⁵ s⁻¹) (Chatgilialoglu, C.; Ingold, K. U.; Scaiano, J. C. *J. Am. Chem. Soc.* 1999, 121, 507-514) (as noted), and the reaction was generated at 298K by photolysis of hexabutyldistannane in the presence of the corresponding alkyl bromide.

Additional experiments were performed to review the kinetics of the reactions of alkyl radicals with a series of diarylamines (i.e. those for N—H BDEs were measured) using the radical clock technique. Similar to the peroxyl radical clock methodology described and utilized herein, the alkyl radical clock approach involves the kinetic competition between a unimolecular process with a known rate constant ($k_r$) and the bimolecular reaction under investigation ($k_H$). The 1,2-aryl migration of 2-methyl-2-(2-naphthyl)-1-propyl (MNP) radical was utilized, having kr=1.4× 10⁴ s–1 at 298 K²⁰ as the calibrated unimolecular process, and generated the radicals by photolysis of a deoxygenated solution of MNP—Br in the presence of hexaphenyldistannane according to the reactions given in Reaction Scheme 4 below.

Reaction Scheme 4. Reaction scheme illustrating the application of the alkyl radical clock methodology.

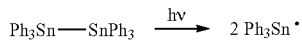

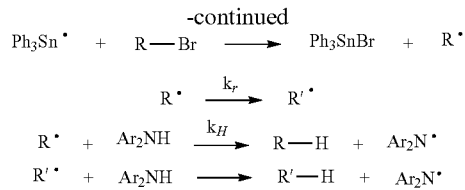

The alkyl radicals react with the diarylamine under investigation, which is present in varying concentrations, with concentration ranges chosen to maintain pseudo first-order kinetics. Under these conditions, the product ratios (determined by GC) can be used to determine the rate of H-atom transfer ($k_H$) to the primary alkyl radical can be calculated according to Eq. 1B. The results are shown in Table 14.

$$k_H[Ar_2NH] = k_r \frac{[RH]}{[R'H]} \quad (1B)$$

TABLE 14

Second-order rate constants for the reactions of selected diarylamines with primary alkyl radicals in chlorobenzene at 25° C.

| Ar₂NH | $k_H$ (M⁻¹s⁻¹) |
|---|---|
| 11 | (2.3 ± 0.9) ×ˣ 10⁵ |
| 14 | (1.5 ± 0.2) ×ˣ 10⁵ |
| 16 | (1.4 ± 0.1) ×ˣ 10⁵ |
| 17 | (2.5 ± 0.1) ×ˣ 10⁴ |
| 20 | (1.9 ± 0.2) ×ˣ 10⁴ |

TABLE 14-continued

Second-order rate constants for
the reactions of selected diarylamines with
primary alkyl radicals in chlorobenzene at 25° C.

| Ar$_2$NH | k$_H$ (M$^{-1}$s$^{-1}$) |
|---|---|
| 2 | (1.3 ± 2.9) x$^x$ 10$^3$ |
| 9 | (9.7 ± 2.3) x$^x$ 10$^2$ |

Example 12 Inhibited Autoxidations

Although peroxyl radical clocks offer a convenient method for determining rate constants for reactions of H-atom donors with peroxyl radicals, as shown in Examples 9-11, the method does not directly demonstrate the inhibition of hydrocarbon autoxidation by antioxidants, and does not account for the number of peroxyl radicals trapped per molecule of antioxidant (i.e. the so-called stoichiometric factor, n). Therefore, autoxidations of styrene were carried out in which small amounts of representative diarylamines were added (see Eq. 2-7), and the reaction progress was followed by oxygen consumption, such that n and k$_{inh}$ (=k$_H$ by the peroxyl radical clock method) could be determined as described in Example 9 (data not shown).

The results reveal pronounced inhibited periods in the presence of the diarylamines (94, 96, and 98)—similar to those observed when the well-studied 2,2,5,7,8-pentamethyl-6-hydroxychroman (PMHC, an analog of α-tocopherol differing simply in that the C$_{16}$H$_{33}$ chain is replaced with CH$_3$) is used an inhibitor, producing stoichiometric factors of ~2.8—slightly larger than for PMHC (n=2), indicating that the products of Equation 7 (as noted below) formed still have some antioxidant activity

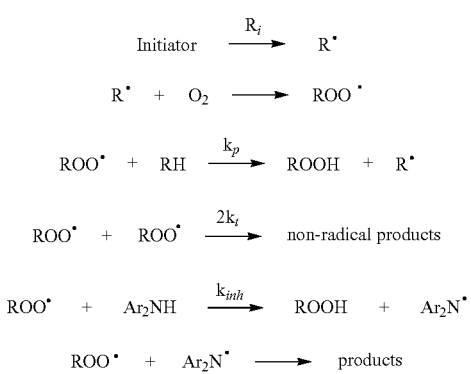

Furthermore, in accordance with the peroxyl radical clock data, the inhibition rate constants obtained from the slopes of these inhibited periods are within a factor of 2 (94: 1.00±0.2×10$^7$; 96: 1.0±0.2×10$^7$; 98: 0.74±0.05×10$^7$M$^{-1}$ s$^{-1}$, regardless of the number of N-atoms incorporated into the aryl rings.) (data not shown).

Example 13 Experimentally Determined N—H Bond Dissociation Enthalpies of Selected Compounds To better understand the effect of nitrogen incorporation on the thermodynamics of H-atom transfer reactions of the diarylamines, the N—H BDEs of a representative set of compounds were measured using the radical-equilibrium electron paramagnetic resonance (EPR) technique (Brigati, G.; Lucarini, M.; Mugnaini, V.; Pedulli, G. F. *J. Org. Chem.* 2002, 67, 4828; Lucarini, M.; Pedrielli, P.; Pedulli, G. F.; Cabiddu, S.; Fattuoni, C. *J. Org. Chem.* 1996, 61, 9259; Bordwell, F. G.; Zhang, X. M.; Cheng, J. P. *J. Org. Chem.* 1993, 58, 6410.) The diaryiaminyl radicals were generated in situ by photolysis of solutions of the diarylamine in benzene containing di-tert-butylperoxide and allowed to reach equilibrium with a hindered phenol of similar O—H bond strength compared to the diarylamine of interest (Eq. 4-6). Representative EPR spectra of equilibrated mixtures were obtained (data not shown) and the N—H BDEs we obtained are provided in Table 14.

$(t\text{-BuO})2 \rightarrow 2t\text{-BuO}.$ (8)

$t\text{-BuO.Ar2NH} \rightarrow t\text{-BuOH+Ar2N.}$ (9)

$\text{Ar2NH+ArO.} \rightleftharpoons \text{Ar2N.+ArOH}$ (10)

The incorporation of nitrogen into the aromatic rings of the substituted diphenylamines leads to a small increase in the N—H bond strength. While the difference seems rather dramatic upon comparing diphenylamine with bis(3-pyridyl)amine (2.7 kcal/mol), the differences appear to get smaller on substitution of the rings (0.9 kcal/mol for the alkyl- and alkoxyl-substituted derivatives and 0.4 kcal/mol for the dialkylamino-substituted derivatives).

The persistence of the diarylaminyl radicals with N,N-dimethylamino substitution suggested they would serve as the best candidates to study to examine the effect of nitrogen incorporation in each of the four positions. Indeed, five of the six possibilities were characterized by N—H BDEs that hardly varied upon incorporation of nitrogen atoms in the aryl rings at the 3 and/or 5-positions (<0.8 kcal/mol).

TABLE 15

N—H Bond dissociation enthalpies of representative diarylamines
measured by the radical equilibration EPR technique in benzene
at 298 K. Values in kcal/mol.

| Y | A | B | C | D | BDE |
|---|---|---|---|---|---|
| H | CH | CH | CH | CH | 84.7 ± 0.7$^a$ |
| H | N | CH | N | CH | 87.4 ± 0.4 |
| CH$_3$ | CH | CH | CH | CH | 82.2 ± 0.6$^a$ |
| CH$_3$ | N | CH | N | CH | 83.1 ± 0.4 |
| C$_8$H$_{17}$ | N | N | N | N | 84.1 ± 0.5 |
| OCH$_3$ | CH | CH | CH | CH | 80.7 ± 0.3$^a$ |
| OCH$_3$ | N | CH | N | CH | 81.6 ± 0.5 |
| N(CH$_3$)$_2$ | CH | CH | CH | CH | 78.4 ± 0.5$^a$ |
| N(CH$_3$)$_2$ | N | CH | N | CH | 78.8 ± 0.3 |
| N(CH$_3$)$_2$ | N | CH | N | CH | 78.8 ± 0.8 |
| N(CH$_3$)$_2$ | N | N | CH | CH | 79.0 ± 0.5 |
| N(CH$_3$)$_2$ | N | N | N | N | 79.2 ± 0.5 |

$^a$Values utilized from prior art.

Example 14 Demonstrating the Utility of Selected Compounds in the Protection of a Monomer (Styrene) at Ambient Temperature In order to demonstrate one aspect of the utility of the compounds described herein, the antioxidant activity of two representative novel diarylmines antioxidants were tested in an autoxidation reaction of styrene at 30° C. Styrene was chosen as representative model for highly oxidizable monomers. The autoxidation was performed in mixtures of styrene (50% v/v) and chlorobenzene as a co-solvent (50% v/v), containing azobisisobutyronitrile (AIBN) as a radical initiator. The reaction was followed by monitoring the consumption of oxygen using an automatic gas-absorption apparatus, built in our laboratories, and based upon the model of a differential pressure transducer (R. Amorati, G. F. Pedulli, L. Valgimigli, O. A. Attanasi, P. Filippone, C. Fiorucci, R. Saladino, J. Chem. Soc., Perkin Trans. 2, 2001, 2142-2146).

In a typical experiment the compositions of the reference and reaction vessels are as shown in Table 16.

TABLE 16

|  | Reference | Sample |
|---|---|---|
| Styrene | 50% v/v | 50% v/v |
| chlorobenzene | 50% v/v | 50% v/v |
| azobisisobutyronitrile | 0.05M | 0.05 mM |
| alpha-tocopherol | 1 mM | 0 |
| Test Diarylamine Compound | 0 | $1 \times 10^{-6}$-$1 \times 10^{-4}$M |

After thermal equilibration the sample (reaction) and reference vessels were isolated and the consumption of oxygen in the sample vessel was automatically recorded. The antioxidant in the sample vessel was either absent (not inhibited autoxidation) or introduced at the beginning of the experiment.

Each of the two tested diarylamine compounds displayed significant retarding of the rate of oxygen consumption at concentrations of $1 \times 10^{-6}$M or higher of the diarylamine, and the slope of the oxygen consumption trace decreased upon increasing the concentration of the diarylamine test compound. Depending on the diarylamine, at concentrations ranging from $2.5 \times 10^{-6}$M to $1 \times 10^{-5}$M or higher the autoxidation was completely inhibited by each of the diarylamines tested, as shown in FIGS. 1-2.

Figure 2:
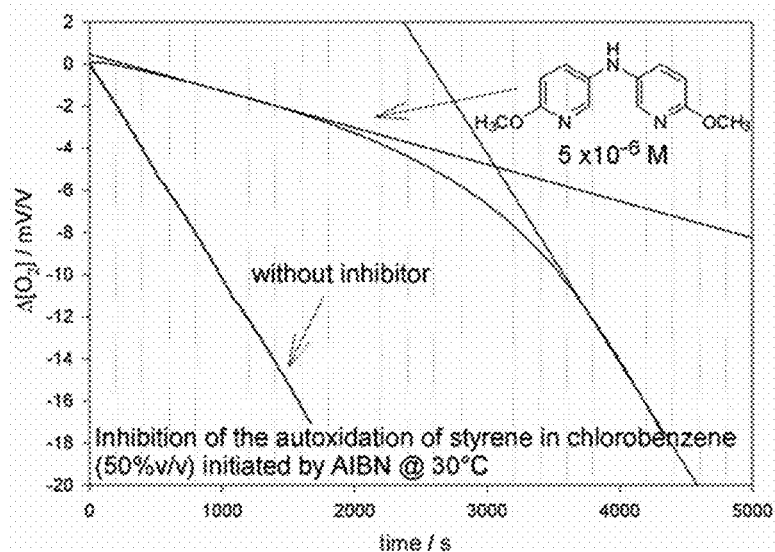
FIG. 2 illustrates, in one embodiment, the oxygen consumption in the autoxidation of styrene at 30° C. in the absence and presence of $5\times10^{-6}M$ 5,5'-dimethoxy-3,3'-dipyridylamine.

FIG. 2 shows the rate of oxygen consumption (as measured in mVN) as monitored during the autoxidation of styrene, when initiated by AIBN at a temperature of 30° C., both in the absence of, or in the presence of $5 \times 10^{-6}$M 5,5'-dimethoxy-3,3'-dipiridylamine. As can be seen, there is almost complete inhibition of auto-oxidation in the presence of the $5 \times 10^{-6}$M 5,5'-dimethoxy-3,3'-dipiridylamine until the diarylamine is completely consumed (after about 2000 s under the reported experimental setting), then the autoxidation accelerates reaching the same rate it was recorded in the absence of antioxidant.

Figure 3:
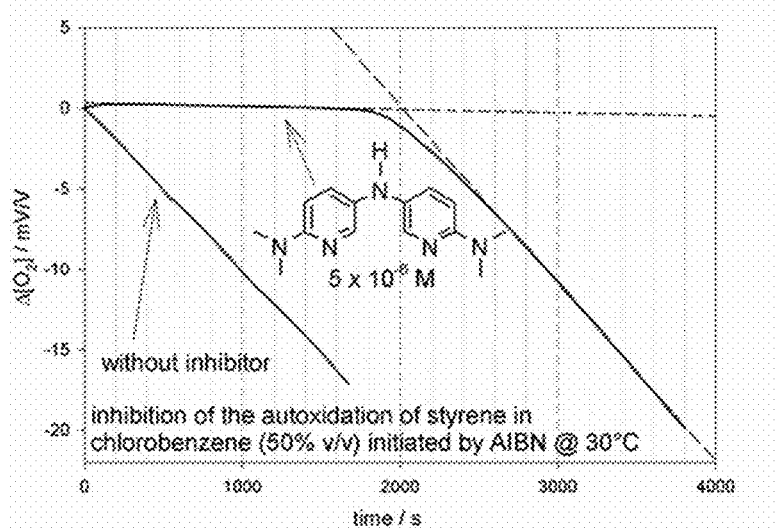
FIG. 3 illustrates, in one embodiment, the oxygen consumption in the autoxidation of styrene at 30° C. in the absence and presence of $5\times10^{-6}$ M 5,5'-dimethylamino-3,3'-dipyridylamine.

FIG. 3 shows the rate of oxygen consumption (as measured in mVN) as monitored during the autoxidation of styrene, when initiated by AIBN at a temperature of 30° C., both in the absence of, or in the presence of $5 \times 10^{-6}$M 5,5'-dimethylamino-3,3'-dipiridylamine. As can be seen, there is complete inhibition of auto-oxidation in the presence of the $5 \times 10^{-6}$M 5,5'-dimethylamino-3,3'-dipiridylamine until the diarylamine is completely consumed (after about 2000 s under the reported experimental setting), then the autoxidation accelerates reaching the same rate it was recorded in the absence of antioxidant.

Using the peroxyl radical clock methodology as described herein, the temperature dependence on the rate of hydrogen-atom abstraction by peroxyl radicals from representative diarylamines was also studied. The β-fragmentation of the secondary (non-conjugated) peroxyl radical was calibrated (log A=12.8 $s^{-1}$ and Ea=9.6 kcal/mol) in the temperature range of 37-95° C. The data is shown in FIG. 3 and the Arrhenius parameters determined from them are given in Table 17.

Figure 4:
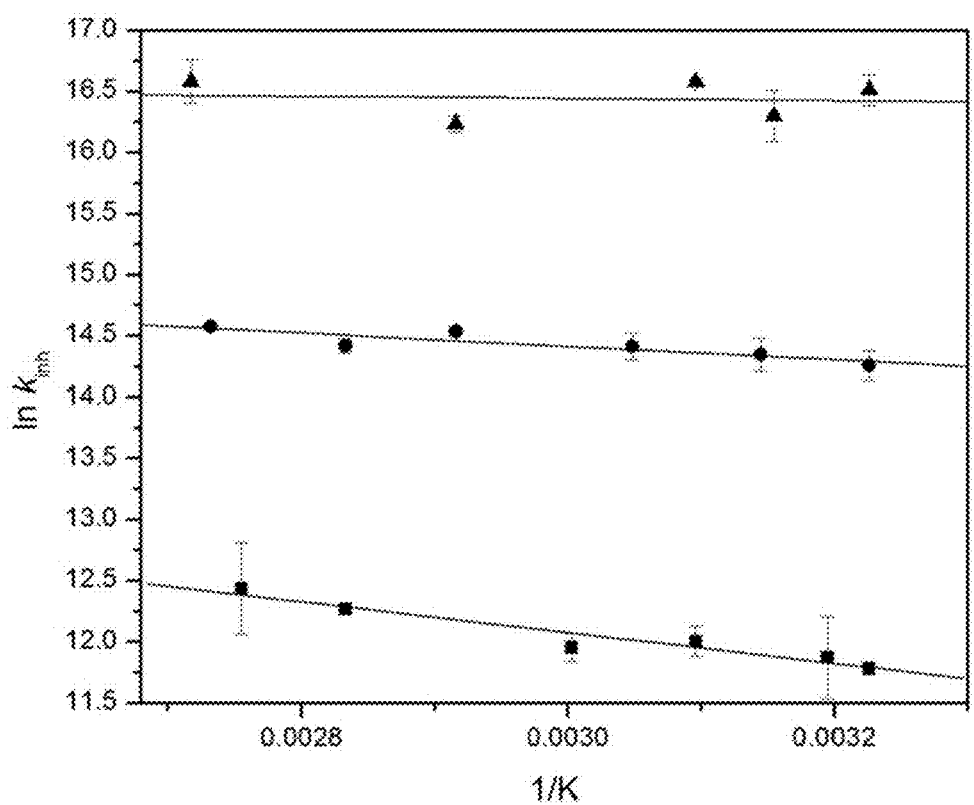
FIG. 4 illustrates, in one embodiment, the temperature dependence on the rate of hydrogen-atom abstraction by peroxyl radicals from selected compounds.

FIG. 4 shows the temperature dependence of the rate constants for reactions of diarylamines 87 (■) (Table 8), 102 (●) (Table 10) and 108 (▲) (Table 11) with peroxyl radicals in chlorobenzene in the range of 37-95° C. Arrhenius paramters for the reactions of the selected diarylamines as shown in FIG. 3 with secondary peroxyl radicals derived from rate constants as measured are shown in Table 16 below.

TABLE 17

Arrhenius parameters for the reactions of selected diarylamines with secondary peroxyl radicals derived from rate constants measured from 37 to 95° C. in chlorobenzene.

| $Ar_2NH$ | logA | $E_a$ (kcal/mol) |
|---|---|---|
| 87 | 6.9 ± 0.2 | 2.5 |
| 102 | 7.0 ± 0.1 | 1.1 |
| 108 | 7.1 ± 0.1 | 0 |

Example 15 Demonstrating the Utility of Selected Compounds in the Protection of a Polyunsaturated Fat at Ambient Temperature In order to demonstrate the utility of compounds as described herein in one aspect, the antioxidant activity of one representative novel diarylmines antioxidants was tested in an autoxidation reaction of methyl linoleate at 30° C. Methyl linoleate was chosen as representative model for the autoxidation of polyunsaturated triglycerides and phospholipids. The autoxidation was performed in solution of methyl linoleate 1 M in chlorobenzene as a solvent, containing azobisisobutyronitrile (AIBN) as a radical initiator. The reaction was followed by monitoring the consumption of oxygen using an automatic gas-absorption apparatus, built in our laboratories, and based upon the model of a differential pressure transducer (R. Amorati, G. F. Pedulli, L. Valgimigli, O. A. Attanasi, P. Filippone, C. Fiorucci, R. Saladino, J. Chem. Soc., Perkin Trans. 2, 2001, 2142-2146).

In a typical experiment the compositions of the reference and reaction vessels are as shown in Table 18.

TABLE 18

|  | Reference | Sample |
|---|---|---|
| Methyl linoleate | 1M in chlorobenzene | 1M in chlorobenzene |
| azobisisobutyronitrile | 0.05M | 0.05 mM |
| alpha-tocopherol | 1 mM | 0 |
| Test Diarylamine Compound | 0 | $1 \times 10^{-6}$-$1 \times 10^{-4}$M |

After thermal equilibration the sample (reaction) and reference vessels were isolated and the consumption of oxygen in the sample vessel was automatically recorded.

The antioxidant in the sample vessel was either absent (not inhibited autoxidation) or introduced at the beginning of the experiment.

The tested diarylamine compound displayed significant retarding of the rate of oxygen consumption at concentrations of $1 \times 10^{-6}$M or higher of the diarylamine, and the slope of the oxygen consumption trace decreased upon increasing the concentration of the diarylamine test compound. At concentrations ranging from $3 \times 10^{-6}$M or higher the autoxidation was completely inhibited, as shown in FIG. 5.

Figure 5:
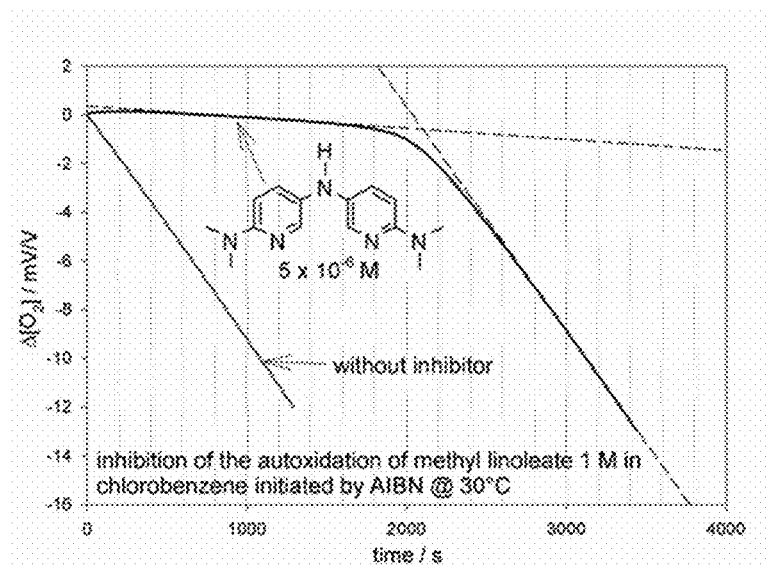
FIG. 5 illustrates, in one embodiment, the oxygen consumption in the autoxidation of methyl linoleate at 30° C. in the absence and presence of $5\times10^{-6}M$ 5,5'-dimethylamino-3,3'-dipyridylamine.

FIG. 5 shows the rate of oxygen consumption (as measured in mVN) as monitored during the autoxidation of methyl linoleate, when initiated by AIBN at a temperature of 30° C., both in the absence of, or in the presence of $5 \times 10^{-6}$M 5,5'-dimethylamino-3,3'-dipiridylamine. As can be seen, there is complete inhibition of auto-oxidation in the presence of the $5 \times 10^{-6}$M 5,5'-dimethylamino-3,3'-dipiridylamine until the diarylamine is completely consumed (after about 2000 s under the reported experimental setting), then the autoxidation accelerates reaching the same rate it was recorded in the absence of antioxidant.

Example 16 Demonstrating High Temperature Utility of Compounds of the Invention

In order to demonstrate the high temperature utility of compounds of the invention, the antioxidant activity of three representative novel diarylmines antioxidants were tested in an autoxidation reaction of hexadecane at 120° C. The autoxidation was performed in mixtures of hexadecane (75% v/v) and dichlorobenzene (25% v/v), containing dicumylperoxide (1.9 mM) as a radical initiator. The reaction was followed by monitoring the consumption of oxygen using an automatic gas-absorption apparatus, built in our laboratories, and based upon the model of a differential pressure transducer (R. Amorati, G. F. Pedulli, L. Valgimigli, O. A. Attanasi, P. Filippone, C. Fiorucci, R. Saladino, *J. Chem. Soc., Perkin Trans.* 2, 2001, 2142-2146).

To modify the standard equipment used for autoxidation studies at 30-37° C. to allow the equipment to work at higher temperatures, the instrument was modified by replacing the peek HPLC tubing, connecting the sample and reference reaction vessels with the pressure transducer using an inert HPLC titanium tubing, and replacing the thermostatting water bath with a silicon-oil bath.

In a typical experiment the compositions of the reference and reaction vessels are as shown in Table 19.

TABLE 19

|  | Reference | Sample |
| --- | --- | --- |
| Hexadecane | 75% v/v | 75% v/v |
| 1,2-dichlorobenzene | 25% v/v | 25% v/v |
| dicumylperoxide | 1.9 mM | 1.9 mM |
| diphenylamine | 5 mM | 0 |
| Test Diarylamine Compound | 0 | $1 \times 10^{-6}\text{-}1 \times 10^{-3}$M |

After thermal equilibration the sample (reaction) and reference vessels were isolated and the consumption of oxygen in the sample vessel was automatically recorded. The antioxidant in the sample vessel was either introduced at the beginning of the experiment or autoxidation was allowed to start without inhibition, and then the system was re-equilibrated and the antioxidant injected. This second experimental setting allowed us to reference the rate of oxygen consumption in the presence of antioxidant and compare it to the corresponding rate in the exact same system before antioxidant injection.

Each of the three tested diarylamine compounds displayed significant retarding of the rate of oxygen consumption at concentrations of $5 \times 10^{-6}$M or higher of the diarylamine, and the slope of the oxygen consumption trace decreased upon increasing the concentration of the diarylamine test compound. At concentration of $1 \times 10^{-4}$M or higher the autoxidation was completely inhibited by each of the diarylamines tested, as shown in FIGS. 6-8.

Figure 6:
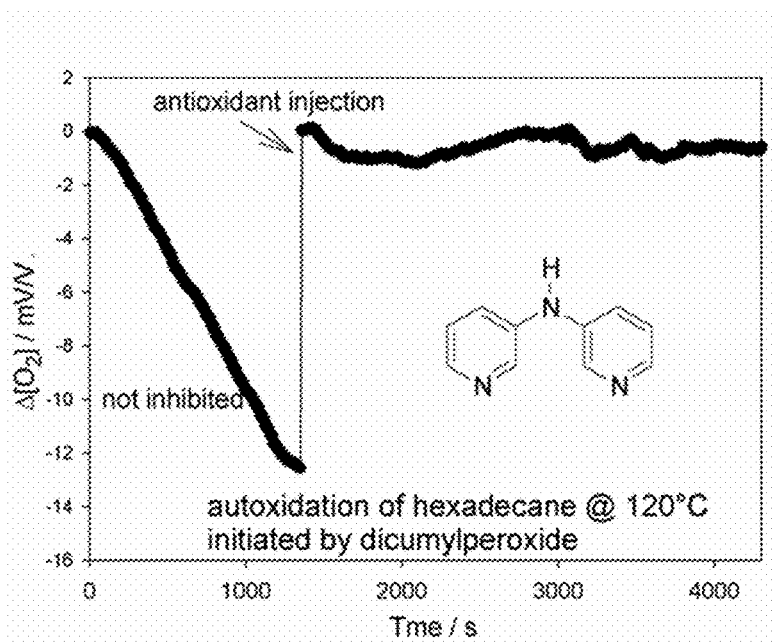
FIG. 6 illustrates, in one embodiment, the oxygen consumption of hexadecane at 120° C. in the absence and presence of $1.5\times10^{-4}$ M 3,3'-dipyridylamine.

FIG. 6 shows the rate of oxygen consumption (as measured in mVN) as monitored during the autoxidation of hexadecane, when initiated by the dicumylperoxide at a temperature of 120° C., both in the absence of, and after injection of $1.5 \times 10^{-4}$M 3,3'-dipiridylamine. As can be seen, there is significant inhibition of auto-oxidation in the presence of the $1.5 \times 10^{-4}$M 3,3'-dipiridylamine.

Figure 7:
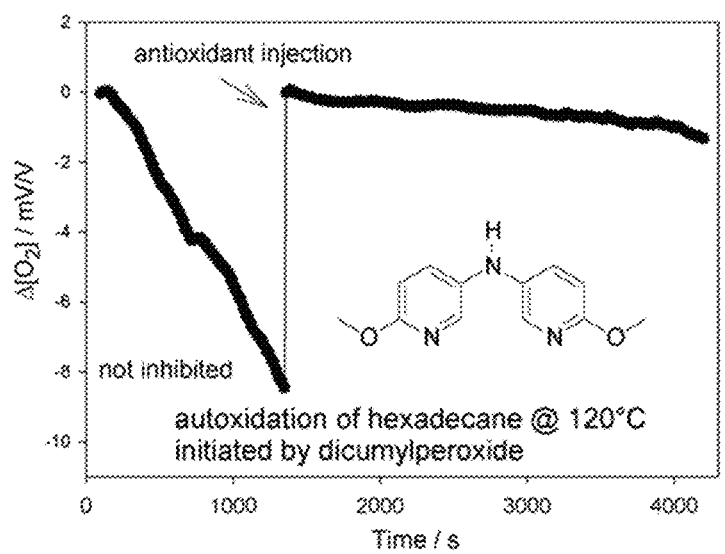
FIG. 7 illustrates, in one embodiment, the oxygen consumption of hexadecane at 120° C. in the absence and presence of $1.0\times10^{-4}$ M 5,5'-dimethoxy-3,3' dipyridylamine.

FIG. 7 shows the rate of oxygen consumption (as measured in mVN) as monitored during the autoxidation of hexadecane, when initiated by the dicumylperoxide at a temperature of 120° C., both in the absence of, and after injection of $1.0 \times 10^{-4}$M 5,5'-dimethoxy-3,3'-dipiridylamine. Again, there is significant inhibition of auto-oxidation, even at these high temperatures, indicating that the antioxidants of the invention have utility at both lower and higher temperatures.

Figure 8:
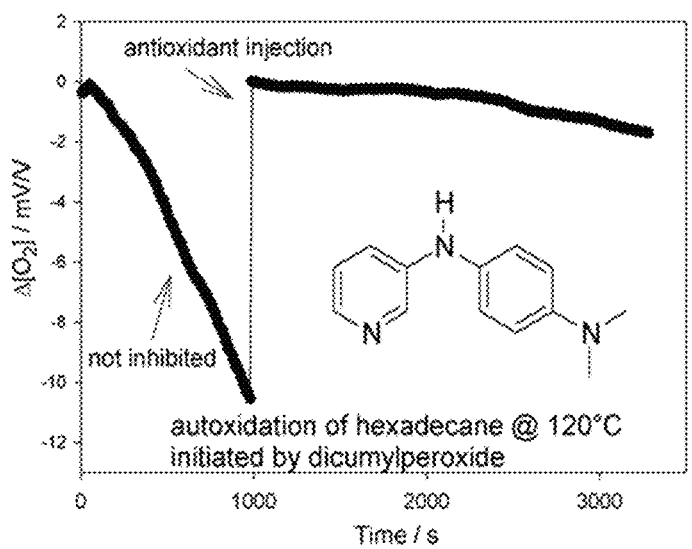
FIG. 8 illustrates, in one embodiment, the oxygen consumption of hexadecane at 120° C. in the absence and presence of $1.0\times10^{-4}$ M 3-pyridyl-4'-dimethylaminophenylamine.

FIG. 8 shows the rate of oxygen consumption (as measured in mVN) as monitored during the autoxidation of hexadecane, when initiated by the dicumylperoxide at a temperature of 120° C., both in the absence of, and after injection of $1.0 \times 10^{-4}$ M 3-pyridyl-4'-dimethylaminophenylamine. Again significant anti-oxidant activity is seen at these higher temperatures.

Example 17 Lubricating Oil Formulation A

A lubricating oil composition can be prepared comprising a substituted diarylamine antioxidant of the current invention. The lubricating oil can contain 90%, by weight, fatty acid ester, 2%, by weight, isononanoic acid (branched) and fatty acid ($C_{12}$ to $C_{72}$), 6%, by weight, compound 114, and 2%, by weight, phosphorous based additive.

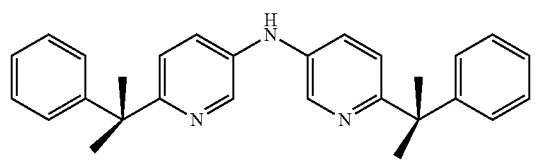

114

Example 18 Lubricating Oil Formulation B

A lubricating oil formulation can be prepared containing a hydrocarbon base oil, a metal passivator, a foam inhibitor, a demulsifier, 0.5%, by weight, phenyl-alpha-naphthylamine (not substituted), 0.5%, by weight, antioxidant compound 115 (shown below), 0.1%, by weight, aspartic acid N-(3-carboxy-1-oxo-2-propenyl)-N-octadecyl-bis(2-methylpropyl)ester (a rust inhibitor), and 0.1%, by weight, LZ®5125 (an amine salt of dialkylthiophosphate which is an antiwear agent commercially available from Lubrizol®).

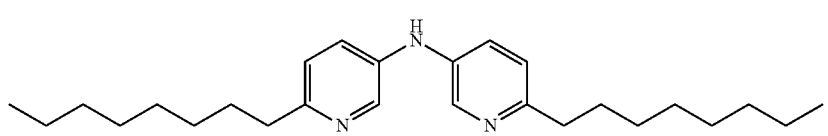

115

Example 19 Testing Lubricating Oil Formulations of the Invention

Formulations can be subjected to a test for high temperature oxidation stability, including using the test known as the oxidation test DIN 51394 performed according to the high temperature modifications set out in the General Electric specifications GEK 32568 C and GEK 101941, in order to assure suitability for purpose. In this test, the oil is maintained at 175° C. for 72 hours in the presence of five metal catalysts (copper, steel, aluminium, magnesium, silver) whilst air is bubbled through the oil at a rate of 3 1/hour. At the end of the test, the oil is analysed for its viscosity increase, its increase in total acid number and the total amount of sludge produced. The sludge must be removed carefully from the equipment, especially from the full height of the sides of the cylinder. The sludge is separated by filtration with the help of 5 micron filtration paper available from Millipore, the sludge removed is washed with n-heptane and subsequently dried and weighed.

Example 20 Use of an Antioxidant of the Invention to Stabilize Rubber

Compositions containing natural rubber can be stabilized by adding 2% by weight of compound 116.

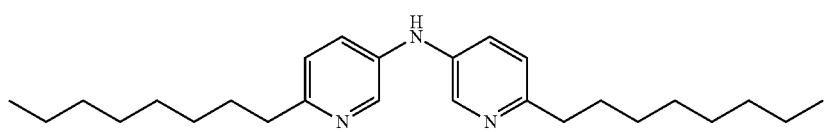

116

Therefore we have identified substituted diaryl amines which are able to demonstrate excellent antioxidant properties as well as improved stability at lower temperatures when compared with traditional diphenylamine antioxidants, thus making for compounds which have enhanced efficacy and storage stability. The ease of the preparation of these compounds, and the combination of their air stability and high reactivity to peroxyl radicals, indicates their utility in a variety of applications protecting organic substrates from degradation.

The above-described embodiments of the present invention are intended to be examples only. Alterations, modifications and variations may be effected to the particular embodiments by those of skill in the art without departing from the scope of the invention, as by the claims appended hereto. For example, many of the compounds of the present invention exist in stereoisomeric forms, and the present invention extends to cover all such stereoisomers exhibiting the same or similar utility as an antioxidants.

That is claimed is:

1. A compound of Formula II, or a salt thereof,

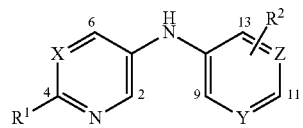

(II)

wherein each of X, Y, and Z are independently a carbon or nitrogen atom, and at least one of X, Y, or Z are nitrogen, wherein $R^1$ is an electron donating group, and $R^2$ is a hydrogen or an electron donating group bonded to a carbon atom in its aryl ring, wherein an electron donating group comprises a hydrocarbon group, an alkoxy group ($OR^3$), an amine group ($NH_2$), a monosubstituted amine ($NHR^4$) group, or a disubstituted amine ($NR^4R^5$) group, wherein $R^3$, $R^4$ and $R^5$ are independently hydrogen, saturated or unsaturated branched or straight chain hydrocarbon moiety, cycloaliphatic group, aromatic hydrocarbon, or a combination thereof, wherein the carbon atoms at positions 9 and 13 bear hydrogens, and wherein when $R^2$ is $OR^3$, $R^2$ is bonded to the carbon atom at position 11.

2. The compound of claim 1 wherein the electron donating group is:
   (i) an aliphatic moiety, an aromatic moiety or a combination thereof;
   (ii) $OR^3$ wherein $R^3$ is a hydrogen or an aliphatic moiety, an aromatic moiety or a combination thereof; or
   (iii) $NR^4R^5$ wherein $R^4$ and $R^5$ are each independently hydrogen or an aliphatic moiety, an aromatic moiety or a combination thereof.

3. The compound of claim 1 wherein the electron donating group is:
   (i) a $C_1$ to $C_{20}$ hydrocarbon group;
   (ii) $OR^3$ wherein $R^3$ is a hydrogen or a $C_1$ to $C_{20}$ hydrocarbon group; or
   (iii) $NR^4R^5$ wherein $R^4$ and $R^5$ are each independently hydrogen or a $C_1$ to $C_{20}$ hydrocarbon group.

4. The compound according to claim 1, wherein $R^4$ and $R^5$ are not both hydrogen or $R^3$ is not a hydrogen.

5. The compound according to claim 3, wherein the electron donating group is a linear or branched $C_1$ to $C_{20}$ hydrocarbon group.

6. The compound of claim 1, wherein $R^1$ is:
   (i) a $C_1$ to $C_{20}$ hydrocarbon group;
   (ii) $OR^3$ wherein $R^3$ is a hydrogen or a $C_1$ to $C_{20}$ hydrocarbon group; or
   (iii) $NR^4R^5$ wherein $R^4$ and $R^5$ are each independently hydrogen or a $C_1$ to $C_{20}$ hydrocarbon group.

7. The compound of claim 1, wherein $R^2$ is bonded to a carbon atom at position 11 and is:
   (i) a hydrogen;
   (ii) a $C_1$ to $C_{20}$ hydrocarbon group;
   (iii) $OR^3$ wherein $R^3$ is a hydrogen or a $C_1$ to $C_{20}$ hydrocarbon group; or
   (iv) $NR^4R^5$ wherein $R^4$ and $R^5$ are each independently hydrogen or a $C_1$ to $C_{20}$ hydrocarbon group.

8. A composition comprising an organic substrate and one or more compounds of Formula II, or a salt thereof,

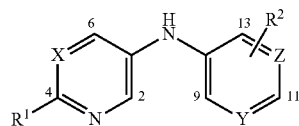

(II)

wherein each of X, Y, and Z are independently a carbon or nitrogen atom, and at least one of X, Y, or Z are nitrogen, wherein $R^1$ is an electron donating group, $R^2$ is a hydrogen or an electron donating group bonded to a carbon atom in its aryl ring, wherein an electron donating group comprises a hydrocarbon group, an alkoxy group ($OR^3$), an amine group ($NH_2$), a monosubstituted amine ($NHR^4$) group, or a disubstituted amine ($NR^4R^5$) group, wherein $R^3$, $R^4$ and $R^5$ are independently hydrogen, saturated or unsaturated branched or straight chain hydrocarbon moiety, cycloaliphatic group, aromatic hydrocarbon, or a combination thereof, wherein the carbon atoms at positions 9 and 13 bear hydrogens, wherein when $R^2$ is $OR^3$, $R^2$ is bonded to the carbon atom at position 11, and wherein the compound(s) are present in an amount sufficient to reduce the level of degradation of the organic substrate when compared to the level of degradation of the organic substrate in the absence of said compound(s).

9. The composition of claim 8 wherein the electron donating group is:
   (i) an aromatic moiety, an aliphatic moiety or a combination thereof;
   (ii) $OR^3$ wherein $R^3$ is a hydrogen or an aromatic moiety, an aliphatic moiety or a combination thereof; or
   (iii) $NR^4R^5$ wherein $R^4$ and $R^5$ are each independently hydrogen or an aromatic moiety, an aliphatic moiety or a combination thereof.

10. The composition of claim 8 wherein the electron donating group is:
    (i) a $C_1$ to $C_{20}$ hydrocarbon group;
    (ii) $OR^3$ wherein $R^3$ is a hydrogen or a $C_1$ to $C_{20}$ hydrocarbon group; or
    (iii) $NR^4R^5$ wherein $R^4$ and $R^5$ are each independently hydrogen or a $C_1$ to $C_{20}$ hydrocarbon group.

11. The composition according to claim 9, wherein $R^4$ and $R^5$ are not both hydrogen or $R^3$ is not a hydrogen.

12. The composition according to claim 10, wherein $R^4$ and $R^5$ are not both hydrogen or $R^3$ is not a hydrogen.

13. The composition according to claim 8, wherein the organic substrate is selected from the group consisting of: lubricants, biofuels, plastics, rubbers, polymers, elastomers, cosmetic preparations, coatings, dyes, inks, pharmaceutical preparations, food preparations and adhesives.

14. The composition according to claim 8, wherein the organic substrate is a lubricant, and the compound(s) are present in an amount of about 0.03 to about 2.5 weight percent of said lubricant.

15. The composition according to claim 8, wherein the composition further comprises one or more additional antioxidants.

16. The composition of claim 15, wherein the additional antioxidant is a sterically hindered phenol.

* * * * *